United States Patent
Gao et al.

(10) Patent No.: US 7,550,461 B2
(45) Date of Patent: Jun. 23, 2009

(54) BENZOFURAN AND BENZOTHIOPHENE COMPOUNDS USEFUL IN TREATING CYTOKINE MEDIATED DISEASES

(75) Inventors: Donghong Amy Gao, Hopewell Junction, NY (US); Daniel R. Goldberg, Redding, CT (US); Abdelhakim Hammach, Danbury, CT (US); Ming-Hong Hao, Ridgefield, CT (US); Victor Marc Kamhi, Danbury, CT (US); Neil Moss, Ridgefield, CT (US); Kevin Chungeng Qian, New Milford, CT (US); Gregory Paul Roth, New Milford, CT (US); Christopher Ronald Sarko, New Milford, CT (US); Alan David Swinamer, Bethel, CT (US); Zhaoming Xiong, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 841 days.

(21) Appl. No.: 10/410,688

(22) Filed: Apr. 10, 2003

(65) Prior Publication Data
US 2003/0225053 A1 Dec. 4, 2003

Related U.S. Application Data

(60) Provisional application No. 60/371,671, filed on Apr. 11, 2002.

(51) Int. Cl.
| | |
|---|---|
| C07D 265/28 | (2006.01) |
| C07D 295/00 | (2006.01) |
| C07D 213/00 | (2006.01) |
| C07D 241/00 | (2006.01) |
| C07D 241/02 | (2006.01) |
| C07D 239/00 | (2006.01) |
| C07D 239/02 | (2006.01) |
| C07D 271/00 | (2006.01) |
| C07D 487/00 | (2006.01) |
| C07D 491/00 | (2006.01) |
| C07D 495/00 | (2006.01) |
| C07D 497/00 | (2006.01) |
| C07D 498/00 | (2006.01) |
| C07D 333/50 | (2006.01) |
| C07D 409/00 | (2006.01) |
| C07D 495/22 | (2006.01) |
| C07D 307/77 | (2006.01) |
| C07D 307/93 | (2006.01) |

(52) U.S. Cl. .............. 514/231.2; 514/247; 514/248; 514/277; 514/443; 514/468; 544/98; 544/242; 544/336; 544/338; 546/1; 549/41; 549/456

(58) Field of Classification Search .......... None
See application file for complete search history.

(56) References Cited

U.S. PATENT DOCUMENTS

| 5,712,304 A | * | 1/1998 | Elbe et al. .......... 514/443 |
| 6,194,443 B1 | * | 2/2001 | Kruger et al. ........ 514/357 |
| 2003/0225053 A1 | * | 12/2003 | Gao et al. .......... 514/183 |

FOREIGN PATENT DOCUMENTS

| WO | WO 99/59959 | 11/1999 |
| WO | WO 00/18738 | 4/2000 |
| WO | WO 00/55139 | 9/2000 |
| WO | WO 0212189 | * 2/2002 |
| WO | WO 02/083628 | 10/2002 |

OTHER PUBLICATIONS

Rastogi et al. Synthesis of 2-substituted benzofurans as potential anthelmintics. Indian Journal of Chemistry, Section B. 1982, 21B(5), 485-487. (Chemical Abstracts).*
Patani and LaVoie, Chemical Reviews, 1996, 96, 3147-76.*
Linde et al. Expert Opinion on Emerging Drugs, 2001, 6(2), 281-302.*
Higham et al. European Respiratory Journal, 2000, 281-284.*
Holden et al. Medical Hypotheses, 1995, 45, 559-71.*
"CHOC Blood and Donor Services", http://www.choc.org/community/blooddonorsvs.cfm, accessed Sep. 13, 2007.*
Goldberg et al. Journal of Medicinal Chemistry, 2007, 50, 4016-26.*
Sekut et al. Expert Opinion in Investigational Drugs, 1998, 7(11), 1825-39.*

* cited by examiner

*Primary Examiner*—James O Wilson
*Assistant Examiner*—Noble Jarrell
(74) *Attorney, Agent, or Firm*—Michael P. Morris; Mary-Ellen M. Devlin; Anthony P. Bottino

(57) ABSTRACT

Disclosed are amide compounds of formula (I):

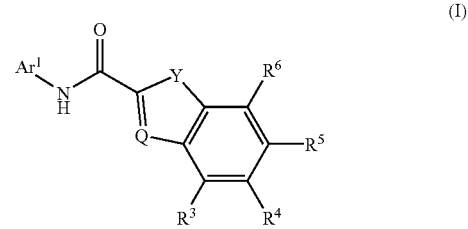

wherein $Ar^1$, Q, Y and $R^3$-$R^6$ of formula (I) are defined herein. The compounds inhibit production of cytokines involved in inflammatory processes and are thus useful for treating diseases and pathological conditions involving inflammation such as chronic inflammatory disease. Also disclosed are processes for preparing these compounds and pharmaceutical compositions comprising these compounds.

9 Claims, No Drawings

BENZOFURAN AND BENZOTHIOPHENE COMPOUNDS USEFUL IN TREATING CYTOKINE MEDIATED DISEASES

TECHNICAL FIELD OF THE INVENTION

This invention relates to amide compounds of formula (I):

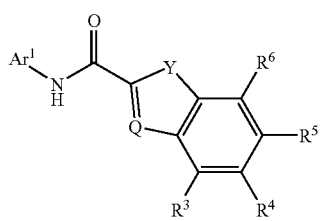

wherein $Ar^1$, Q, Y and $R^3$-$R^6$ of formula (I) are defined below. The compounds of the invention inhibit production of cytokines involved in inflammatory processes and are thus useful for treating diseases and pathological conditions involving inflammation such as chronic inflammatory disease. This invention also relates to processes for preparing these compounds and to pharmaceutical compositions comprising these compounds.

BACKGROUND OF THE INVENTION

Tumor necrosis factor (TNF) and interleukin-1 (IL-1) are important biological entities collectively referred to as proinflammatory cytokines which play a role in cytokine mediated diseases. These, along with several other related molecules, mediate the inflammatory response associated with the immunological recognition of infectious agents. The inflammatory response plays an important role in limiting and controlling pathogenic infections.

Elevated levels of proinflammatory cytokines are also associated with a number of diseases of autoimmunity such as toxic shock syndrome, rheumatoid arthritis, osteoarthritis, diabetes and inflammatory bowel disease (Dinarello, C. A., et al., 1984, *Rev. Infect. Disease* 6:51). In these diseases, chronic elevation of inflammation exacerbates or causes much of the pathophysiology observed. For example, rheumatoid synovial tissue becomes invaded with inflammatory cells that result in destruction to cartilage and bone (Koch, A. E., et al., 1995, *J. Invest. Med.* 43: 28-38). Studies suggest that inflammatory changes mediated by cytokines may be involved in endothelial cell pathogenesis including restenosis after percutaneous transluminal coronary angioplasty (PTCA) (Tashiro, H., et al., March, 2001 *Coron Artery Dis* 12(2):107-13). An important and accepted therapeutic approach for potential drug intervention in these diseases is the reduction of proinflammatory cytokines such as TNF (also referred to in its secreted cell-free form as TNFα) and IL-1β. A number of anti-cytokine therapies are currently in clinical trials. Efficacy has been demonstrated with a monoclonal antibody directed against TNFα in a number of autoimmune diseases (Heath, P., "CDP571: An Engineered Human IgG4 Anti-TNFα Antibody" IBC Meeting on Cytokine Antagonists, Philadelphia, Pa., Apr. 5-24, 1997). These include the treatment of rheumatoid arthritis, Crohn's disease and ulcerative colitis (Rankin, E. C. C., et al., 1997, *British J. Rheum.* 35: 334-342 and Stack, W. A., et al., 1997, *Lancet* 349: 521-524).

The monoclonal antibody is thought to function by binding to both soluble TNFα and to membrane bound TNF.

A soluble TNFα receptor has been engineered that interacts with TNFα. The approach is similar to that described above for the monoclonal antibodies directed against TNFα; both agents bind to soluble TNFα, thus reducing its concentration. One version of this construct, called Enbrel (Immunex, Seattle, Wash.) recently demonstrated efficacy in a Phase III clinical trial for the treatment of rheumatoid arthritis (Brower et al., 1997, *Nature Biotechnology* 15: 1240). Another version of the TNFα receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti, et al., 1997, *Inflamm. Res.* 46: S143).

IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1ra reduced the mortality rate in patients with septic shock syndrome (Dinarello, 1995, *Nutrution* 11, 492). Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier, 1997, *Biomed Pharmacother.* 51, 58). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans, et al., 1996, *J Bone Miner Res.* 11, 300). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al., 1996, *Proc Soc Exp Biol Med.* 211, 24).

Inhibitors of cytokine production are expected to block inducible cyclooxygenase (COX-2) expression. COX-2 expression has been shown to be increased by cytokines and it is believed to be the isoform of cyclooxygenase responsible for inflammation (M. K. O'Banion et al., *Proc. Natl. Acad. Sci. U.S.A,* 1992, 89, 4888.) Accordingly, inhibitors of cytokines such as IL-1 would be expected to exhibit efficacy against those disorders currently treated with COX inhibitors such as the familiar NSAIDs. These disorders include acute and chronic pain as well as symptoms of inflammation and cardiovascular disease.

Elevation of several cytokines have been demonstrated during active inflammatory bowel disease (IBD). A mucosal imbalance of intestinal IL-1 and IL-1ra is present in patients with IBD. Insufficient production of endogenous IL-1ra may contribute to the pathogenesis of IBD (Cominelli, et al., 1996, *Aliment Pharmacol Ther.* 10, 49). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden, et al., 1995, *Med Hypotheses*, 45, 559). A role for IL-1 in the pathogenesis of human immunodeficiency virus (HIV) has been identified. IL-1ra showed a clear relationship to acute inflammatory events as well as to the different disease stages in the pathophysiology of HIV infection (Kreuzer, et al., 1997, *Clin Exp Immunol.* 109, 54). IL-1 and TNF are both involved in periodontal disease. The destructive process associated with periodontal disease may be due to a disregulation of both IL-1 and TNF (Howells, 1995, *Oral Dis.* 1, 266).

Proinflammatory cytokines such as TNFα and IL-1β are also important mediators of septic shock and associated cardiopulmonary dysfunction, acute respiratory distress syndrome (ARDS) and multiple organ failure. In a study of patients presenting at a hospital with sepsis, a correlation was found between TNFα and IL-6 levels and septic complications (Terregino et al., 2000, *Ann. Emerg. Med.*, 35, 26). TNFα has also been implicated in cachexia and muscle degradation, associated with HIV infection (Lahdiverta et al., 1988, *Amer. J. Med.*, 85, 289). Obesity is associated with an increase incidence of infection, diabetes and cardiovascular disease. Abnormalities in TNFα expression have been noted for each of the above conditions (Loffreda, et al., 1998, *FASEB J.* 12, 57). It has been proposed that elevated levels of TNFα are involved in other eating related disorders such as anorexia and bulimia nervosa. Pathophysiological parallels are drawn between anorexia nervosa and cancer cachexia (Holden, et al., 1996, *Med Hypotheses* 47, 423). An inhibitor of TNFα production, HU-211, was shown to improve the outcome of closed brain injury in an experimental model (Shohami, et al., 1997, *J Neuroimmunol.* 72, 169). Atherosclerosis is known to have an inflammatory component and cytokines such as IL-1 and TNF have been suggested to promote the disease. In an animal model an IL-1 receptor antagonist was shown to inhibit fatty streak formation (Elhage et al., 1998, *Circulation*, 97, 242).

TNFα levels are elevated in airways of patients with chronic obstructive pulmonary disease and it may contribute to the pathogenesis of this disease (M. A. Higham et al., 2000, *Eur. Respiratory J.*, 15, 281). Circulating TNFα may also contribute to weight loss associated with this disease (N. Takabatake et al., 2000, *Amer. J. Resp. & Crit. Care Med.*, 161 (4 Pt 1), 1179). Elevated TNFα levels have also been found to be associated with congestive heart failure and the level has been correlated with severity of the disease (A. M. Feldman et al., 2000, *J. Amer. College of Cardiology*, 35, 537). In addition, TNFα has been implicated in reperfusion injury in lung (Borjesson et al., 2000, *Amer. J. Physiol.*, 278, L3-12), kidney (Lemay et al., 2000, *Transplantation*, 69, 959), and the nervous system (Mitsui et al., 1999, *Brain Res.*, 844, 192).

TNFα is also a potent osteoclastogenic agent and is involved in bone resorption and diseases involving bone resorption (Abu-Amer et al., 2000, *J. Biol. Chem.*, 275, 27307). It has also been found highly expressed in chondrocytes of patients with traumatic arthritis (Melchiorri et al., 2000, *Arthritis and Rheumatism*, 41, 2165). TNFα has also been shown to play a key role in the development of glomerulonephritis (Le Hir et al., 1998, *Laboratory Investigation*, 78, 1625).

The abnormal expression of inducible nitric oxide synthetase (iNOS) has been associated with hypertension in the spontaneously hypertensive rat (Chou et al., 1998, *Hypertension*, 31, 643). IL-1 has a role in the expression of iNOS and therefore may also have a role in the pathogenesis of hypertension (Singh et al., 1996, *Amer. J. Hypertension*, 9, 867).

IL-1 has also been shown to induce uveitis in rats which could be inhibited with IL-1 blockers. (Xuan et al., 1998, *J. Ocular Pharmacol. and Ther.*, 14, 31). Cytokines including IL-1, TNF and GM-CSF have been shown to stimulate proliferation of acute myelogenous leukemia blasts (Bruserud, 1996, *Leukemia Res.* 20, 65). IL-1 was shown to be essential for the development of both irritant and allergic contact dermatitis. Epicutaneous sensitization can be prevented by the administration of an anti-IL1 monoclonal antibody before epicutaneous application of an allergen (Muller, et al., 1996, *Am J Contact Dermat.* 7, 177). Data obtained from IL-1 knock out mice indicates the critical involvement in fever for this cytokine (Kluger et al., 1998, *Clin Exp Pharmacol Physiol.* 25, 141). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel, 1995, *Am J Clin Nutr.* 62, 813). The production of these inflammatory cytokines rapidly follows trauma or pathogenic organism invasion.

Other proinflammatory cytokines have been correlated with a variety of disease states. IL-8 correlates with influx of neutrophils into sites of inflammation or injury. Blocking antibodies against IL-8 have demonstrated a role for IL-8 in the neutrophil associated tissue injury in acute inflammation (Harada et al., 1996, *Molecular Medicine Today* 2, 482). Therefore, an inhibitor of IL-8 production may be useful in the treatment of diseases mediated predominantly by neutrophils such as stroke and myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, hemodialysis, leukopherisis, granulocyte transfusion associated syndromes, and necrotizing enterocolitis.

Rhinovirus triggers the production of various proinflammatory cytokines, predominantly IL-8, which results in symptomatic illnesses such as acute rhinitis (Winther et al., 1998, *Am J Rhinol.* 12, 17).

Other diseases that are effected by IL-8 include myocardial ischemia and reperfusion, inflammatory bowel disease and many others.

The proinflammatory cytokine IL-6 has been implicated with the acute phase response. IL-6 is a growth factor in a number in oncological diseases including multiple myeloma and related plasma cell dyscrasias (Treon, et al., 1998, *Current Opinion in Hematology* 5: 42). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol, et al., 1997, *Molecular Neurobiology* 15: 307). IL-6 also plays a significant role in osteoporosis. In murine models it has been shown to effect bone resorption and to induce osteoclast activity (Ershler et al., 1997, *Development and Comparative Immunol.* 21: 487). Marked cytokine differences, such as IL-6 levels, exist in vivo between osteoclasts of normal bone and bone from patients with Paget's disease (Mills, et al., 1997, *Calcif Tissue Int.* 61, 16). A number of cytokines have been shown to be involved in cancer cachexia. The severity of key parameters of cachexia can be reduced by treatment with anti IL-6 antibodies or with IL-6 receptor antagonists (Strassmann, et al., 1995, *Cytokins Mol Ther.* 1, 107). Several infectious diseases, such as influenza, indicate IL-6 and IFN alpha as key factors in both symptom formation and in host defense (Hayden, et al., 1998, *J Clin Invest.* 101, 643). Overexpression of IL-6 has been implicated in the pathology of a number of diseases including multiple myeloma, rheumatoid arthritis, Castleman's disease, psoriasis and post-menopausal osteoporosis (Simpson, et al., 1997, *Protein Sci.* 6, 929). Compounds that interfered with the production of cytokines including IL-6, and TNF were effective in blocking a passive cutaneous anaphylaxis in mice (Scholz et al., 1998, *J. Med. Chem.*, 41, 1050).

GM-CSF is another proinflammatory cytokine with relevance to a number of therapeutic diseases. It influences not only proliferation and differentiation of stem cells but also regulates several other cells involved in acute and chronic inflammation. Treatment with GM-CSF has been attempted in a number of disease states including burn-wound healing, skin-graft resolution as well as cytostatic and radiotherapy induced mucositis (Masucci, 1996, *Medical Oncology* 13: 149). GM-CSF also appears to play a role in the replication of human immunodeficiency virus (HIV) in cells of macrophage lineage with relevance to AIDS therapy (Crowe et al., 1997, *Journal of Leukocyte Biology* 62, 41). Bronchial asthma is characterised by an inflammatory process in lungs. Involved cytokines include GM-CSF amongst others (Lee, 1998, *J R Coll Physicians Lond* 32, 56).

Interferonγ (IFNγ) has been implicated in a number of diseases. It has been associated with increased collagen deposition that is a central histopathological feature of graft-versus-host disease (Parkman, 1998, *Curr Opin Hematol.* 5, 22). Following kidney transplantation, a patient was diagnosed with acute myelogenous leukemia. Retrospective analysis of peripheral blood cytokines revealed elevated levels of GM-CSF and IFNγ. These elevated levels coincided with a rise in peripheral blood white cell count (Burke, et al., 1995, *Leuk Lymphoma.* 19, 173). The development of insulin-dependent diabetes (Type 1) can be correlated with the accumulation in pancreatic islet cells of T-cells producing IFNγ (Ablumunits, et al., 1998, *J Autoimmun.* 11, 73). IFNγ along with TNF, IL-2 and IL-6 lead to the activation of most peripheral T-cells prior to the development of lesions in the central nervous system for diseases such as multiple sclerosis (MS) and AIDS dementia complex (Martino et al., 1998, *Ann Neurol.* 43, 340). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFNγ. These cytokines are thought to be involved in promoting apoptosis or programmed cell death of the surrounding vascular smooth muscle cells resulting in the atherosclerotic lesions (Geng, 1997, *Heart Vessels Suppl* 12, 76). Allergic subjects produce mRNA specific for IFNγ following challenge with Vespula venom (Bonay, et al., 1997, *Clin Exp Immunol.* 109, 342). The expression of a number of cytokines, including IFNγ has been shown to increase following a delayed type hypersensitivity reaction thus indicating a role for IFNγ in atopic dermatitis (Szepietowski, et al., 1997, *Br J Dermatol.* 137, 195). Histopathologic and immunohistologic studies were performed in cases of fatal cerebral malaria. Evidence for elevated IFNγ amongst other cytokines was observed indicating a role in this disease (Udomsangpetch et al., 1997, *Am J Trop Med Hyg.* 57, 501). The importance of free radical species in the pathogenesis of various infectious diseases has been established. The nitric oxide synthesis pathway is activated in response to infection with certain viruses via the induction of proinflammatory cytokines such as IFNγ (Akaike, et al., 1998, *Proc Soc Exp Biol Med.* 217, 64). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFNγ, TNF and IL-2 (Chisari, et al., 1995, *Springer Semin Immunopathol.* 17, 261). IFNγ can selectively inhibit cytokine induced bone resorption. It appears to do this via the intermediacy of nitric oxide (NO) which is an important regulatory molecule in bone remodeling. NO may be involved as a mediator of bone disease for such diseases as: rheumatoid arthritis, tumor associated osteolysis and postmenopausal osteoporosis (Evans, et al., 1996, *J Bone Miner Res.* 11, 300). Studies with gene deficient mice have demonstrated that the IL-12 dependent production of IFNγ is critical in the control of early parasitic growth. Although this process is independent of nitric oxide the control of chronic infection does appear to be NO dependent (Alexander et al., 1997, *Philos Trans R Soc Lond B Biol Sci* 352, 1355). NO is an important vasodilator and convincing evidence exists for its role in cardiovascular shock (Kilboum, et al., 1997, *Dis Mon.* 43, 277). IFNγ is required for progression of chronic intestinal inflammation in such diseases as Crohn's disease and inflammatory bowel disease (IBD) presumably through the intermediacy of CD4+ lymphocytes probably of the TH1 phenotype (Sartor 1996, *Aliment Pharmacol Ther.* 10 Suppl 2, 43). An elevated level of serum IgE is associated with various atopic diseases such as bronchial asthma and atopic dermatitis. The level of IFNγ was negatively correlated with serum IgE suggesting a role for IFNγ in atopic patients (Teramoto et al., 1998, *Clin Exp Allergy* 28, 74).

WO 01/01986 discloses particular compounds alleged to having the ability to inhibit TNF-alpha. Certain compounds disclosed in WO 01/01986 are indicated to be effective in treating the following diseases: dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalopathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia.

U.S. publication no. US 2003/0049660 discloses that inhibition of p38, which has a role in elevated levels of proinflammatory cytokines, is potentially a useful treatment for human breast cancer.

Compounds which modulate release of one or more of the aforementioned inflammatory cytokines can be useful in treating diseases associated with release of these cytokines. For example, WO 98/52558 discloses heteroaryl urea compounds which are indicated to be useful in treating cytokine mediated diseases. WO 99/23091 discloses another class of urea compounds which are useful as anti-inflammatory agents. WO 99/32463 relates to aryl ureas amd their use in treating cytokine diseases and proteolytic enzyme mediated disease. WO 00/41698 discloses aryl ureas said to be useful in treating p38 MAP kinase diseases.

U.S. Pat. No. 5,162,360 discloses N-substituted aryl-N'-heterocyclic substituted urea compounds which are described as being useful for treating hypercholesterolemia and atheroclerosis. Di-substituted aryl and heteroaryl compounds are also disclosed in U.S. Pat. Nos. 6,080,763; 6,319,921; 6,297,381 and 6,358,945. The compounds in the patents are alleged to possess anti-cytokine activity and are therefore useful in treating diseases associated with inflammation.

The work cited above supports the principle that inhibition of cytokine production will be beneficial in the treatment of cytokine mediated diseases. Therefore a need exists for small molecule inhibitors for treating these diseases with optimized efficacy, pharmacokinetic and safety profiles.

BRIEF SUMMARY OF THE INVENTION

The work cited above supports the principle that inhibition of cytokine production will be beneficial in the treatment of various disease states.

It is therefore an object of the invention to provide amide compounds of formula (I):

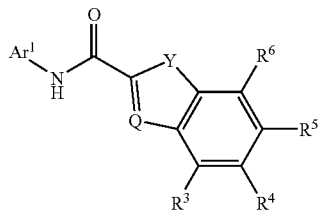

wherein $Ar^1$, Q, Y and $R^3$-$R^6$ of formula (I) are defined below, which inhibit the release of inflammatory cytokines such as interleukin-1 and tumor necrosis factor.

It is a further object of the invention to provide methods for treating cytokine mediated diseases and pathological conditions involving inflammation such as chronic inflammatory disease, using the novel compounds of the invention.

It is yet a further object of the invention to provide processes of preparation of the above-mentioned novel compounds.

DETAILED DESCRIPTION OF THE INVENTION

In the broadest generic aspect of the invention, there are provided compounds of the formula (I):

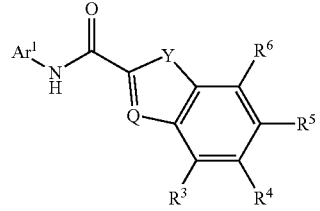

Q is a nitrogen or $CR^p$ $CR^v$;

Y is $CR^pR^v$, $CR^pCR^v$, O, N—$R^x$ or $S(O)_n$;

wherein $R^p$, $R^v$ and $R^x$ are hydrogen or C1-5 alkyl;

$Ar^1$ is carbocycle optionally substituted with one $R^1$, and wherein $Ar^1$ is independently substituted with two $R^2$ groups;

$R^1NO_2$, —$N(R^a)_2$ or the formula:

$$J-M_1-M_2- \text{ wherein:}$$

one of $M_1$ and $M_2$ is $S(O)_m$ and the other is N—$R^a$,

J is chosen from C1-10 alkyl and carbocycle each optionally substituted by $R^b$;

$R^2$ is independently chosen from C1-6 alkyl or C3-7 cycloalkyl which may optionally be partially or fully halogenated, C1-4 acyl, aroyl, C1-4 alkoxy, which may optionally be partially or fully halogenated, halogen, C1-6 alkoxycarbonyl, carbocyclesulfonyl and —$SO_2$—$CF_3$;

each $R^4$ and $R^5$ are independently chosen from hydrogen, C1-6 alkyl and halogen;

each $R^3$ and $R^6$ are independently hydrogen, C1-5 alkyl, C2-5 alkenyl, C2-5 alkynyl, C1-5 alkoxy, C1-5 alkylthio, amino, C1-5 alkylamino, C1-5 dialkylamino, C1-5 acyl, C1-5 alkoxycarbonyl, C1-5 acyloxy, C1-5 acylamino, each of the aforementioned are optionally partially or fully halogenated, C1-5 alkylsulphonylamino, hydroxy, halogen, nitrile, carbocycleC0-6 alkyl, heteroarylC0-6alkyl, heterocyclylC0-6alkyl each carbocycle, hetaryl or heterocyclyl optionally substituted with $R^c$, or one of $R^3$ or $R^6$ is the formulas (II) or (III):

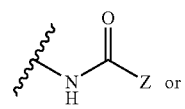

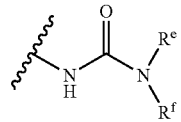

wherein Z is chosen from aryl, C3-7 cycloalkyl, cyclohexanone, heterocycle chosen from pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, 1-oxo-λA-thiomorpholinyl, 13-oxa-11-aza-tricyclo[7.3.1.0-2,7]trideca-2,4,6-triene, tetrahydropyranyl, 2-oxo-2H-pyranyl, tetrahydrofuranyl, 1,3-dioxolanone, 1,3-dioxanone, 1,4-dioxanyl, 8-oxa-3-aza-bicyclo[3.2.1]octanyl, 2-oxa-5-aza-bicyclo[2.2.1]heptanyl, 2-thia-5-aza-bicyclo[2.2.1]heptanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone or heteroaryl chosen from aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl, each optionally substituted by one to three $R^d$;

$R^e$ and $R^f$ are independently chosen from hydrogen, C1-5 alkyl and Z, the Z is optionally substituted by one to three $R^d$;

$R^a$, $R^b$ and $R^c$ are each independently chosen from hydrogen, C1-5 alkyl, C2-5 alkenyl, C2-5 alkynyl, carbocycle, C1-5 alkoxy, C1-5 alkylthio, amino, C1-5 alkylamino, C1-5 dialkylamino, C1-5 acyl, C1-5 alkoxycarbonyl, C1-5 acyloxy, C1-5 acylamino, each of the aforementioned are optionally partially or fully halogenated, or $R^a$, $R^b$ and $R^C$ are chosen from C1-5 alkylsulphonylamino, hydroxy, halogen, nitro and nitrile;

$R^d$ is as defined for $R^a$, $R^b$ and $R^c$ above, aminoacyl or amino wherein for each the N atom is mono- or di-substituted by C1-4 alkyl, aminoC1-3 acyl, arylC0-3 alkyl, C3-7cycloalkylC0-3 alkyl, heteroarylC0-3 alkyl, heterocyclylC0-3 alkyl, C1-5 alkylC1-5alkoxy or C1-4alkylamino-mono-or-di-substituted by C1-3alkyl, or $R^d$ is

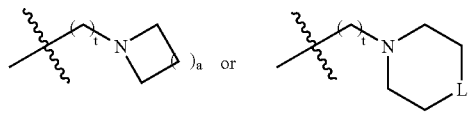

wherein a and t are independently 1, 2 or 3 and L is a heteroatom chosen from N, O and S, or $R^d$ is $Ar^3$—C(O)— and $Ar^3$—S(O)$_m$— wherein is Ar is chosen from carbocycle, heterocyclyl and heteroaryl, each carbocycle, heterocyclyl and heteroaryl in this paragraph for $R^d$ or $Ar^3$ are optionally substituted by one to two C1-5 alkyl, C1-5 alkoxy, C1-5 alkoxycarbonyl or halogen;

n is 0, 1 or 2 and m is 0, 1 or 2;

or the pharmaceutically acceptable acids and salts or isomers thereof with the proviso that:

if $R^1$ is not present then one of $R^3$ or $R^6$ must be the formulas (II) or (III), or if one of $R^3$ or $R^6$ is nitro then $R^1$ must be present.

A second subgeneric embodiment of the invention comprises compounds of the formula (I), as described in the broadest generic aspect, and wherein:

Q is $CH_2$;

Y is CH=CN, N—$R^x$ or S(O)$_n$;

J is chosen from C1-10 alkyl, aryl or C3-7 cycloalkyl each optionally substituted by $R^b$;

$R^2$ is independently chosen from C1-6 alkyl which may optionally be partially or fully halogenated, acetyl, aroyl, C1-4 alkoxy, which may optionally be partially or fully halogenated, halogen, methoxycarbonyl, phenylsulfonyl and —$SO_2$—$CF_3$;

each $R^4$ and $R^5$ are independently chosen from hydrogen, C1-C4 alkyl, F, Cl and Br;

each $R^3$ and $R^6$ are independently hydrogen, C1-5 alkyl, C2-5 alkenyl, C2-5 alkynyl, C3-8 cycloalkyl, C1-5 alkoxy, C1-5 alkylthio, amino, C1-5 alkylamino, C1-5 dialkylamino, C1-5 acyl, C1-5 alkoxycarbonyl, C1-5 acyloxy, C1-5 acylamino, each of the aforementioned are optionally partially or fully halogenated, C1-5 alkylsulphonylamino, hydroxy, halogen, trifluoromethyl, nitrile, arylC0-6 alkyl, heteroarylC0-6 alkyl wherein the heteroaryl is chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl and indazolyl, cycloalkylC0-6 alkyl or heterocyclylC0-6 alkyl wherein the heterocyclyl is chosen from pyrrolidinyl, pyrrolinyl, morpholinyl, thiomorpholinyl, dioxalanyl, piperidinyl, piperazinyl, aziridinyl and tetrahydrofuranyl, each of the above $R^3$ or $R^6$ optionally substituted with $R^c$, or one of $R^3$ or $R^6$ is the formulas (II) or (III):

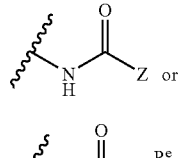

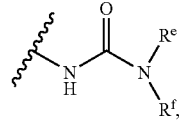

wherein Z is chosen from aryl, C3-7 cycloalkyl, heterocycle chosen from pyrrolidinyl, pyrrolinyl, morpholinyl, thiomorpholinyl, dioxalanyl, piperidinyl, piperazinyl, aziridinyl and tetrahydrofuranyl or heteroaryl chosen from thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl and indazolyl, each Z optionally substituted by one to two $R^d$;

$R^a$, $R^b$ and $R^c$ are each independently chosen from hydrogen, C1-5 alkyl, C2-5 alkenyl, C2-5 alkynyl, C3-8 cycloalkylC0-2 alkyl, aryl, C1-5 alkoxy, C1-5 alkylthio, amino, C1-5 alkylamino, C1-5 dialkylamino, C1-5 acyl, C1-5 alkoxycarbonyl, C1-5 acyloxy, C1-5 acylamino, or $R^a$, $R^b$ and $R^c$ are chosen from C1-5 sulphonylamino, hydroxy, halogen, trifluoromethyl, nitro and nitrile;

$R^d$ is as defined for $R^a$, $R^b$ and $R^c$ above, aminoacyl or amino wherein for each the N atom is mono- or di-substituted by C1-4 alkyl, aminoC1-3 acyl, arylC0-3 alkyl, C3-7 cycloalkylC0-3 alkyl, heteroarylC0-3 alkyl, heterocyclylC0-3 alkyl, C1-5alkylC1-5alkoxy or C1-4alkylamino-mono-or-di-substituted by C1-3alkyl, $Ar^3$—C(O)— and $Ar^3$—S(O)$_m$— wherein $Ar^3$ is heterocyclyl, each aryl, heterocyclyl and heteroaryl in this paragraph for $R^d$ or $Ar^3$ are optionally substituted by one to two C1-5 alkyl, C1-5 alkoxy, C1-5 alkoxycarbonyl or halogen; and n is 0.

A third subgeneric embodiment of the invention comprises compounds of the formula (I), as described in the immediate previous embodiment, wherein:

$Ar^1$ is chosen from cyclopropyl, cyclobutyl, cyclopentyl, cyclohexyl and cycloheptyl, phenyl, naphthyl, tetrahydronaphthyl, indanyl and indenyl, each Ar¹ is substituted with one R¹, and independently substituted with two R² groups;

R¹ is NO₂, NH₂, C1-3acylNH— or the formula:

J—S(O)ₘ—N(Rᵃ)—;

J is C1-10 alkyl;

R² is independently chosen from C1-6 alkyl which may optionally be partially or fully halogenated and C1-3 alkoxy, which may optionally be partially or fully halogenated;

each R³ and R⁶ are independently hydrogen, C1-5 alkyl, amino, C1-5 alkylamino, C1-5 dialkylamino, C1-5 acylamino, each of the aforementioned are optionally partially or fully halogenated, C1-5 alkylsulphonylamino, halogen, nitro, nitrile, or one of R³ or R⁶ is the formulas (II) or (III):

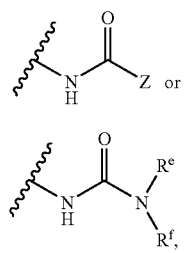

(II)

(III)

wherein Z is chosen from phenyl, C3-7 cycloalkyl, morpholinyl, thiomorpholinyl, thienyl, furanyl, pyridinyl, pyrimidinyl, pyrazinyl, pyridazinyl, quinoxalinyl, quinolinyl, and quinazolinyl, each Z optionally substituted by one to two Rᵈ, Rᵉ and Rᶠ are independently hydrogen or C1-3 alkyl, and m is 2.

A fourth subgeneric embodiment of the invention comprises compounds of the formula (I), as described in the immediate previous embodiment, wherein:

Y is CH=CH, N—CH₃, N—CH₂—CH₃, N—CH₂CH₂CH₃ or S;

Ar¹ is

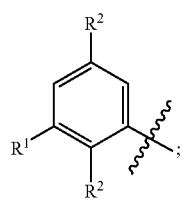

R¹ is the formula:

J—S(O)₂—NH—;

J is C1-5 alkyl;

R² is independently chosen from C1-5 alkyl which may optionally be partially or fully halogenated and C1-2 alkoxy, which may optionally be partially or fully halogenated;

each R⁴ and R⁵ are hydrogen;

each R³ and R⁶ are independently hydrogen, C1-5 acylamino optionally partially or fully halogenated, halogen, nitro, or one of R³ or R⁶ is the formulas (II) or (III):

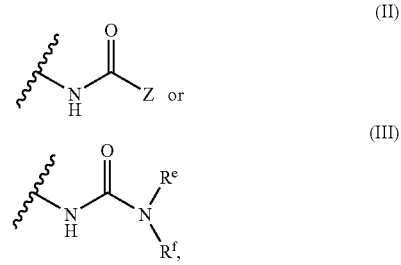

(II)

(III)

wherein Z is chosen from phenyl, cyclopropyl, morpholinyl, furanyl, pyridinyl, pyrimidinyl, pyrazinyl and quinoxalinyl, each Z is optionally substituted by one to two Rᵈ;

and

Rᵈ is chosen from

C1-5 alkyl, C3-6 cycloalkylC0-2 alkyl, aryl, C1-5 alkoxy, amino, C1-5 alkylamino, C1-5 dialkylamino, C1-5 acylamino, halogen, trifluoromethyl, nitro, nitrile, aminoacyl or amino wherein for each the N atom is mono- or di-substituted by C1-3 alkyl, aminoC1-2 acyl, phenylC0-3 alkyl, C3-6cycloalkylC0-2 alkyl, C1-5alkylC1-5alkoxy or C1-3 alkylN(C1-3alkyl)₂, Ar³—C(O)— and Ar³—S(O)ₘ— wherein Ar³ is heterocyclyl chosen from pyrrolidinyl, pyrrolinyl, morpholinyl, thiomorpholinyl, dioxalanyl, piperidinyl, piperazinyl, aziridinyl and tetrahydrofuranyl, each phenyl, heterocyclyl and heteroaryl in this paragraph for Rᵈ or Ar³ are optionally substituted by one to two C1-5 alkyl, C1-5 alkoxy, C1-5 alkoxycarbonyl or halogen.

A fifth subgeneric embodiment of the invention comprises compounds of the formula (I), as described in the immediate previous embodiment, wherein:

Y is N—CH₃ or S;

J is C1-3 alkyl;

R² is independently chosen from C1-5 alkyl which may optionally be partially or fully halogenated and C1-2 alkoxy, which may optionally be partially or fully halogenated;

each R³ and R⁶ are independently hydrogen, C1-5 acylamino optionally partially or fully halogenated, halogen, nitro, or one of R³ or R⁶ is the formula (II)

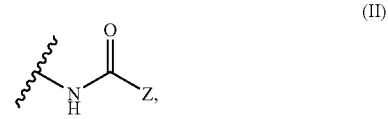

(II)

wherein Z is chosen from phenyl, cyclopropyl, morpholinyl, furanyl, pyridinyl, pyrimidinyl, pyrazinyl and quinoxalinyl, each Z optionally substituted by one to two $R^d$; and $R^d$ is chosen from C1-3 alkyl, methoxy, amino, F, Cl, nitro, aminoacyl or amino wherein for each the N atom is mono- or di-substituted by C1-3alkyl, aminoC1acyl, benzyl, cyclopropyl, cyclopropylmethyl, cyclohexylmethyl, C1-3alkylC1-3alkoxy or C1-3 alkylN(C1-2 alkyl)$_2$, $Ar^3$—C(O)— and $Ar^3$—S(O)$_m$— wherein $Ar^3$ is heterocyclyl chosen from morpholinyl and piperazinyl, each phenyl group and heterocyclyl in this paragraph for $R^d$ or $Ar^3$ are optionally substituted by one to two C1-3 alkyl, C1-3 alkoxy, C1-5 alkoxycarbonyl or halogen.

In another embodiment, there are provided compounds of the formula (I), as described in the immediate previous embodiment, wherein:

Y is N—CH$_3$;

$Ar^1$ is

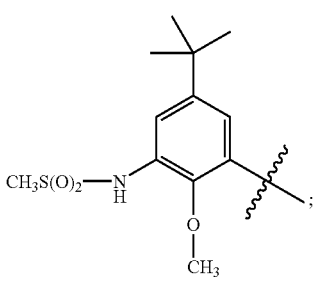

and $R^d$ is morpholinyl-C(O)—.

In another embodiment, there are provided compounds of the formula (I), as described in the fifth subgeneric embodiment of the invention and wherein:

Y is S;

$Ar^1$ is

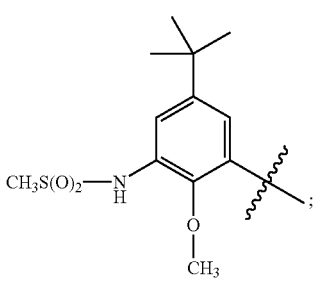

$R^d$ is chosen from methyl, methoxy, amino, F, Cl, nitro,

CH$_3$NHCO—, (CH$_3$)$_2$NCO—, CH$_3$NH—, (CH$_3$)$_2$N(CH$_2$)$_3$NH—, cyclopropyl-NH—, cyclopropylmethyl-NH—, cyclohexylmethyl-NH—, CH$_3$OCH$_2$CH$_2$NH—, (CH$_3$)$_2$NCO—NH—, and $Ar^3$—S(O)$_m$— wherein $Ar^3$ is morpholinyl optionally substituted by C1-5 alkoxycarbonyl.

In another embodiment, there are provided compounds of the formula (I), as described in the fourth subgeneric embodiment of the invention and wherein:

one of $R^3$ or $R^6$ is the formula (III):

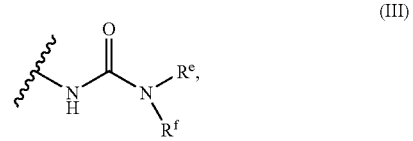

(III)

$R^e$ and $R^f$ are chosen from methyl and ethyl, and $Ar^1$ is

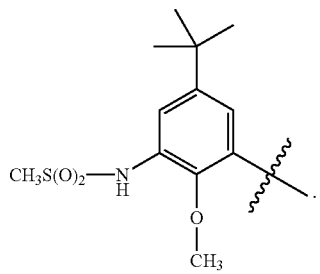

In another embodiment, there are provided compounds of the formula (I), as described in the second subgeneric embodiment of the invention and wherein:

$R^1$ is not present;

Y is or N—C1-5 alkyl;

$Ar^1$ is chosen from cyclopropyl, cyclobutyl, cyclopentyl, cyclohexyl and cycloheptyl, phenyl, naphthyl, tetrahydronaphthyl, indanyl and indenyl, each $Ar^1$ is independently substituted with two $R^2$ groups;

$R^2$ is independently chosen from C3-6 alkyl which may optionally be partially or fully halogenated, C1-4 alkoxy, which may optionally be partially or fully halogenated;

one of $R^3$ or $R^6$ is the formula (II):

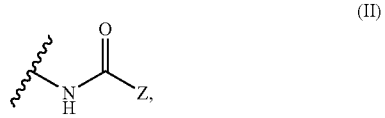

(II)

wherein Z is chosen from phenyl, C3-7 cycloalkyl, morpholinyl, thiomorpholinyl, thienyl, furanyl, pyridinyl, pyrimidinyl, pyrazinyl, pyridazinyl, quinoxalinyl, quinolinyl, and quinazolinyl.

In another embodiment, there are provided compounds of the formula (I), as described in the immediate previous embodiment, wherein:

Y is S or N—CH$_3$;

$Ar^1$ is

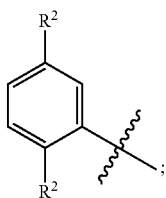

$R^2$ is independently chosen from C3-5 alkyl which may optionally be partially or fully halogenated and C1-4 alkoxy, which may optionally be partially or fully halogenated;

each $R^4$ and $R^5$ are hydrogen;

Z is chosen from phenyl, cyclopropyl, morpholinyl, furanyl, pyridinyl, pyrimidinyl, pyrazinyl and quinoxalinyl.

In another embodiment, there are provided compounds of the formula (I), as described in the immediate previous embodiment, wherein:

$R^2$ is independently chosen from C4-5 alkyl which may optionally be partially or fully halogenated and C1-3 alkoxy, which may optionally be partially or fully halogenated;

Z is chosen from phenyl, cyclopropyl, morpholinyl, furanyl, pyridinyl, pyrimidinyl, pyrazinyl and quinoxalinyl.

In another embodiment, there are provided compounds of the formula (I), as described in the immediate previous embodiment, wherein Z is pyridinyl.

The following compounds are representative of the compounds of formula (I) where $R^1$ is present:

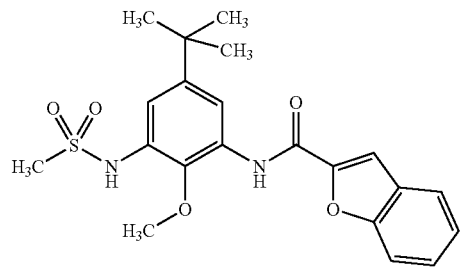

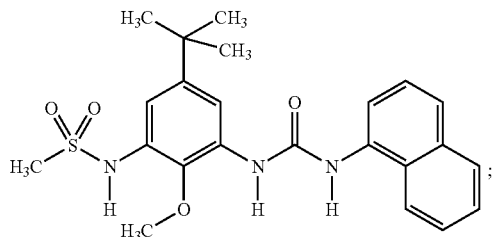

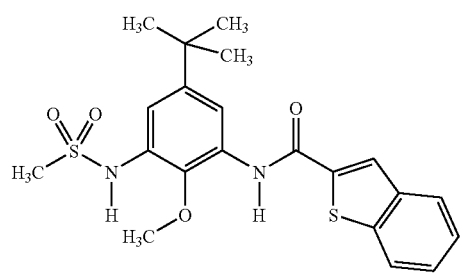

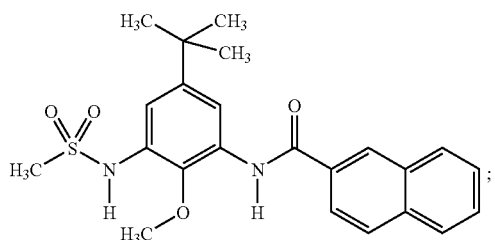

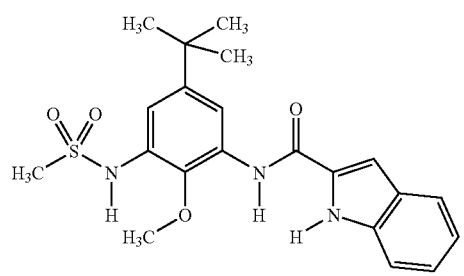

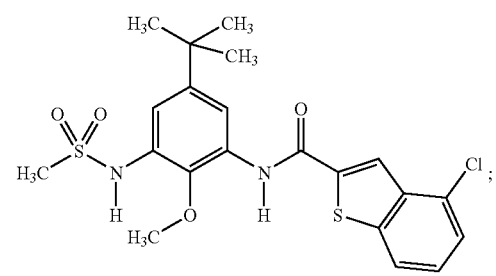

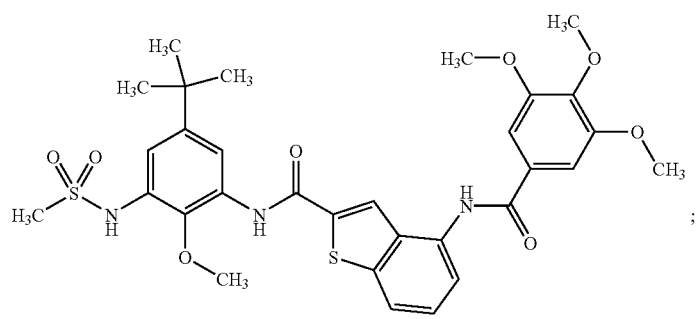

-continued
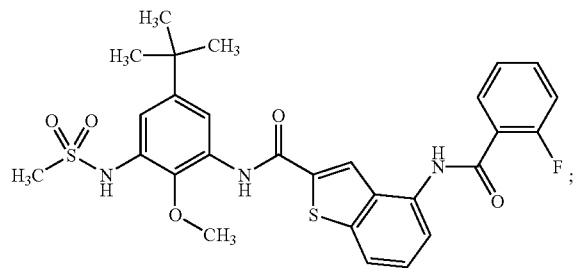
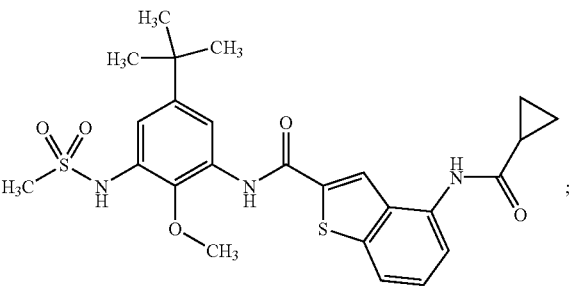
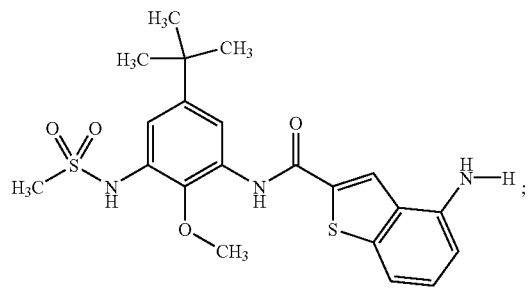
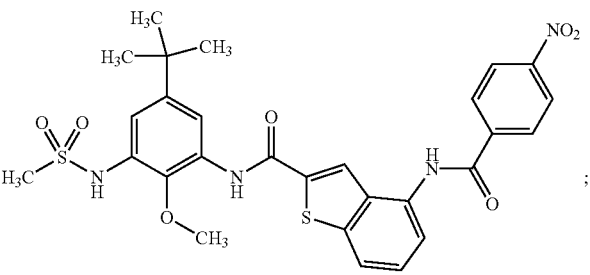
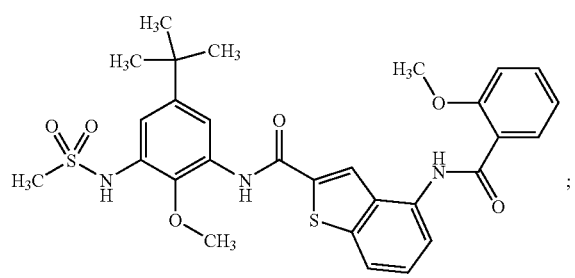
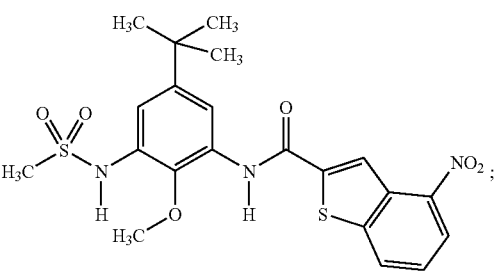
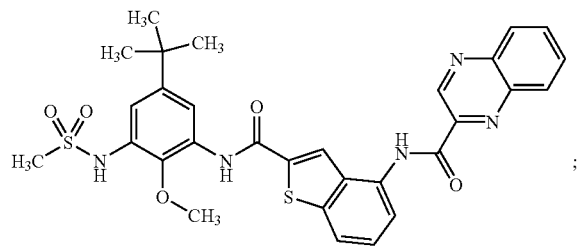
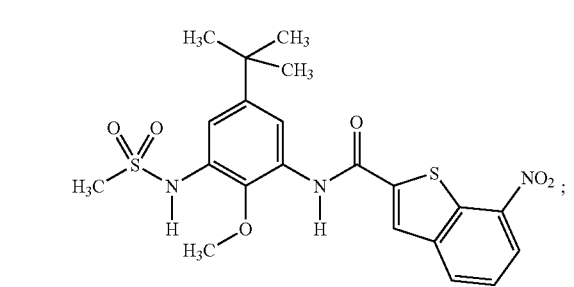
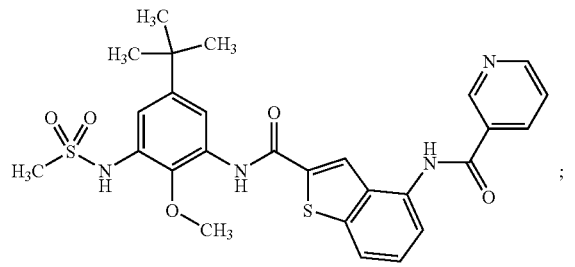
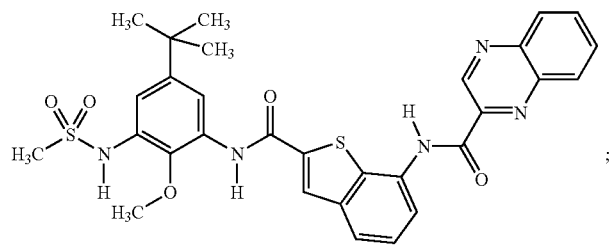
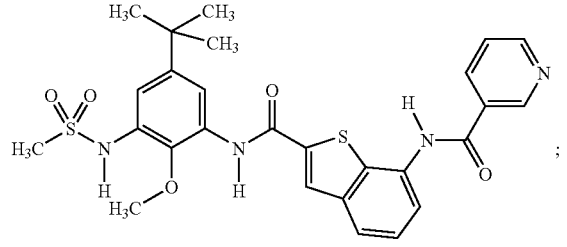
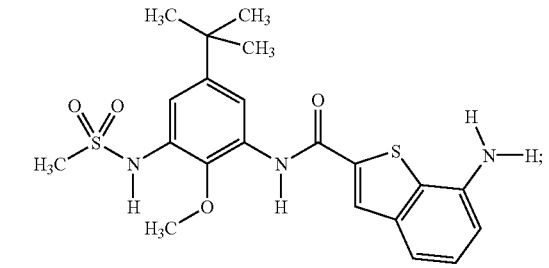

-continued
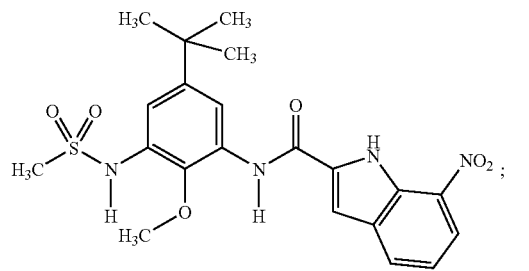
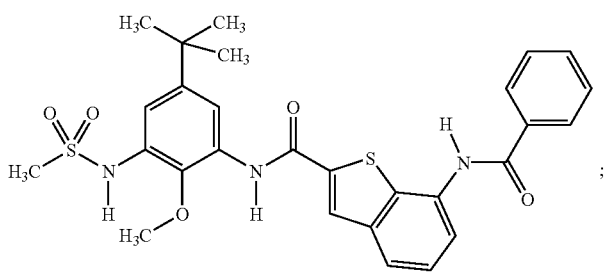
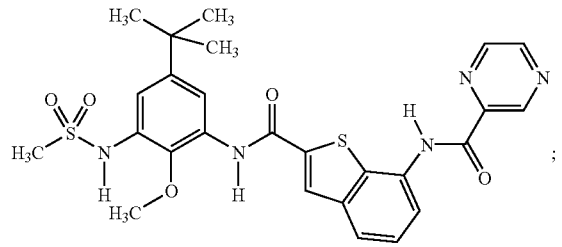
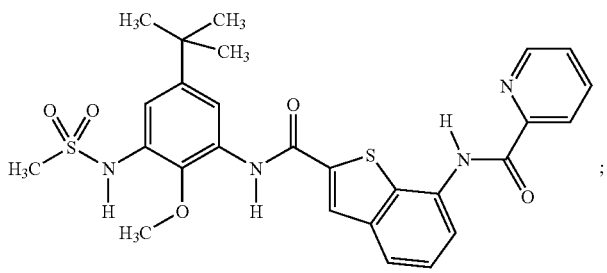
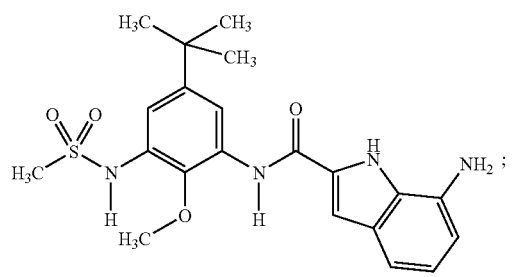
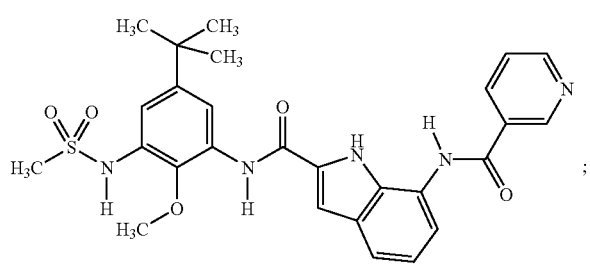
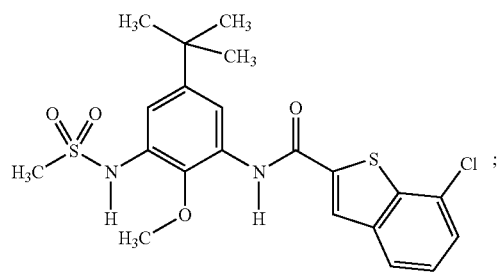
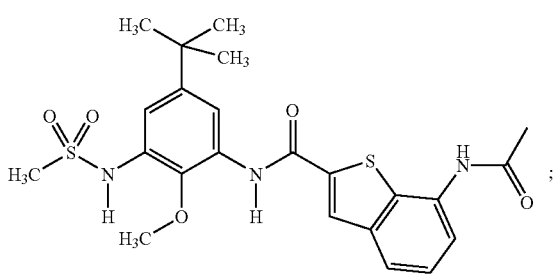
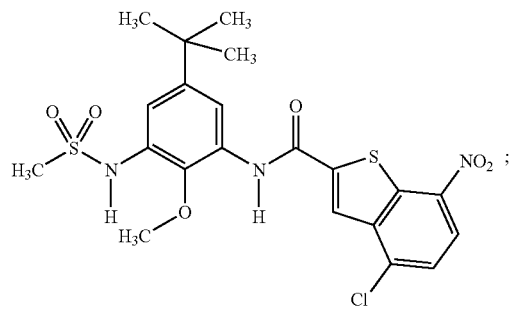
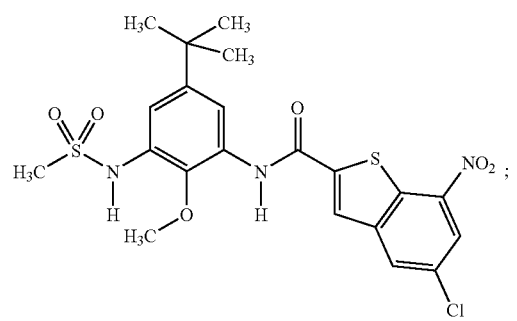
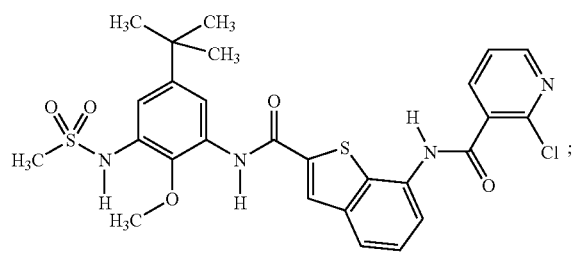
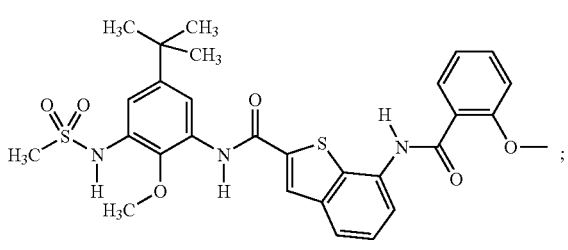

-continued
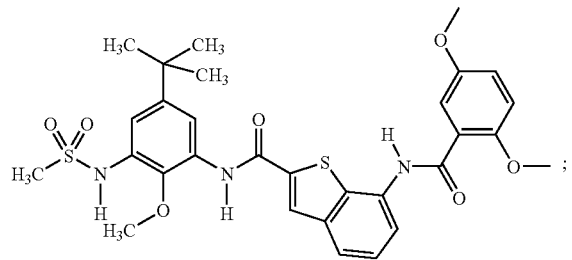
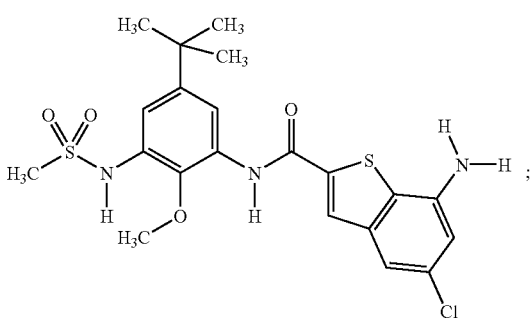
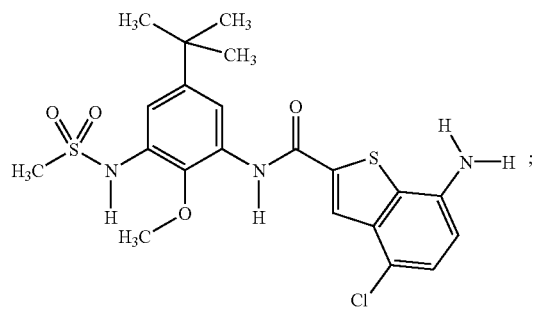
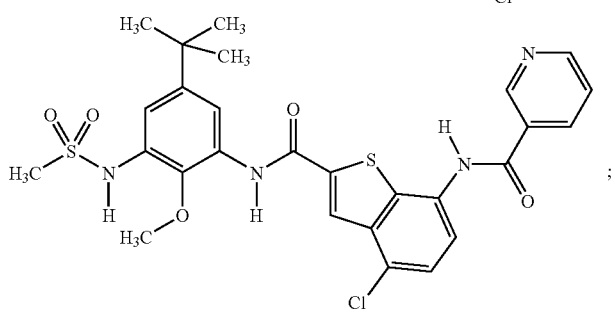
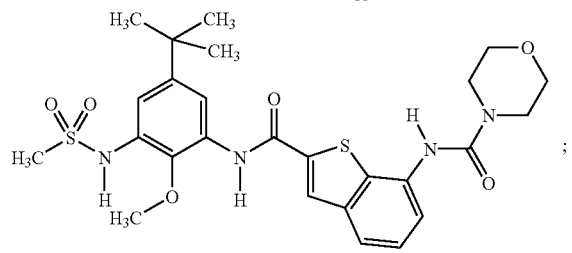
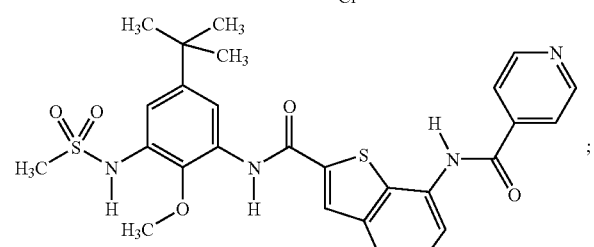
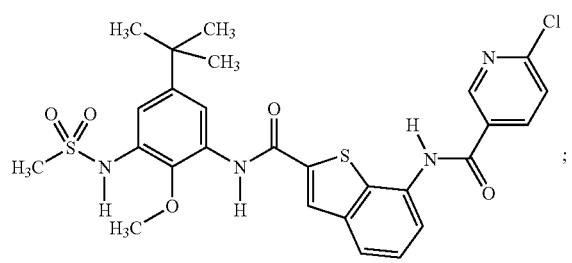
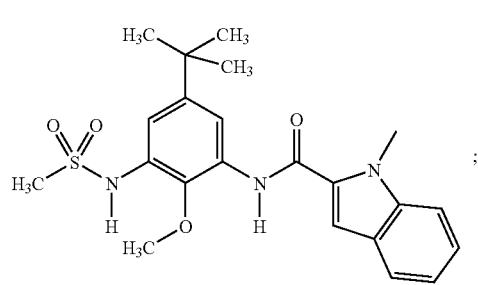
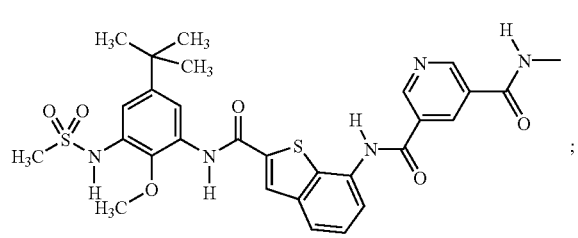
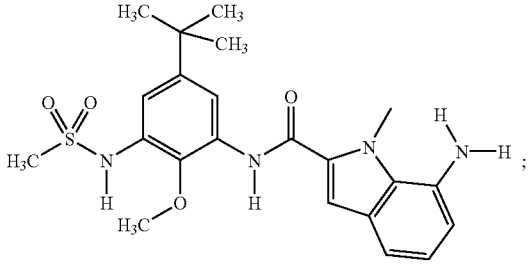
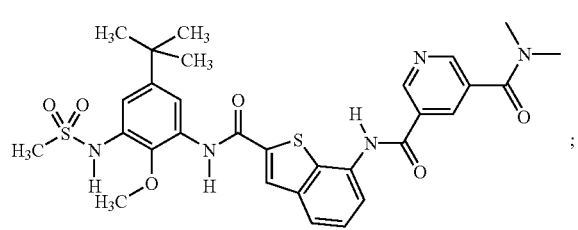
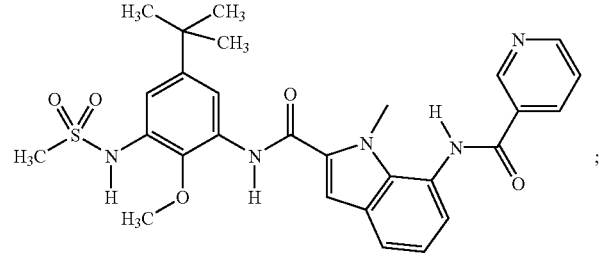

-continued
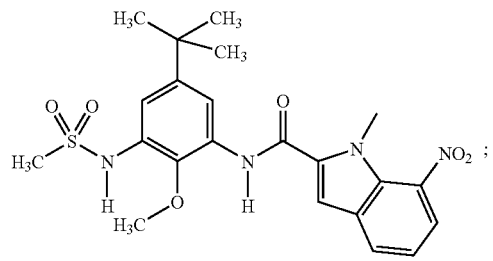
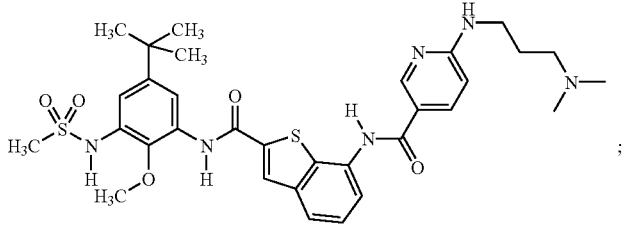
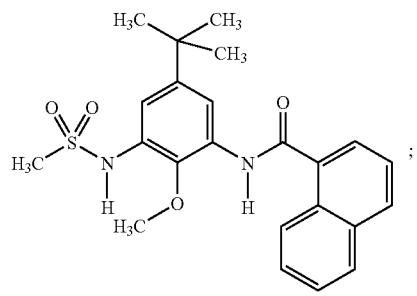
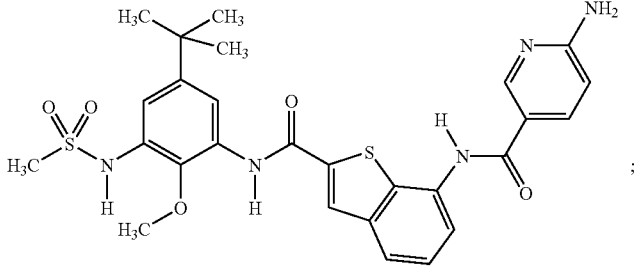
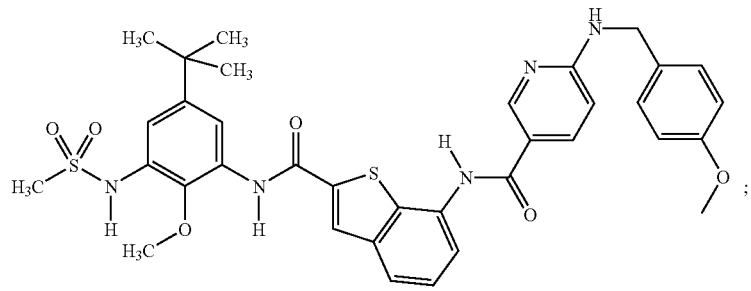
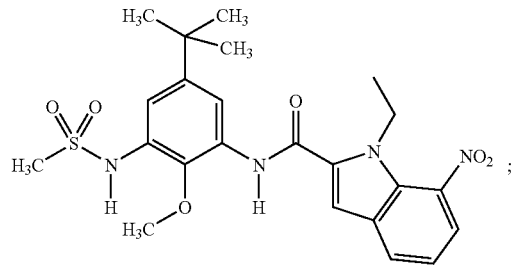
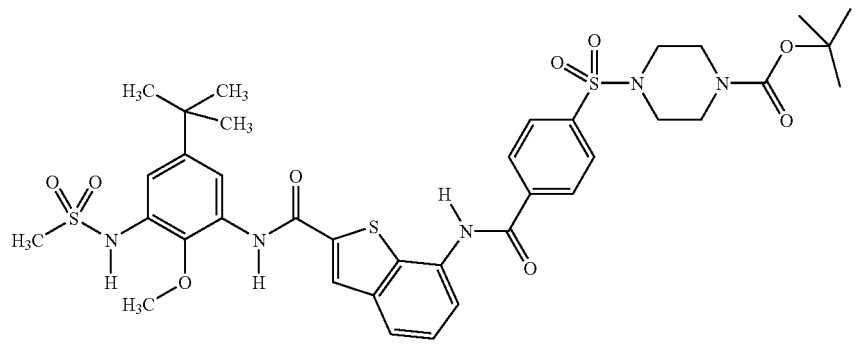
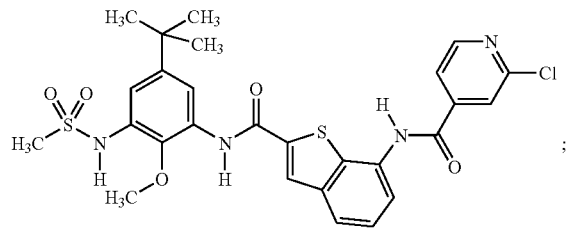
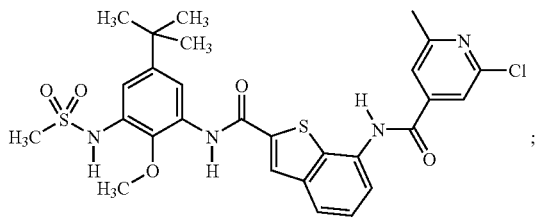

-continued
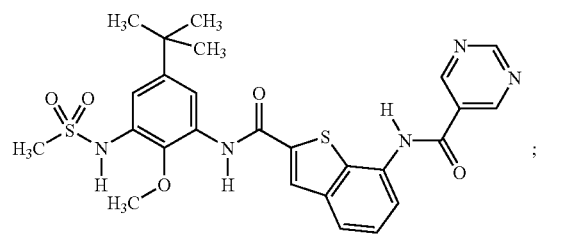
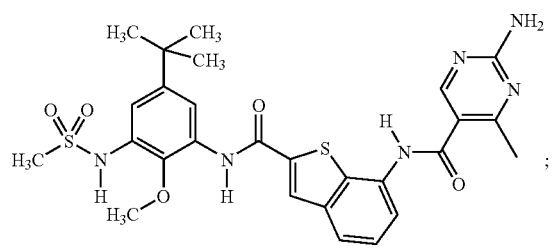
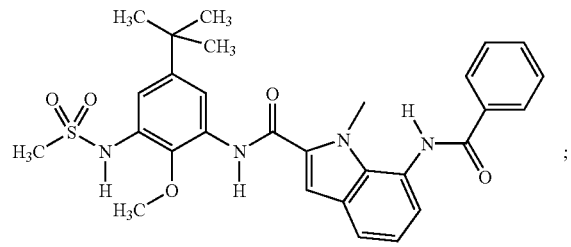
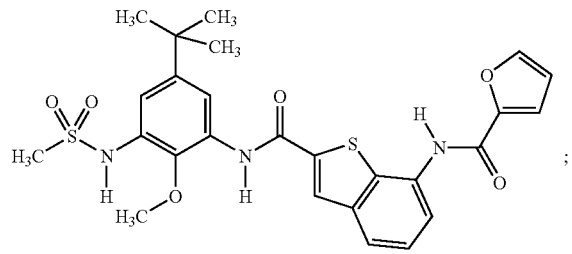
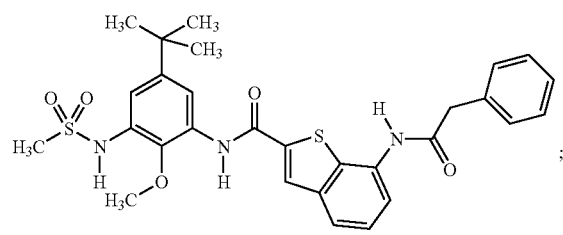
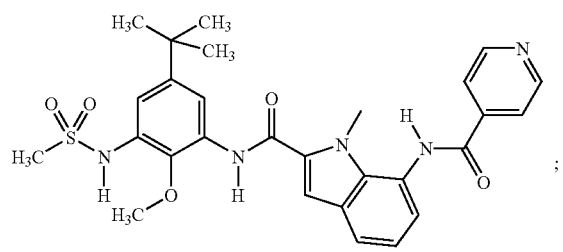
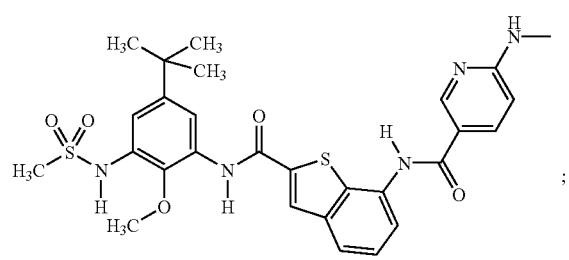
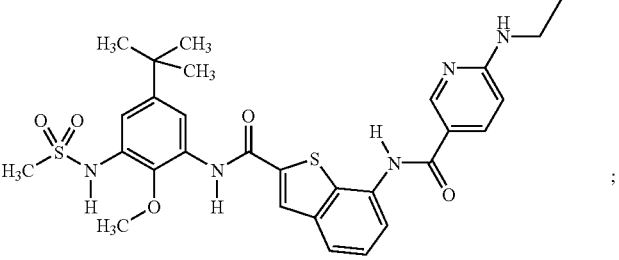
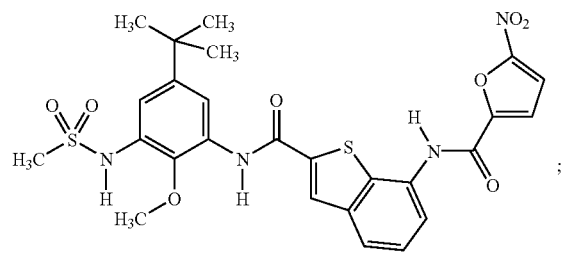
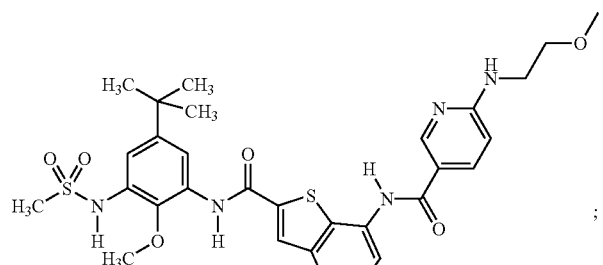
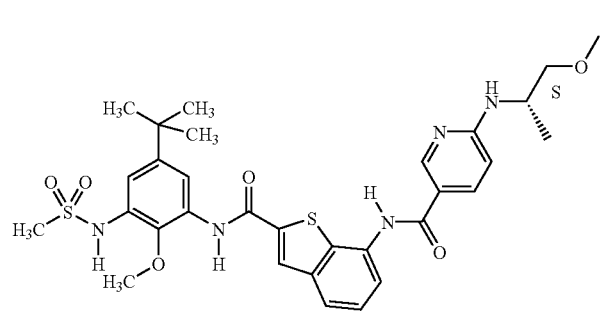
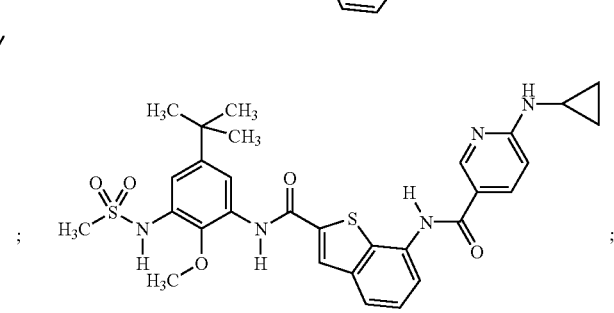

-continued
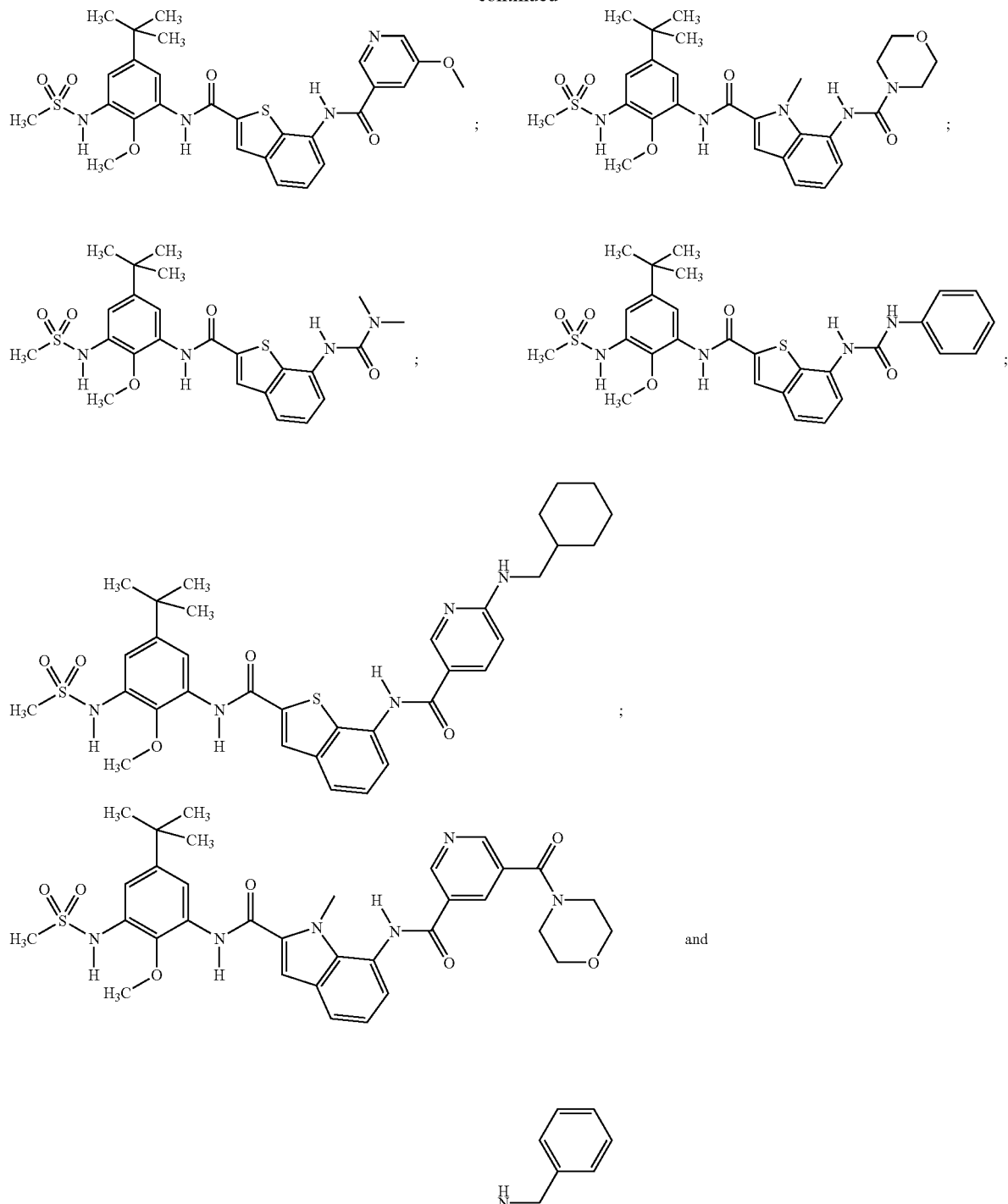
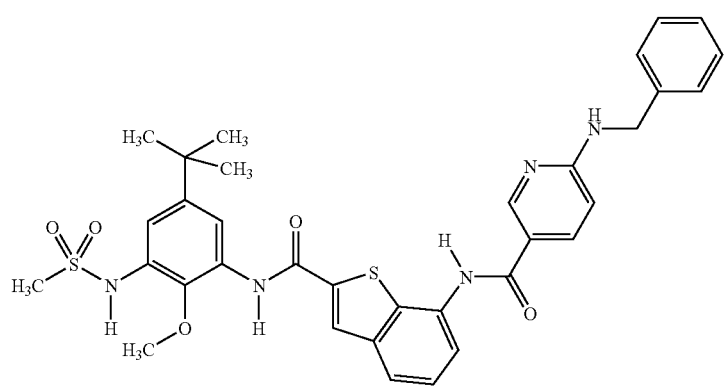

or the pharmaceutically acceptable acids and salts or isomers thereof.
The following are also representative compounds of the invention:
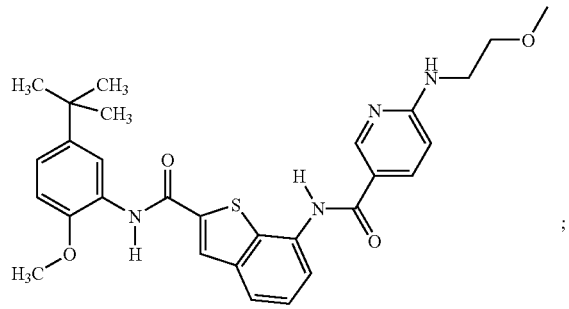
;
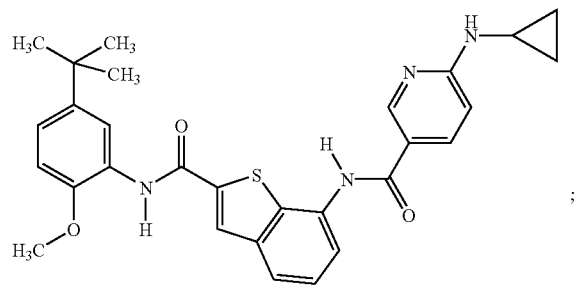
;
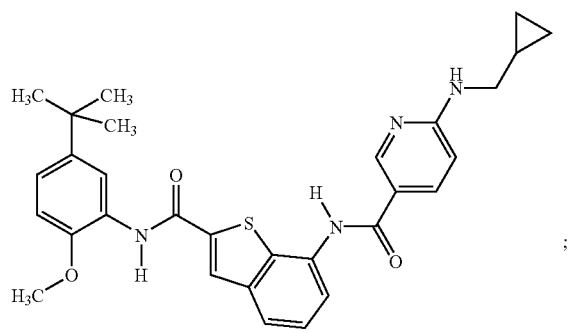
;
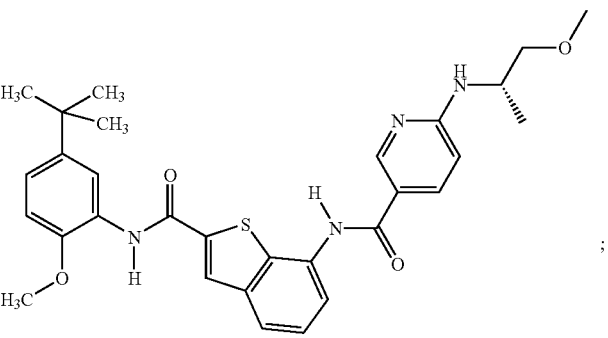
;
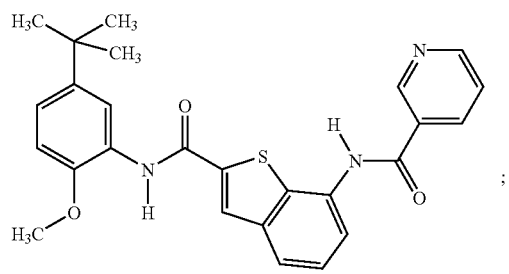
;
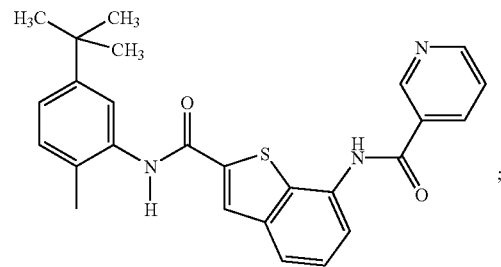
;
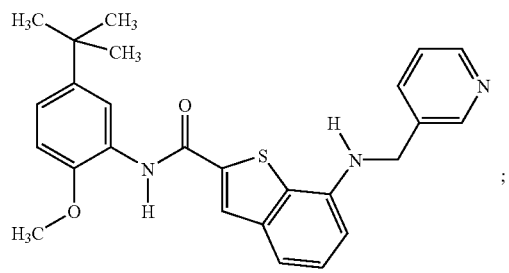
;
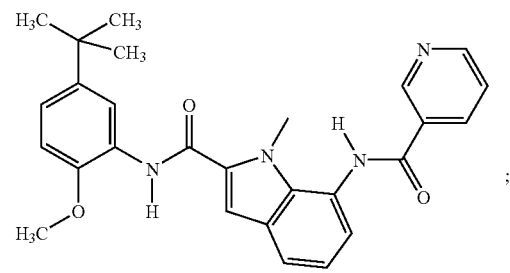
;
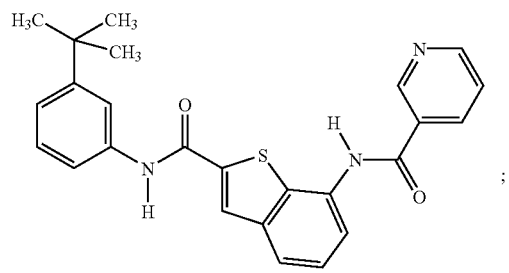
;
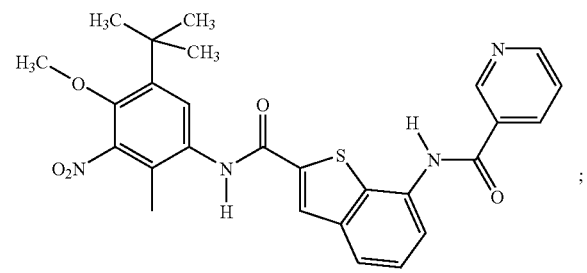
;

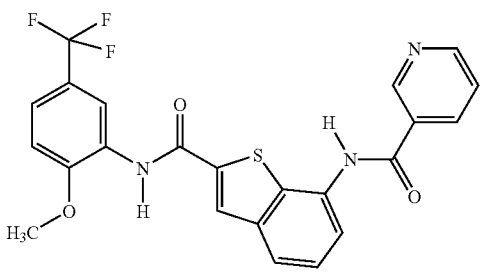

and or the pharmaceutically acceptable acids and salts or isomers thereof.

In an additional embodiment there is provided the following compounds:

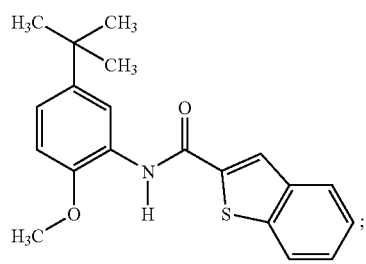

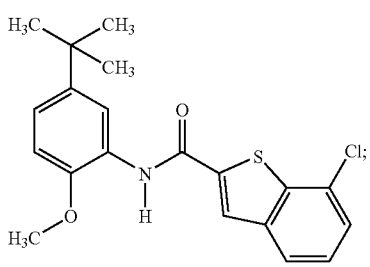

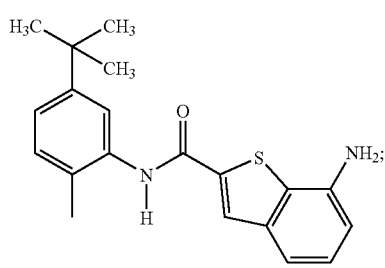

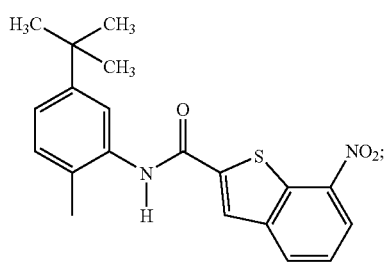

-continued

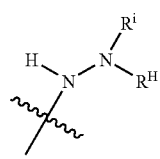

and or the pharmaceutically acceptable acids and salts or isomers thereof.

In another embodiment there is provided compounds as described in the broadest generic aspect of the invention, and wherein $R^d$ is a hydrazone represented by the formula:

wherein $R^H$ and $R^i$ are independently chosen from hydrogen, C1-5 alkyl and optionally substituted cycloalkyl, aryl, heteroaryl and heterocycle.

Representative compounds where $R^d$ is the above described hydrazone can be made as described in the general and specific examples, and include:

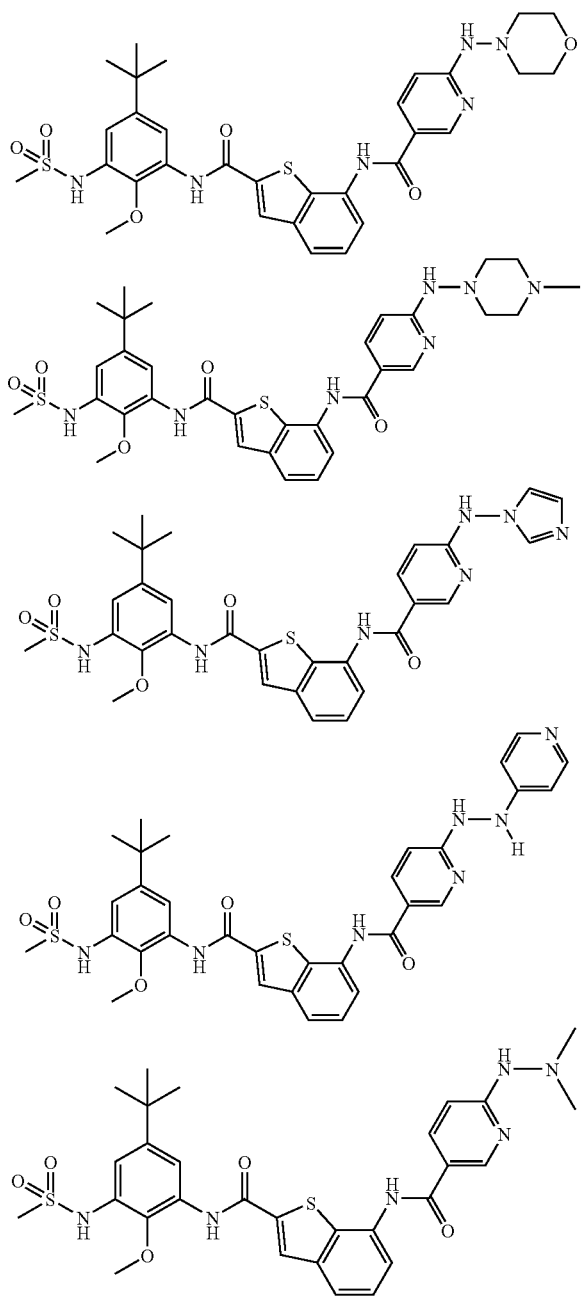

In all the compounds disclosed hereinabove in this application, in the event the nomenclature is in conflict with the structure, it shall be understood that the compound is defined by the structure.

The invention includes the use of any compounds of described above containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

The term "aroyl" as used in the present specification shall be understood to mean "benzoyl" or "naphthoyl".

The term "carbocycle" shall be understood to mean an aliphatic hydrocarbon radical containing from three to twelve carbon atoms. Carbocycles include hydrocarbon rings containing from three to ten carbon atoms. These carbocycles may be either aromatic and non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used inerchangeably.

The term "heterocycle" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, 1-oxo-λ4-thiomorpholinyl, 13-oxa-11-aza-tricyclo[7.3.1.0-2,7]trideca-2,4,6-triene, tetrahydropyranyl, 2-oxo-2H-pyranyl, tetrahydrofuranyl, 1,3-dioxolanone, 1,3-dioxanone, 1,4-dioxanyl, 8-oxa-3-aza-bicyclo[3.2.1]octanyl, 2-oxa-5-aza-bicyclo[2.2.1]heptanyl, 2-thia-5-aza-bicyclo[2.2.1]heptanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5-8 membered monocyclic or 8-11 membered bicyclic ring containing 1-4 heteroatoms such as N, O and S. Unless otherwise stated, such heteroaryls include aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

Terms which are analogs of the above cyclic moieties such as aryloxy or heteroaryl amine shall be understood to mean an aryl, heteroaryl, heterocycle as defined above attached to it's respective group.

As used herein, "nitrogen" and "sulfur" include any oxidized form of nitrogen and sulfur and the quaternized form of any basic nitrogen For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine. The definitions "partially or fully halogenated" "substituted by one or more halogen atoms" includes for example, mono, di or tri halo derivatives on one or more carbon atoms. For alkyl, a nonlimiting example would be —$CH_2CHF_2$, —$CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

Methods of Use

In accordance with the invention, there are provided novel methods of using the compounds of the formula (I). The compounds disclosed therein effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds are useful for the treatment of the following conditions and diseases:

osteoarthritis, atherosclerosis, contact dermatitis, bone resorption diseases, reperfusion injury, asthma, multiple sclerosis, Guillain-Barre syndrome, Crohn's disease, ulcerative colitis, psoriasis, graft versus host disease, systemic lupus erythematosus and insulin-dependent diabetes mellitus, rheumatoid arthritis, toxic shock syndrome, Alzheimer's disease, toxic shock syndrome, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis.

The compounds are also useful in methods for treating: complications including restenosis following percutaneous transluminal coronary angioplasty, traumatic arthritis, sepsis, chronic obstructive pulmonary disease and congestive heart failure.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. The above described compounds may be physically combined with the conventional therapeutics or other adjuvants into a single pharmaceutical composition. Reference is this regard may be made to Cappola et al.: U.S. patent application Ser. No. 09/902,822, PCT/US 01/21860 and U.S. provisional application No. 60/313,527, each incorporated by reference herein in their entirety. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. Reference in this regard may also be made to U.S. provisional application No. 60/339,249. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

General Synthetic Methods

The invention additionally provides for methods of making the compounds of the formula (I). The compounds of the invention may be prepared by the general methods and examples presented below, and methods known to those of ordinary skill in the art. In all schemes, unless otherwise specified, $Ar^1$, $Z$, $Y$, $R^1$-$R^6$ and $R_e$ in the formulas shown below shall have the meanings defined for these groups in the definition of the formula (I) of the invention, described hereinabove. Intermediates used in the syntheses below are either commercially available or easily prepared by methods known to those skilled in the art. Reaction progress may be monitored by conventional methods such as thin layer chromatography (TLC). Intermediates and products may be purified by methods known in the art, including column chromatography, HPLC or recrystallization.

Compounds of the invention where Q is a carbon atom, may be prepared as described in Schemes I-III. Compounds of the invention wherein Q is a nitrogen atom, may be prepared by analogous methods which will be apparent to one of ordinary skill in the art.

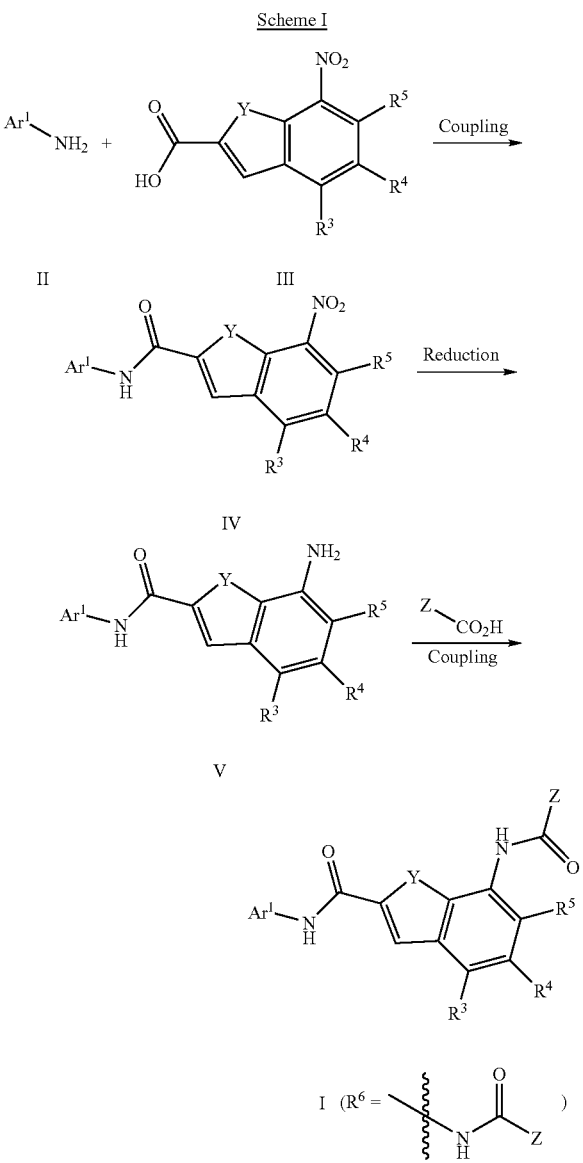

As illustrated in Scheme I an amine bearing $Ar^1$ is coupled with nitro carboxylic acid III using standard coupling conditions known in the art (see for example M. Bodanszky, 1984, The Practice of Peptide Synthesis, Springer-Verlag). For example, one may couple III and II by treating with 1-[3-(dimethylamino)propyl]-3-ethylcarbodiimide hydrochloride (EDC) followed by 1-hydroxybenzotriazole hydrate (HOBT) in a suitable solvent such as DMF. Reduction of IV to the amine V may be achieved by standard procedures known in the art. For example, reduction may be achieved by treatment of IV in a suitable solvent such as EtOAc or EtOH, with hydrogen gas in the presence of a catalyst such as palladium on carbon or by treatment of IV with stannous chloride in a suitable acidic solvent such as acetic acid and HCl. The resulting amine may then be coupled with a carboxylic acid bearing Z using standard coupling conditions as above. For example, one may treat $ZCO_2H$ with bis(2-oxo-3-oxazolidinyl)phosphinic chloride (BOP—Cl) in a suitable solvent such as $CH_2Cl_2$ in the presence of triethylamine, followed by addition of V to provide the desired compound of formula (I) ($R^6$=—

NHC(O)Z). Ar¹ and Z may be further modified by standard synthetic methods known in the art to produce additional compounds of formula (I). Several examples are described in the Synthetic Examples section.

In a modification of the above method, the order of coupling ZCO₂H and Ar¹NH₂ with the central amine ester may be reversed. This is illustrated in Scheme II.

standard hydrolysis conditions and the resulting acid coupled with Ar¹NH₂ to provide I (R⁶=—NHC(O)Z).

Compounds of formula (I) with R⁶=—NHC(O)NHR_e may be prepared as illustrated in Scheme III.

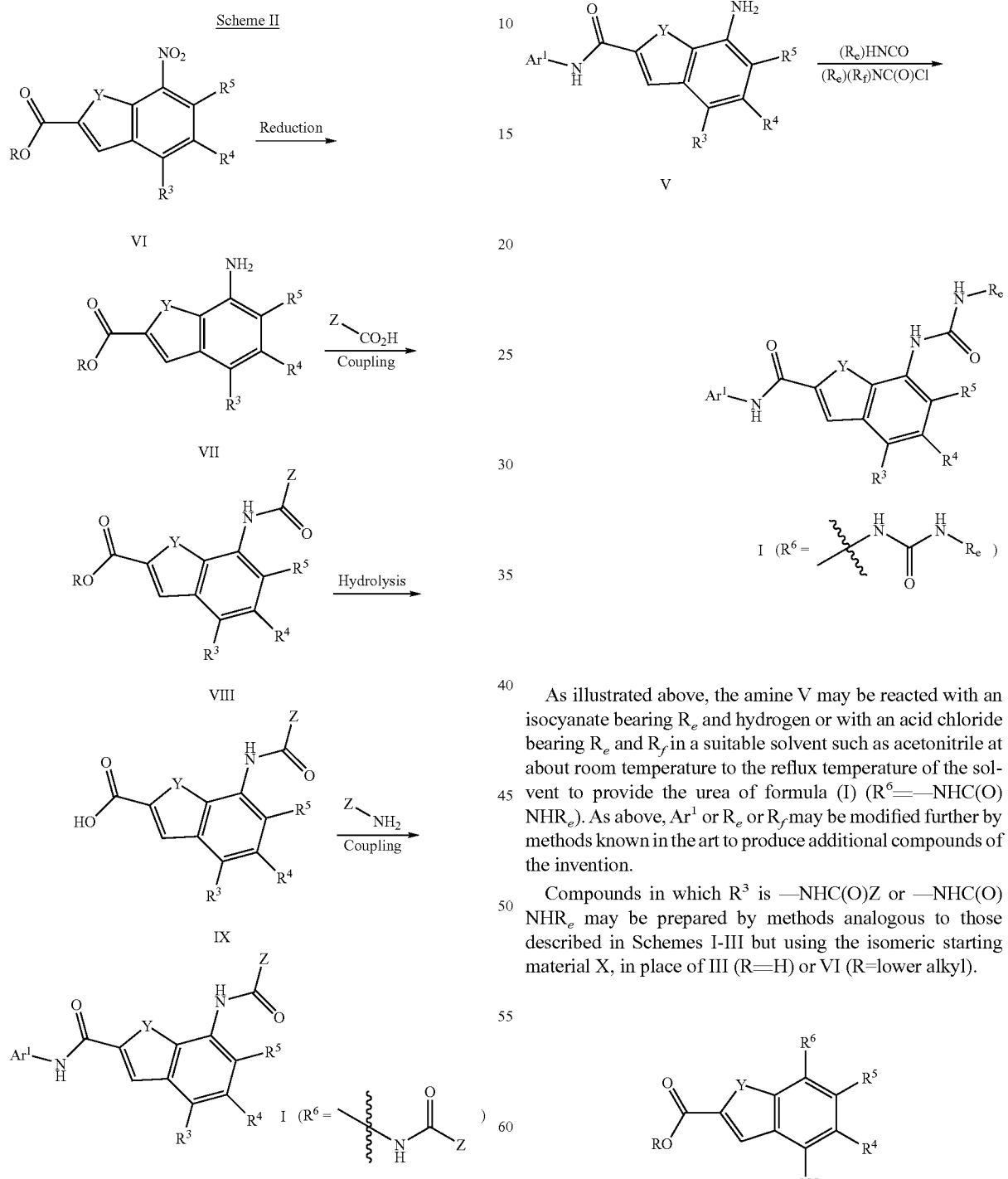

As illustrated above, the amine V may be reacted with an isocyanate bearing R_e and hydrogen or with an acid chloride bearing R_e and R_f in a suitable solvent such as acetonitrile at about room temperature to the reflux temperature of the solvent to provide the urea of formula (I) (R⁶=—NHC(O)NHR_e). As above, Ar¹ or R_e or R_f may be modified further by methods known in the art to produce additional compounds of the invention.

Compounds in which R³ is —NHC(O)Z or —NHC(O)NHR_e may be prepared by methods analogous to those described in Schemes I-III but using the isomeric starting material X, in place of III (R=H) or VI (R=lower alkyl).

As illustrated above, the nitro ester VI (R=lower alkyl such as methyl or ethyl) is reduced using conditions described above and the resulting amine VII is coupled, as described above to provide amide ester VIII. This is hydrolyzed using

SYNTHETIC EXAMPLES
Example 1
Synthesis of N-[2-(5-tert-Butyl-3-methanesulfonylamino-2-methoxy-phenylcarbamoyl)-benzo[b]thiophen-7-yl]-6-(4-methoxy-benzylamino)-nicotinamide
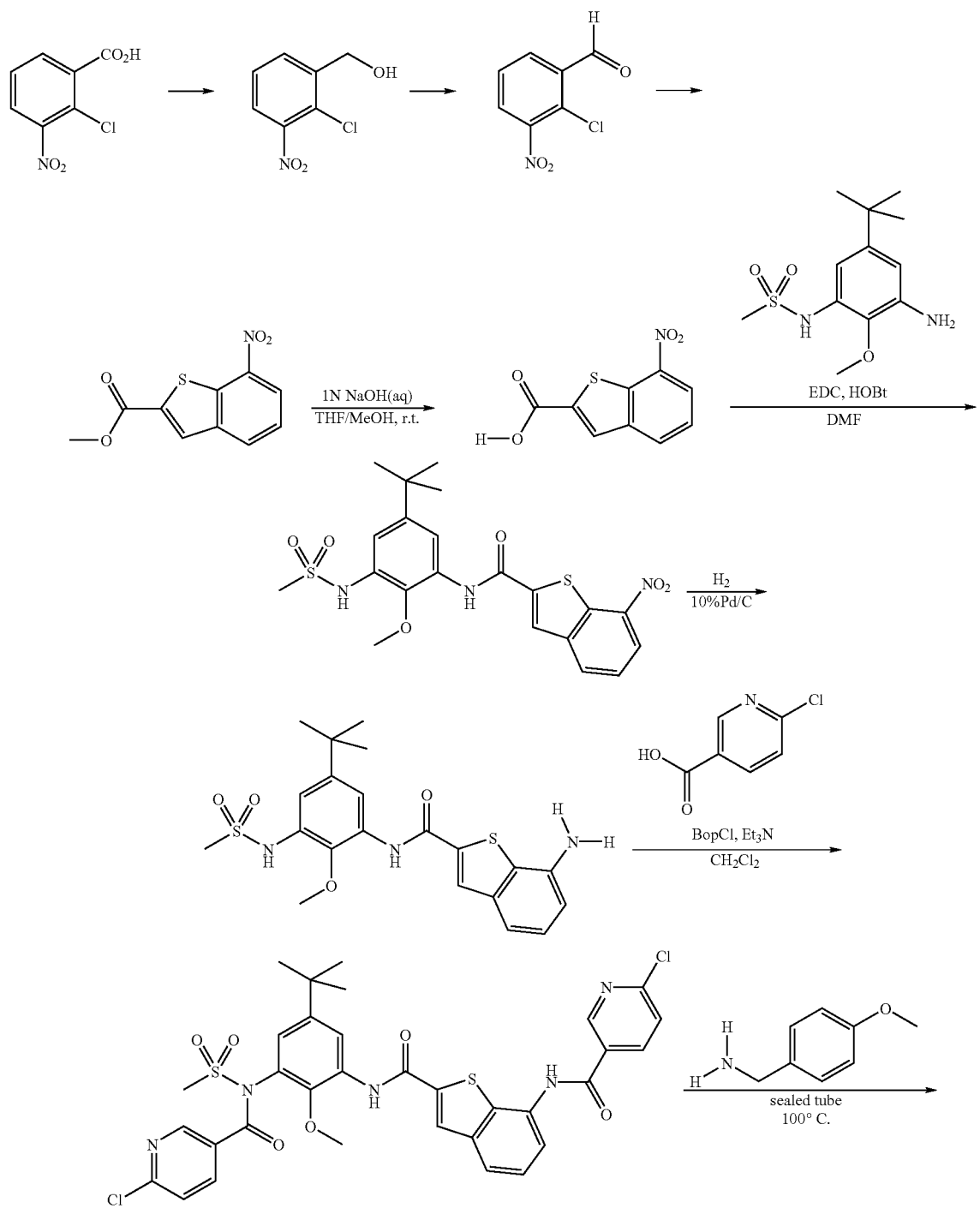

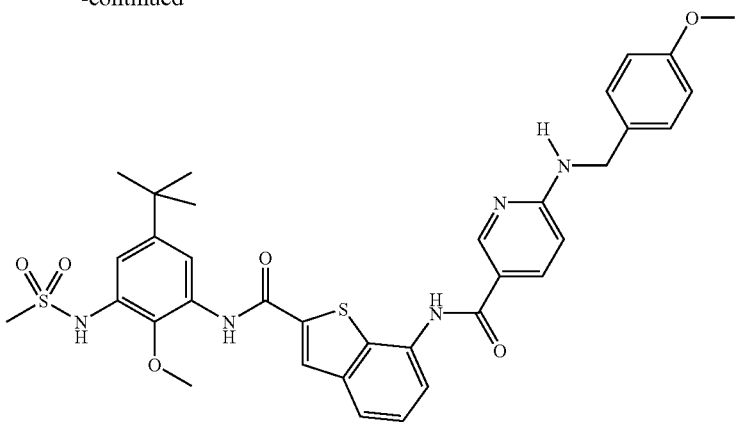

The following procedure for the synthesis of the intermediate 7-nitro-benzo[b]thiophene-2-carboxylic acid is a modification of the procedure in the chemical literature (L. K. A. Rahaman and R. M. Scrowston, *J. Chem. Soc. Perkin Trans. I,* 19, 1984, 385).

3-Nitro-2-chlorobenzoic acid (25.51 g, 126.56 mmol) was dissolved in anhydrous THF (400 mL) under a nitrogen atmosphere. The solution was cooled to −70° C. (internal temperature) under $N_2$ flush. DIBAL-H (260 mL, 1.0M in hexanes) was added dropwise over about 1½ h (internal temperature was maintained below ⁻65° C.). The reaction was allowed to slowly warm to room temperature and was stirred 12 h. The reaction was cooled to ⁻70° C. and 50 mL of MeOH was added dropwise. The reaction mixture was placed in an $H_2O$/ice bath and a 1M Rochelle's salt solution was slowly added in. This solution was stirred for 1 h at room temperature, then filtered through diatomaceous earth. The THF was concentrated in vacuo and the remaining aqueous solution was extracted 3 times with EtOAc. The combined organic layers were washed with brine, dried with $MgSO_4$, filtered, and evaporated to obtain 14.4 g (61%) of the desired 3-nitro-2-chlorobenzyl alcohol as a yellow solid.

A solution of oxalyl chloride in dichloromethane (2.0M, 116 mmol) was chilled to −70° C. (internal temperature) under a nitrogen atmosphere. DMSO (15 mL, 211.3 mmol) was added dropwise maintaining ⁻65° C. and then stirring was continued for 45 min. at −70° C. A solution of the 3-nitro-2-chlorobenzyl alcohol (14.4 g, 76.6 mmol) in dichloromethane (250 mL) was then added and the reaction stirred at −70° C. for 2 h. Triethylamine (54 mL, 387 mmol) was added dropwise and the reaction stirred for 2 h at −70° C. and then 12 h at room temperature. The reaction was quenched by the addition of 500 mL of water. The aqueous phase was extracted twice with dichloromethane. The combined organic layers were washed with brine, dried with $MgSO_4$, filtered, and evaporated to obtain a light brown solid. Column Chromatography (silica gel, 30% dichloromethane/hexanes to 70% dichloromethane/hexanes) produced 11.1 g (78%) of the desired 3-nitro-2-chlorobenzaldehyde as a yellow solid.

3-Nitro-2-chlorobenzaldehyde (11.1 g, 59.5 mmol) was dissolved in DMF (100 mL) and potassium carbonate (9.1 g, 66.2 mmol) was added. By slow addition, methyl thioglycoate (5.4 mL, 60.4 mmol) was added and a slight exotherm was observed. The reaction mixture was stirred 12 h at room temperature. Water (200 mL) was added to the reaction mixture which was then cooled on an ice/water bath. The solid was filtered and washed water until the filtrate was colorless, leaving the 13.3 g (94%) of the desired 7-nitro-benzo[b]thiophene-2-carboxylic acid methyl ester as a white solid.

To a suspension of 7-nitro-benzo[b]thiophene-2-carboxylic acid methyl ester (1.0 g) in THF/MeOH (40 mL/40 mL) was added 8.4 mL (2.0 eq) of 1N NaOH. The reaction was stirred at room temperature for 2 h. The solvent was removed in vacuo. The residue was diluted with $H_2O$/EtOAc, acidified with 3N HCl and extracted with EtOAc. The organics were dried over $MgSO_4$, filtered and concentrated to give 7-nitro-benzo[b]thiophene-2-carboxylic acid as a light yellow solid (928 mg, 98% yield).

To a solution of the above carboxylic acid (900 mg) in DMF was added EDC (1.2 eq) and HOBT (1.2 eq). After stirring for 10 min, N-(3-amino-5-tert-butyl-2-methoxy-phenyl)-methanesulfonamide (1.0 eq) was added. The suspension was stirred at room temperature for 48 h. The DMF was removed in vacuo and the resulting oil was dissolved in EtOAc, washed with water three times, followed by saturated $NaHCO_3$ solution and brine. The organics were dried over $MgSO_4$, filtered and concentrated to give a crude yellow solid which was triturated with 30% EtOAc/hex (small amount) and filtered to provide 7-nitro-benzo[b]thiophene-2-carboxylic acid (5-tert-butyl-3-methanesulfonylamino-2-methoxy-phenyl)-amide as a bright yellow solid (1.4 g, 72%).

To a solution of 7-nitro-benzo[b]thiophene-2-carboxylic acid (5-tert-butyl-3-methanesulfonylamino-2-methoxy-phenyl)-amide (1.2 g) in EtOAc (60 mL) was added 600 mg of 10% Pd/C. The reaction mixture was degassed and charged with $H_2$ two times. The reaction was then stirred at room temperature under the $H_2$ balloon. After 5 h, the reaction was diluted with EtOAc, filtered through a pad of diatomaceous earth and rinsed with EtOAc. The combined organics were concentrated to give 7-amino-benzo[b]thiophene-2-carboxylic acid (5-tert-butyl-3-methanesulfonylamino-2-methoxy-phenyl)-amide (1.1 g, 93%).

To a suspension of 6-chloro-nicotinic acid (2.3 eq) and Bis(2-oxo-3-oxazolidinyl)phosphinic chloride (BOP—Cl) (4.0 eq) in $CH_2Cl_2$ (10 mL) was added triethylamine (4.0 eq). After 1 h, the reaction solution was almost clear and 7-amino-benzo[b]thiophene-2-carboxylic acid (5-tert-butyl-3-methanesulfonylamino-2-methoxy-phenyl)-amide (98 mg) was added. The yellow reaction solution was stirred at room temperature 12 h. The reaction mixture was partitioned between EtOAc and water, and the organic layer then washed with brine. The organics were dried over MgSO₄, filtered and concentrated to give N-(2-{5-tert-butyl-3-[(6-chloro-pyridine-3-carbonyl)-methanesulfonyl-amino]-2-methoxy-phenylcarbamoyl}-benzo[b]thiophen-7-yl)-6-chloro-nicotinamide as a white solid (125 mg, 78%).

To the above chloronicotinamide intermediate (107 mg) in a sealed tube was added 4-methoxybenzylamine (700 µL). The reaction was purged with Ar (Argon) and then heated to 100° C. in the sealed tube. It became a clear yellow solution. After 4 h, the reaction was cooled to room temperature, diluted with EtOAc, washed with NH₄Cl solution, water, and brine. The organics were dried over MgSO₄, filtered and concentrated down to give crude product which was purified by flash column chromatography on silica gel to give (96 mg, 96%) of the title compound, m.p. 137-139° C.

Example 2

Synthesis of 6-amino-N-[2-(5-tert-butyl-3-methanesulfonylamino-2-methoxy-phenylcarbamoyl)-benzo[b]thiophen-7-yl]-nicotinamide gel (7%-10% MeOH/CH₂Cl₂) to provide the title compound as a white solid (14 mg, 85% yield), m.p. 234-235° C.

Example 3

Synthesis of N-[2-(5-tert-Butyl-3-methanesulfonylamino-2-methoxy-phenylcarbamoyl)-benzo[b]thiophen-7-yl]-6-cyclopropylamino-nicotinamide

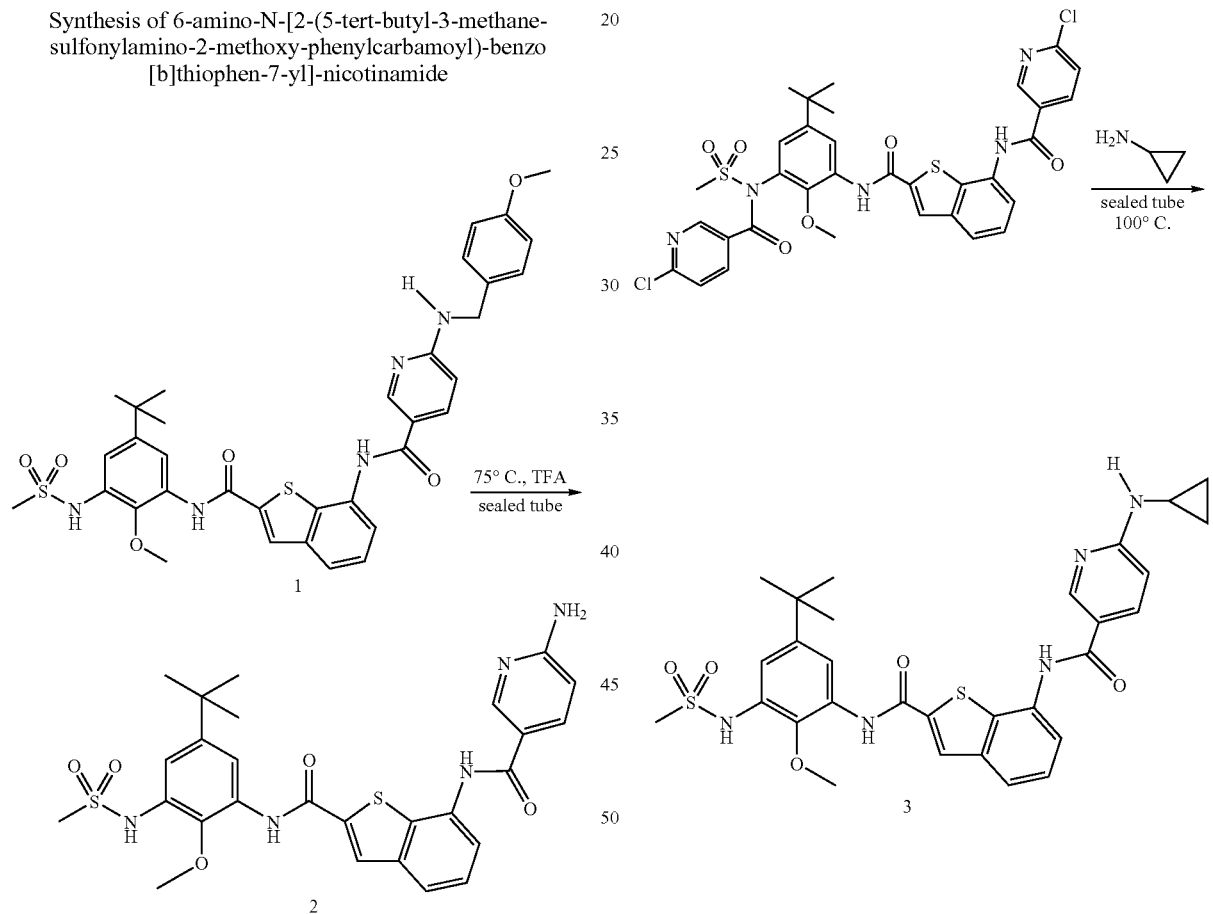

To N-[2-(5-tert-Butyl-3-methanesulfonylamino-2-methoxy-phenylcarbamoyl)-benzo[b]thiophen-7-yl]-6-(4-methoxy-benzylamino)-nicotinamide (Example 1) (20 mg) in a sealed tube was added 90 µL of trifluoroacetic acid. The clear solution was purged with Ar and then heated to 75° C. in a sealed tube 12 h. The reaction was cooled to room temperature and diluted with toluene to remove excess trifluoroacetic acid in vacuo. The resulting trifluoroacetic acid salt of the desired product was dissolved in EtOAc and washed with saturated NaHCO₃ solution and brine. The organics were dried over MgSO₄, filtered and concentrated to give a foam which was further purified by flash chromatography on silica To N-(2-{5-tert-butyl-3-[(6-chloro-pyridine-3-carbonyl)-methanesulfonyl-amino]-2-methoxy-phenylcarbamoyl}-benzo[b]thiophen-7-yl)-6-chloro-nicotinamide (see Example 1) (33 mg) in a sealed tube was added 200 µL of cyclopropylamine. The reaction was purged with Ar and heated to 100° C. in the sealed tube 12 h. The reaction mixture was cooled to room temperature and diluted with EtOAc, washed by NH₄Cl solution, water, and brine. The organics were dried over MgSO₄, filtered, concentrated down to give a residue which was purified by flash chromatography on silica gel (CH₂Cl₂-2% MeOH/CH₂Cl₂) to provide the title compound (21 mg, 71%), m.p. >264° C. dec.

Example 4

Synthesis of N-[2-(5-tert-Butyl-3-methanesulfonylamino-2-methoxy-phenylcarbamoyl)-benzo[b]thiophen-7-yl]-6-((S)-2-methoxy-1-methyl-ethylamino)-nicotinamide

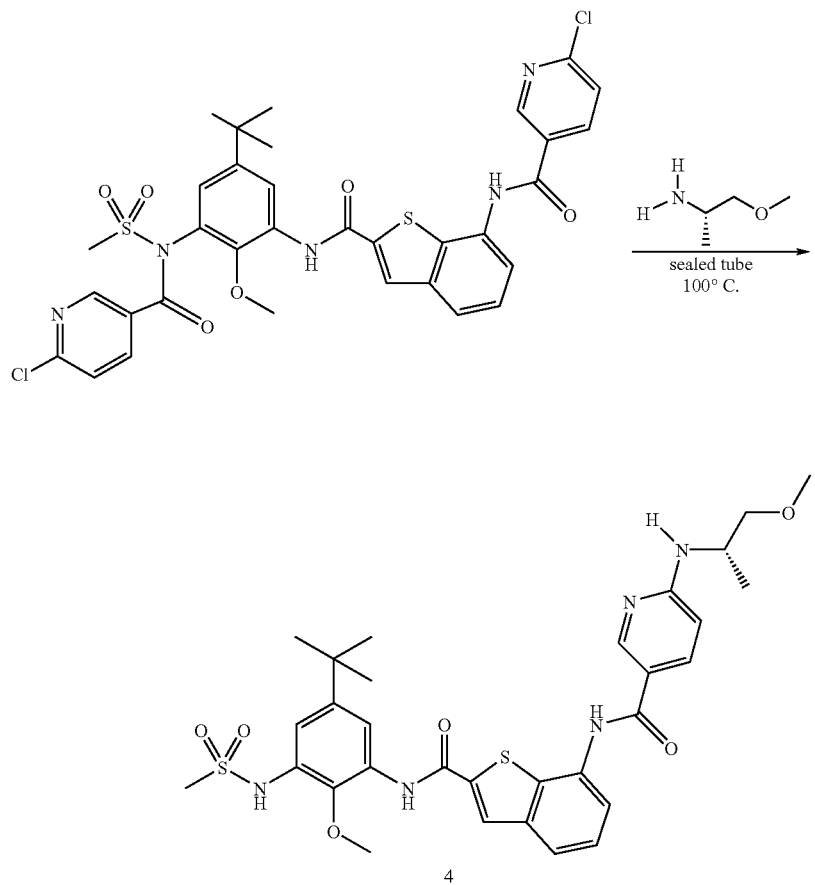

To N-(2-{5-tert-butyl-3-[(6-chloro-pyridine-3-carbonyl)-methanesulfonyl-amino]-2-methoxy-phenylcarbamoyl}-benzo[b]thiophen-7-yl)-6-chloro-nicotinamide (see Example 1) (33 mg) in a sealed tube was added (S)-(+)-1-methoxy-2-propylamine (150 µL). The reaction was purged with Ar and then heated to 100° C. in the sealed tube 12 h. The reaction mixture was cooled to room temperature and diluted with EtOAc, washed with NH₄Cl solution, water, and brine. The organics were dried over MgSO₄, filtered and concentrated down to give the crude product which was purified by flash chromatography on silica gel (CH₂Cl₂-2% MeOH/CH₂Cl₂) to give the title compound (16 mg, 53%) as a yellow foam.

Example 5

Synthesis of N-[2-(5-tert-Butyl-3-methanesulfonylamino-2-methoxy-phenylcarbamoyl)-benzo[b]thiophen-7-yl]-6-chloronicotinamide

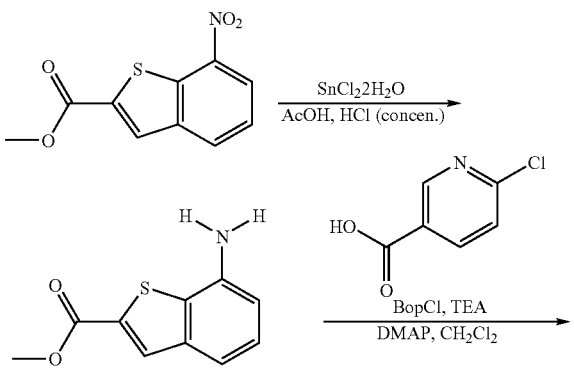

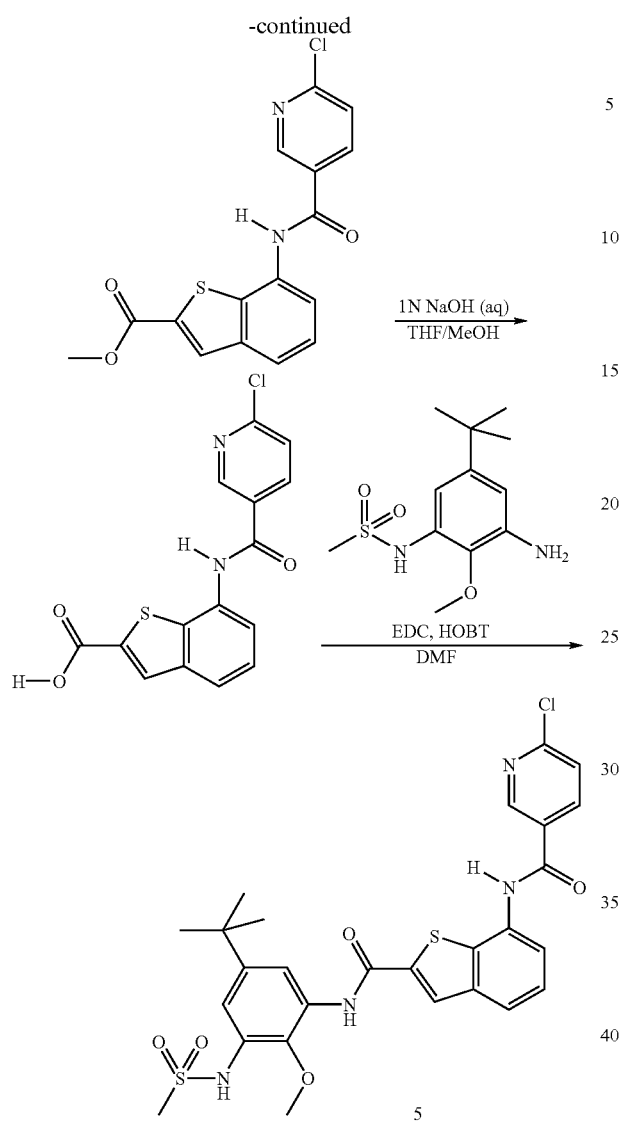

To a mixture of 7-nitro-benzo[b]thiophene-2-carboxylic acid methyl ester (100 mg) in acetic acid (4 mL) was added a solution of SnC$_2$.2H$_2$O (10 eq) in 1.5 mL of concentrated HCl. The reaction was stirred at room temperature 12 h. The excess acid was partially removed in vacuo, and the reaction mixture was then poured into a flask (250 mL) and was neutralized with saturated NaHCO$_3$ solution at 0° C. The pH was brought up to pH 9 by adding solid NaHCO$_3$. The resulting aqueous mixture was diluted with EtOAc, and the Tin-by product was removed by filtering through a pad of diatomaceous earth. The pad was rinsed with EtOAc and the combined filtrates were partitioned in a separatory funnel. The aqueous layer was extracted with EtOAc two times times. The combined organics were dried over MgSO$_4$, filtered and concentrated to give the desired 7-amino-benzo[b]thiophene-2-carboxylic acid methyl ester (100%).

To a solution of 6-chloronicotinic acid (1.5 eq) and triethylamine (2.0 eq) in CH$_2$Cl$_2$ (5 mL) was added BopCl (2.0 eq). After 15 min, 7-amino-benzo[b]thiophene-2-carboxylic acid methyl ester (87 mg) in CH$_2$Cl$_2$ and 4-dimethylaminopyridine (DMAP) (1.0 eq) were added to the reaction solution above. The reaction was stirred at room temperature 12 h. The reaction was then diluted with EtOAc, and washed with NaHCO$_3$ solution and brine. The organics were dried over MgSO$_4$, filtered and concentrated to give a crude material which was purified by flash chromatography on silica gel (20%-50% EtOAc/hexane) to provide 100 mg (68%) of the desired 7-[(6-chloro-pyridine-3-carbonyl)-amino]-benzo[b]thiophene-2-carboxylic acid methyl ester as a light yellow solid.

To a solution of the above methyl ester (91 mg) in THF/MeOH (3 mL/3 mL) was added 655 uL (2.5 eq) of 1N NaOH. The reaction solution was stirred at room temperature 12 h. Water CH$_2$Cl$_2$ and were added to the reaction. The mixture was acidified with 1N HCl to pH 4. The mixture was extracted with CH$_2$Cl$_2$ until most of the product was extracted into the organic layer. The organics were dried over MgSO$_4$, filtered and concentrated to give 7-[(6-chloro-pyridine-3-carbonyl)-amino]-benzo[b]thiophene-2-carboxylic acid as a light yellow solid (90 mg, >100%).

To a solution of the above carboxylic acid (50 mg) in DMF (1.5 mL) was added EDC (1.5 eq) and HOBT (1.5 eq). The reaction was stirred at room temperature for 15 min, then N-(3-amino-5-tert-butyl-2-methoxy-phenyl)-methanesulfonamide (1.2 eq) was added. The reaction was stirred 12 h, then the DMF was removed in vacuo, the residue was taken up in EtOAc and washed with water, followed by brine. The organics were dried over MgSO$_4$, filtered, and concentrated and the residue was purified by flash chromatography on silica gel (20%-60% EtOAc/hexane) to give the title compound as a white solid (36 mg, 41% yield for two steps).

Example 6

Synthesis of N-[2-(5-tert-Butyl-3-methanesulfonylamino-2-methoxy-phenylcarbamoyl)-benzo[b]thiophen-7-yl]-nicotinamide

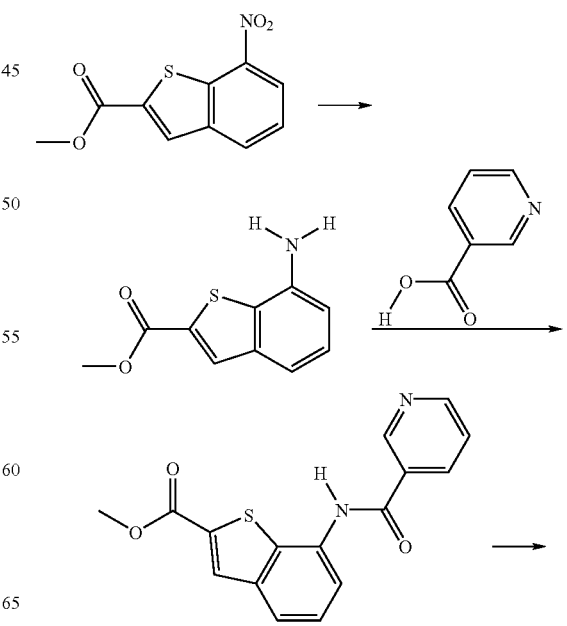

-continued

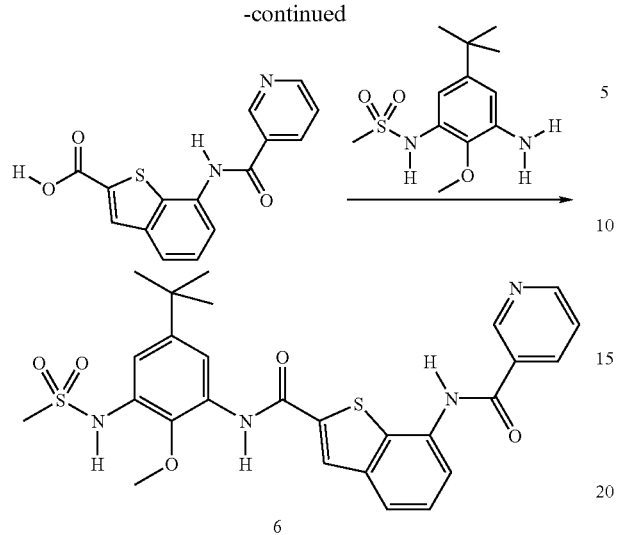

6

7-Nitro-benzo[b]thiophene-2-carboxylic acid methyl ester (1 g, 4.22 mmol) was suspended in EtOAc (40 mL) and a suspension of 10% Pd/C (400 mg) in 20 mL EtOAc was added. Hydrogen gas was introduced into the flask from an H$_2$-filled balloon attached to a needle inserted through a septum. The black suspension was stirred 12 h at room temperature. After stirring 12 h, the black suspension was filtered through diatomaceous earth and the filter cake was washed several times with EtOAc. The combined filtrates were dried (MgSO$_4$), filtered and the solvent was removed to afford 7-amino-benzo[b]thiophene-2-carboxylic acid methyl ester as a yellow solid (860 mg, 100%).

Nicotinic acid (401 mg, 3.26 mmol) was suspended in 20 mL CH$_2$Cl$_2$ and Et$_3$N (330 mg, 3.26 mmol, 245 uL) was added to give a colorless solution. BopCl (829 mg, 3.26 mmol) was added and the reaction was stirred at room temperature for about 15 min, then a solution of 7-amino-benzo[b]thiophene-2-carboxylic acid methyl ester (450 mg, 2.17 mmol) in 2 mL CH$_2$Cl$_2$ was added. The yellow solution was stirred at room temperature for 12 h. After this time, room temperature, the solvent was removed from the reaction and the residue was partitioned between EtOAc (100 mL) and water (75 mL). The layers were separated and the organic portion was washed with water (2×75 mL), brine (75 mL), dried (MgSO$_4$), filtered and the solvent was removed in vacuo to afford 7-[(pyridine-3-carbonyl)-amino]-benzo[b]thiophene-2-carboxylic acid methyl ester as a yellow solid (460 mg, 45%).

The above methyl ester (460 mg, 1.47 mmol) was suspended in a mixture of 15 mL THF and 4 mL H$_2$O and LiOH*H$_2$O (124 mg, 2.95 mmol) were added. The suspension rapidly became a darker yellow solution and was stirred at room temperature 12 h. After stirring 12 h, the THF was removed from the reaction in vacuo and the aqueous residue was diluted with water (5 mL) and acidified with 1 N HCl. The suspension was chilled in an ice bath then filtered. The filter cake was washed several times with cold water then dried 12 h under a stream of nitrogen to afford 410 mg (93%) of (7-[(pyridine-3-carbonyl)-amino]-benzo[b]thiophene-2-carboxylic acid) as a yellow solid.

The above carboxylic acid (100 mg, 0.335 mmol) and N-(3-amino-5-tert-butyl-2-methoxyphenyl)-methanesulfonamide (91 mg, 0.335 mmol) were dissolved in 2 mL DMF and stirred at room temperature. After about 10 min, HATU (127 mg, 0.335 mmol) and HOBt (45 mg, 0.335 mmol) were added followed by diisopropylamine (87 mg, 0.670 mmol, 120 uL) and the solution was stirred at room temperature. After stirring for eight days, the entire reaction was partitioned between EtOAc (75 mL) and water (50 mL). The layers were separated and the organic portion was washed with water (2×25 mL), brine (25 mL), dried (MgSO$_4$), filtered and the solvent was removed to afford a tan solid. Column chromatography (EtOAc, silica gel) afforded the title compound as a colorless solid (105 mg, 57%).

Example 7

Synthesis of N-[2-(5-tert-Butyl-3-methanesulfonylamino-2-methoxy-phenylcarbamoyl)-benzo[b]thiophen-4-yl]-nicotinamide

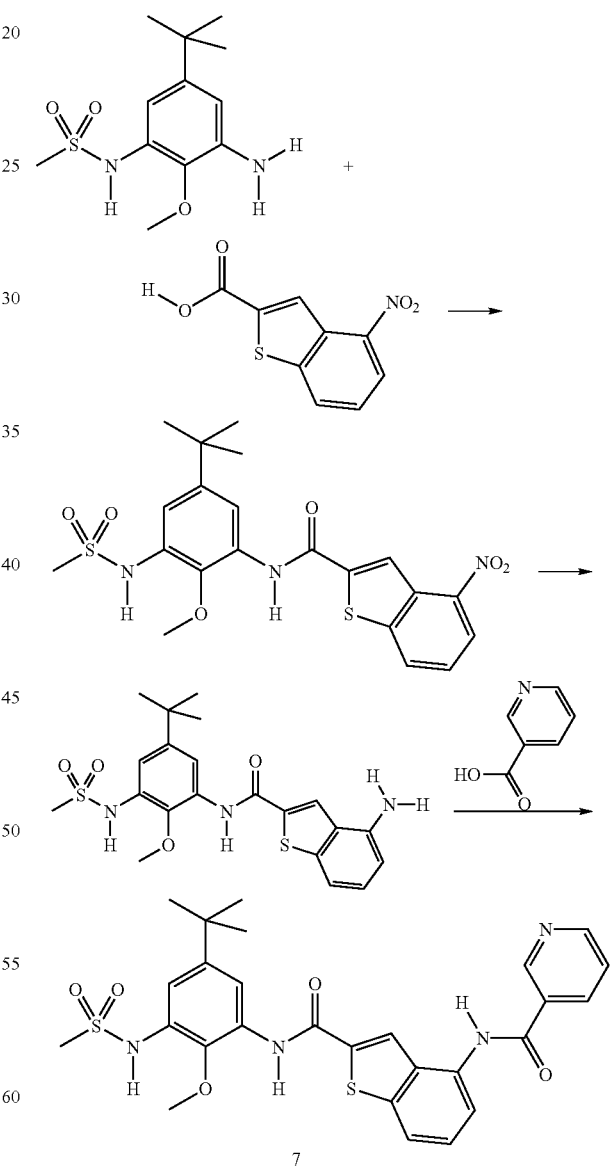

7

4-Nitro-benzo[b]thiophene-2-carboxylic acid (369 mg, 1.65 mmol) and N-(3-amino-5-tert-butyl-2-methoxy-phenyl)-methanesulfonamide (500 mg, 1.84 mmol) were dissolved in 25 mL DMF and stirred at room temperature. After about 10 min, EDC (317 mg, 1.65 mmol) and HOBt (224 mg, 1.65 mmol) were added and the brown solution was stirred at room temperature 12 h. After stirring 12 h, the reaction was partitioned between EtOAc (150 mL) and water (50 mL). The layers were separated and the organic portion was washed with water (2×25 mL), brine (25 mL), dried (MgSO$_4$), filtered and the solvent was removed in vacuo to afford a brown solid. Column chromatography on silica gel afforded 4-nitro-benzo[b]thiophene-2-carboxylic acid (5-tert-butyl-3-methanesulfonylamino-2-methoxy-phenyl)-amide as a pale yellow solid (200 mg, 25%).

The above nitro compound (200 mg, 0.42 mmol) was suspended in about 10 mL EtOAc and 10% Pd/C (50 mg) in 2 mL EtOAc was added. Hydrogen gas was introduced into the flask from an H$_2$-filled balloon attached to a needle inserted through a septum. The black suspension was stirred 12 h at room temperature. After stirring 12, the black suspension was filtered through diatomaceous earth and the filter cake was washed several times with EtOAc. The combined filtrates were dried (MgSO$_4$), filtered and the solvent was removed to afford 4-amino-benzo[b]thiophene-2-carboxylic acid (5-tert-butyl-3-methanesulfonylamino-2-methoxy-phenyl)-amide as a pale yellow solid (170 mg, 90%).

Nicotinic acid (14 mg, 0.11 mmol) and the above amine (50 mg, 0.11) were dissolved in 2 mL DMF and stirred at room temperature. After about 10 min, EDC (21 mg, 0.11 mmol) and HOBt (15 mg, 0.11 mmol) were added and the brown solution was stirred at room temperature. After stirring for 2.5 days, an additional 10 mg (0.08 mmol) of nicotinic acid were added and stirring at room temperature was continued. After stirring for an additional 36 h, the reaction was partitioned between EtOAc (100 mL) and water (20 mL). The layers were separated and the organic portion was washed with water (2×20 mL), brine (20 mL), dried (MgSO$_4$), filtered and the solvent was removed in vacuo to afford a orange solid. Column chromatography on silica gel eluting with EtOAc afforded the title compound as a pale yellow solid (22 mg, 36%).

Example 8

Synthesis of 7-[4-(piperazine-1-sulfonyl)-benzoylamino]-benzo[b]thiophene-2-carboxylic acid (5-tert-butyl-3-methanesulfonylamino-2-methoxy-phenyl)-amide

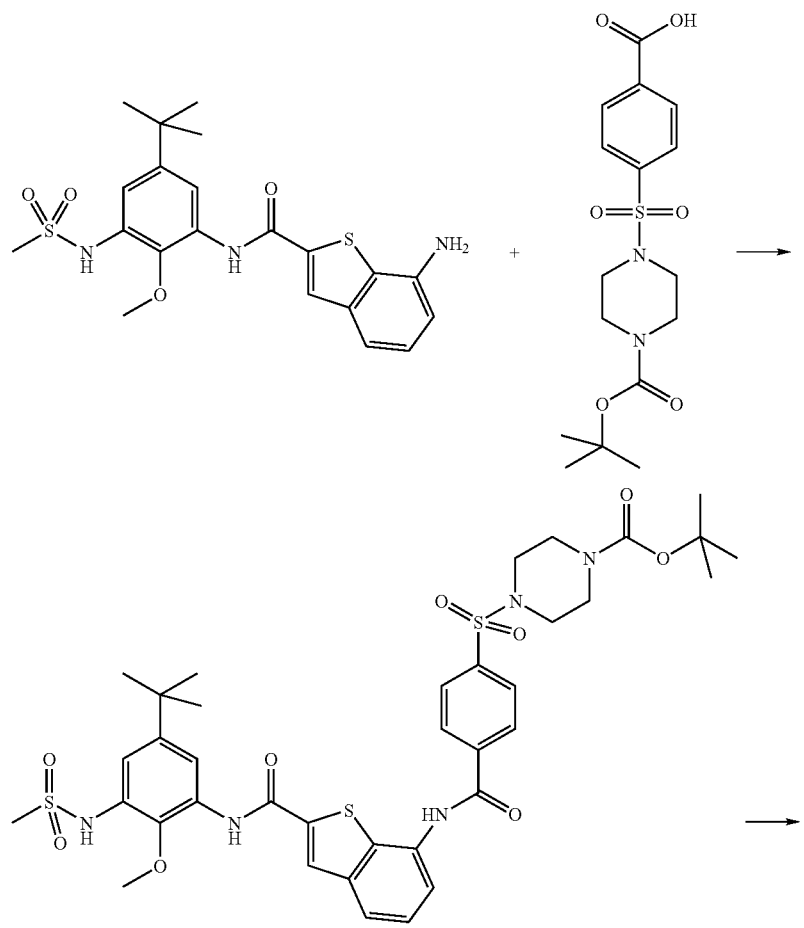

-continued

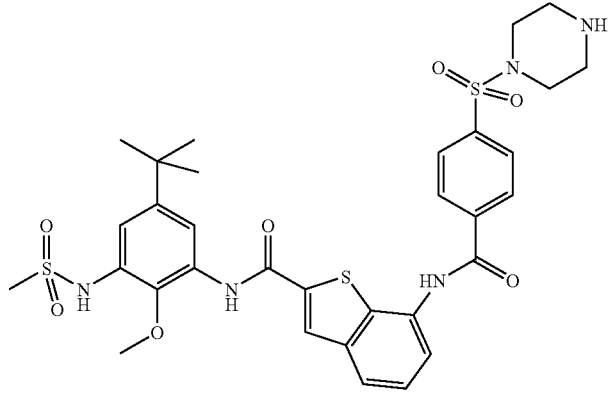

8

7-Amino-benzo[b]thiophene-2-carboxylic acid (5-tert-butyl-3-methanesulfonylamino-2-methoxy-phenyl)-amide (0.100 g, 0.223 mmol), 4-(4-carboxy-benzenesulfonyl)-piperazine-1-carboxylic acid tert-butyl ester (0.160 g, 0.432 mmol), HOBT (0.060 g, 0.444 mmol) and EDC (0.080 g, 0.417 mmol) were dissolved in DMF (7.0 mL) and stirred at room temperature under an Ar atmosphere for 42 h. The reaction mixture was transferred to a separatory funnel containing water and the aqueous layer was extracted with EtOAc (3×10 mL). The combined organic extracts were washed with water, NH$_4$Cl, brine and dried over MgSO$_4$. The solvent was filtered and evaporated on a rotary evaporator. The resultant crude product was purified by chromatography (60% EtOAc/hexane) to give the desired 4-{4-[2-(5-tert-butyl-3-methanesulfonylamino-2-methoxy-phenylcarbamoyl)-benzo[b]thiophen-7-ylcarbamoyl]-benzenesulfonyl}-piperazine-1-carboxylic acid tert-butyl ester (25.5 mg).

A solution of the above t-butyl ester (0.021 g, 0.027 mmol) in dioxane/HCl (1.0 mL) was stirred at room temperature for 1.5 h. The solvent was evaporated on a rotary evaporator with the resultant residue being dissolved in EtOAc and transferred to a separatory funnel containing water. The organic layer was subsequently washed with NaHCO$_3$ (3×5 mL), dried over MgSO$_4$, and the solvent was filtered and evaporated on a rotary evaporator to give the title compound (8.7 mg).

Example 9

Synthesis of N-[2-(5-tert-Butyl-3-methanesulfonylamino-2-methoxy-phenylcarbamoyl)-4-chloro-benzo[b]thiophen-7-yl]-nicotinamide

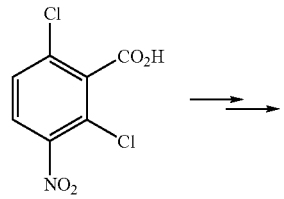

-continued

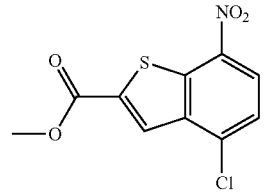

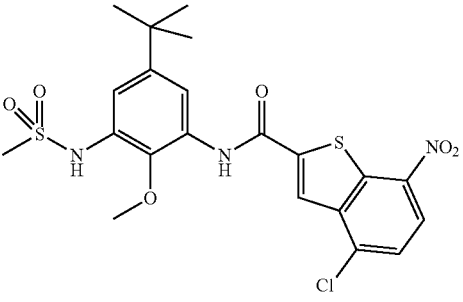

9

4-Chloro-7-nitro-benzo[b]thiophene-2-carboxylic acid methyl ester was prepared from 2,6-dichloro-3-nitro-benzoic acid using a procedure analogous to that described in Example 1 for 7-nitro-benzo[b]thiophene-2-carboxylic acid methyl ester. Then, following the procedure described in Example 1, the ester was hydrolyzed and the resulting acid coupled with N-(3-amino-5-tert-butyl-2-methoxy-phenyl)-methanesulfonamide to provide 4-chloro-7-nitro-benzo[b]thiophene-2-carboxylic acid (5-tert-butyl-3-methanesulfonylamino-2-methoxy-phenyl)-amide.

The above nitro intermediate (75 mg, 0.15 mmol) was dissolved in 10 mL HOAc and 0.5 mL concentrated HCl. To this was added tin(II)chloride dihydrate (338 mg, 1.5 mmol). After stirring at room temperature for 12 h, the reaction was basicified to about pH 6 with 3 M NaOH. The reaction was filtered and the filtrate was stirred for 0.5 h with saturated NaHCO₃. The aqueous material was extracted with EtOAc to provide 42 mg (58%) of the desired 4-chloro-7-amino-benzo[b]thiophene-2-carboxylic acid (5-tert-butyl-3-methanesulfonylamino-2-methoxy-phenyl)-amide.

The above amine intermediate was coupled with nicotinic acid using the procedure described in the last step of Example 7 to provide 15 mg (35%) of the title compound.

Example 10

Synthesis of 7-(3-phenyl-ureido)-benzo[b]thiophene-2-carboxylic Acid (5-tert-butyl-3-methanesulfonylamino-2-methoxy-phenyl)-amide

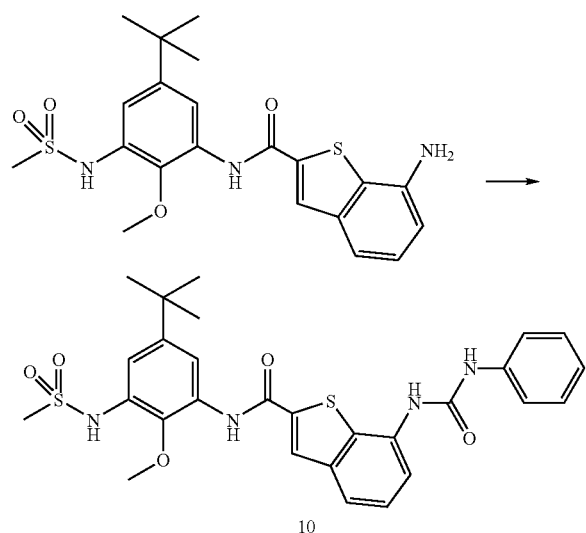

To an opaque yellow solution of 7-amino-benzo[b]thiophene-2-carboxylic acid (5-tert-butyl-3-methanesulfonylamino-2-methoxy-phenyl)-amide (see Example 1) (30 mg, 0.07 mmol) in acetonitrile was added phenyl isocyanate (10 μL, 0.9 mmol). The reaction was heated to 80° C. for 12 h in a sealed tube, then cooled to room temperature. The product precipitated out directly to provide 20 mg (50%) of the title compound.

Example 11

Synthesis of N-[2-(5-tert-butyl-3-methanesulfonylamino-2-methoxy-phenylcarbamoyl)-1-methylindol-7-yl]-nicotinamide

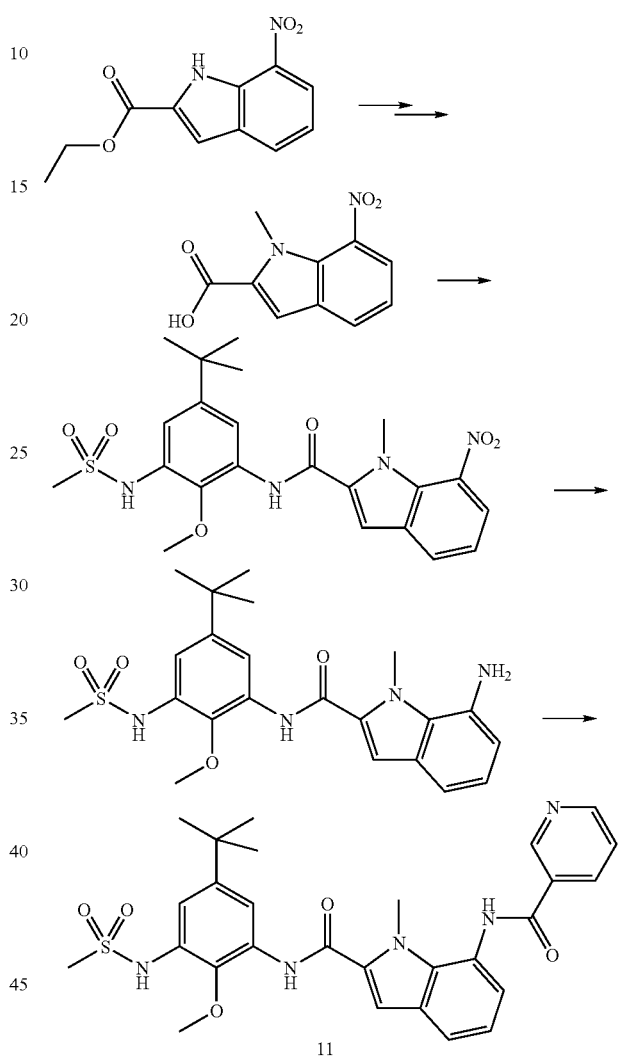

To a suspension of NaH (60% in mineral oil, 0.77 g, 19.2 mmol) in 40 mL of dry DMF was added ethyl 7-nitroindole-2-carboxylate (3.0 g, 12.8 mmol). The resulting brown solution was stirred at room temperature for 1 h. MeI (2.5 mL, 40 mmol) in 10 mL of DMF was then added dropwise. After 5.5 h, the reaction mixture was poured into ice and extracted with EtOAc. The extracts were washed with water and brine, and dried (Na₂SO₄). After removal of the solvents, yellow solid (3.1 g) was obtained. The yellow solid (2.2 g) was mixed with EtOH (50 mL) and 2N aqueous NaOH (50 mL) and the mixture was heated at reflux for 2.5 h and then stirred at room temperature 12 h. After removal of EtOH, the reaction mixture was extracted with ether (50 mL). The aqueous layer was acidified with 2N HCl and extracted with EtOAc to give (1.9 g, 95%) of 1-methyl-7-nitroindole-2-carboxylic acid.

A suspension of 1-methyl-7-nitroindole-2-carboxylic acid (220 mg, 1 mmol) in 5 mL of SO₂Cl was heated at reflux for 3 h to give a yellow solution. The excess SO₂Cl was removed by distillation and the resulting yellow solid was dissolved in 5 mL of dry THF. Et$_3$N (0.21 mL, 1.5 mmol) and N-(3-amino-5-tert-butyl-2-methoxy-phenyl)-methanesulfonamide (327 mg, 1.2 mmol) were added successively and the mixture was stirred 12 h. The reaction mixture was extracted with EtOAc to give 410 mg (87%) of 1-methyl-7-nitroindole-2-carboxylic acid (5-tert-butyl-3-methanesulfonylamino-2-methoxy-phenyl)-amide.

A mixture of the above nitro intermediate and 10% Pd—C (100 mg) in 10 mL of EtOAc was stirred in a hydrogen atmosphere 12 h. The reaction mixture was filtered through a layer of diatomaceous earth and the filtrate was concentrated to give (340 mg, 91%) of 7-amino-1-methylindole-2-carboxylic acid (5-tert-butyl-3-methanesulfonylamino-2-methoxy-phenyl)-amide.

A mixture of the above amine intermediate (217.5 mg, 0.49 mmol), nicotinic acid (74 mg, 0.6 mmol), 1-hydroxybenzotriazole hydrate (HOBT, 81 mg, 0.6 mmol) and 1-[3-(dimethylamino)propyl]-3-ethylcarbodiimide hydrochloride (EDC, 115 mg, 0.6 mmol) was stirred 12 h. The reaction was not completed and additional nicotinic acid (37 mg, 0.3 mmol), HOBT (41 mg, 0.3 mmol) and EDC (58 mg, 0.3 mmol) was added and the reaction was complete after another 5 h. The reaction mixture was extracted with EtOAc, dried and concentrated and the product purified by reverse phase HPLC on a C18 column eluting with an acetonitrile-water gradient to provide (160 mg, 59%) of the title compound.

Example 12

Synthesis of 1-methyl-7-morpholinecarboxamidoindole-2-carboxylic Acid (5-tert-butyl-3-methanesulfonylamino-2-methoxy-phenyl)-amide

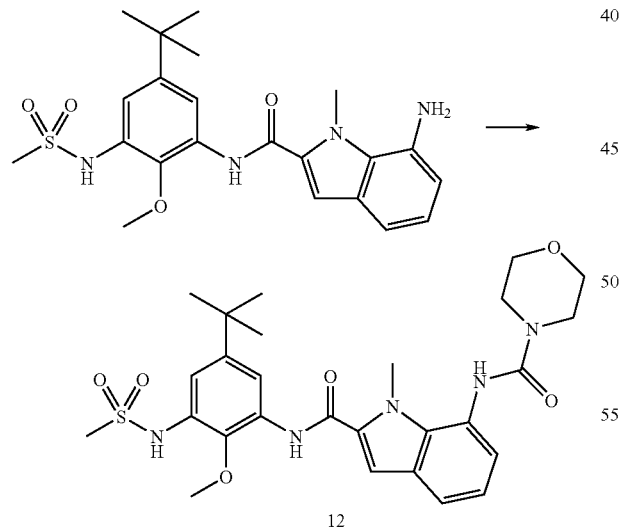

12

A mixture of 7-amino-1-methylindole-2-carboxylic acid (5-tert-butyl-3-methanesulfonylamino-2-methoxy-phenyl)-amide (64 mg, 0.14 mmol), morpholinecarbonyl chloride (0.13 mL, 1.1 mmol), diisopropylethylamine (0.2 mL) and Et$_3$N (0.5 mL) was stirred for 4 days. The reaction mixture was extracted and purified by reverse phase HPLC on a C18 column eluting with an acetonitrile-water gradient to provide 15 mg (19%) of the title compound.

Example 13

Synthesis of N-[2-(5-tert-Butyl-3-methanesulfonylamino-2-methoxy-phenylcarbamoyl)-benzo[b]thiophen-7-yl]-5-(N,N-dimethylcarbamoyl)-nicotinamide

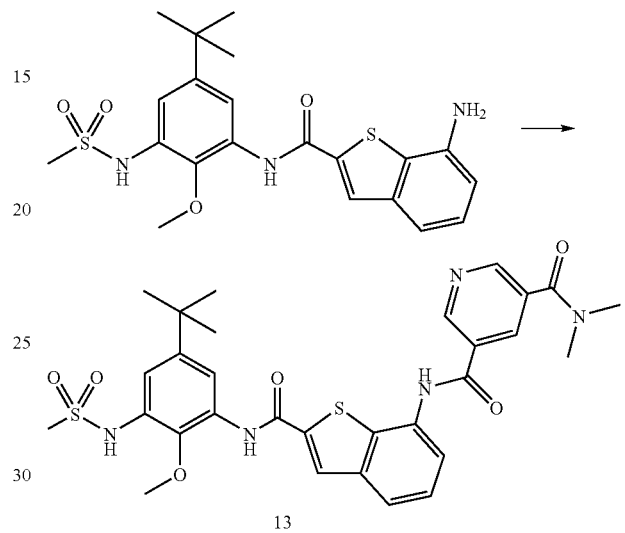

13

A suspension of pyridine-3,5-dicarboxylic acid (43.5 mg, 0.26 mmol) in 2.5 mL of SOCl$_2$ was refluxed for 2.5 h to give a light yellow solution. The excess SOCl$_2$ was removed by distillation and the resulting solid was dissolved in 2 mL of dry THF. Triethylamine (0.12 mL, 0.86 mmol) and a solution of 7-aminobenzo[b]thiophene-2-carboxylic acid (5-tert-butyl-3-methanesulfonylamino-2-methoxy-phenyl)-amide (39 mg, 0.087 mmol) in 2 mL of THF was added and the reaction mixture was stirred 12 h. A solution of dimethylamine (2.0 M in THF, 1 mL, 2 mmol) was added and the reaction mixture was stirred for additional 5 h. The reaction mixture was then extracted with EtOAc and purified by reverse phase HPLC on a C18 column eluting with an acetonitrile-water gradient to provide 12 mg (24%) of the title compound.

Example 14

Synthesis of 7-(2-methoxy-benzoylamino)-benzo[b]thiophene-2-carboxylic Acid (5-tert-butyl-3-methanesulfonylamino-2-methoxy-phenyl-amide

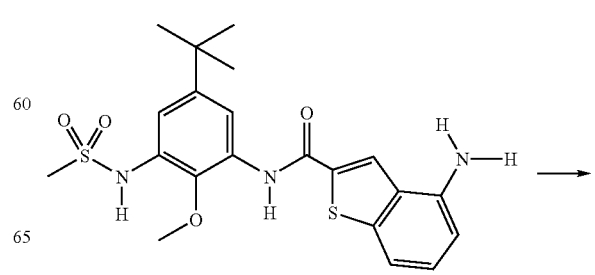

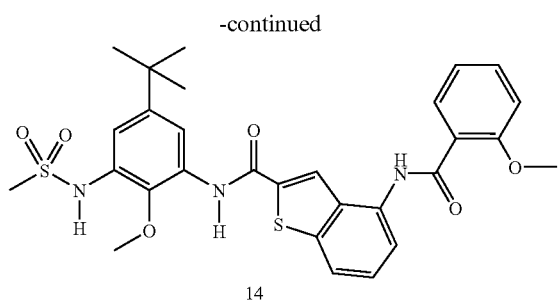

14

7-Amino-benzo[b]thiophene-2-carboxylic acid (5-tert-butyl-3-methanesulfonylamino-2-methoxy-phenyl-amide (25 mg, 0.055 mmol) was placed in 1,2-dichloroethane (2 mL). N,N-dimethylaminopyridine (6.65 mg, 0.055 mmol) and o-anisoyl chloride (9.35 mg, 0.055 mmol) were added at room temperature. The reaction mixture was stirred for 4 h and then passed through a 100 mg SCX (Varian) cartridge using 1 mL of 1,2-dichloroethane as eluant. The filtrate was concentrated in vacuo providing 17.2 mg of crude product. Purification by preparative reverse-phase HPLC (90:10 to 5:95 water/AcCN) produced 7.9 mg of the title compound as a white solid.

Example 15

4-Methyl-[1,2,3]thiadiazole-5-carboxylic Acid [2-(5-tert-butyl-3-methanesulfonylamino-2-methoxy-phenylcarbamoyl)-benzo[b]thiophen-7-yl]-amide

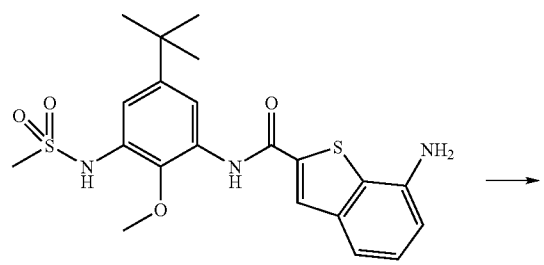

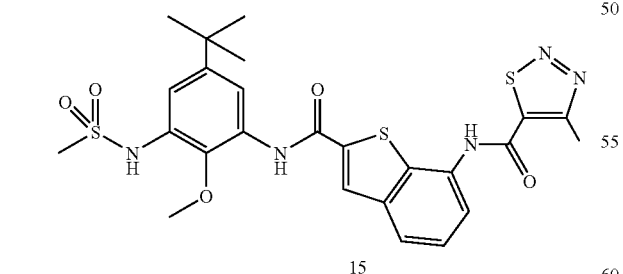

15

Was prepared as described for -[2-(5-tert-Butyl-3-methanesulfonylamino-2-methoxy-phenylcarbamoyl)-benzo[b]thiophen-7-yl]-nicotinamide starting with 5-methoxy-nicotinic acid to provide 20 mg (50%) of the title compound 4-Methyl-[1,2,3]thiadiazole-5-carbonyl chloride.

Example 16

Synthesis of 2-amino-4-methyl-pyrimidine-5-carboxylic Acid [2-(5-tert-butyl-3-methanesulfonylamino-2-methoxy-phenylcarbamoyl)-benzo[b]thiophenn-7-yl]-amide

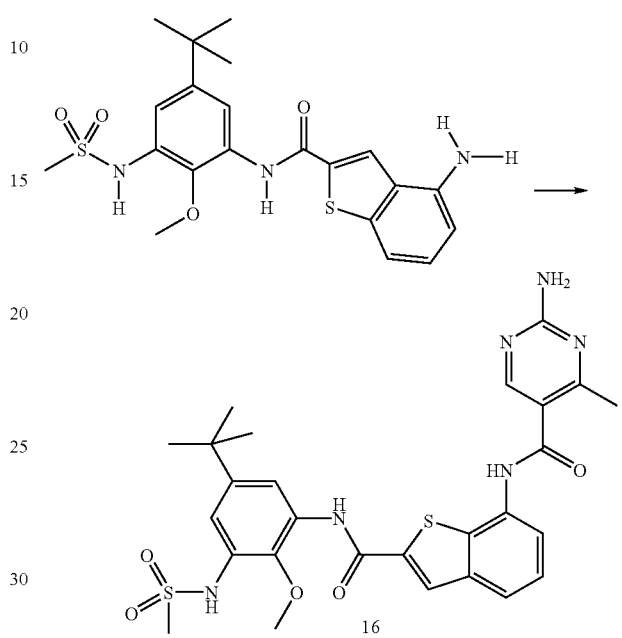

16

7-Amino-benzo[b]thiophene-2-carboxylic acid (5-tert-butyl-3-methanesulfonylamino-2-methoxy-phenyl-amide (25 mg, 0.055 mmol) was placed in 1,2-dichloroethane (2 mL). N,N-dimethylaminopyridine (6.65 mg, 0.055 mmol) and 5-(chlorocarbonyl-4-methyl-pyrimidinyl-2-yl) carbamic acid benzyl ester (16.0 mg, 0.055 mmol) were added at room temperature. The reaction mixture was stirred for 4 h and then passed through a 100 mg SCX (Varian) cartridge using 1 mL of 1,2-dichloroethane as eluant. The filtrate was concentrated in vacuo providing 16.4 mg of crude product. The crude product was hydrogenated by use of 10% Pd/C (25 mg) in 5 mL of EtOH under hydrogen at atmospheric pressure for 4 h. Filtration of the reaction mixture through diatomaceous earth and subsequent concentration in vacuo, produced a pale yellow solid. Purification by preparative reverse-phase HPLC (90:10 to 5:95 water/AcCN) produced 2.9 mg of the title compound as a white solid.

Example 17

Synthesis of 7-(2-chloro-3-pyridyl-carboxyamino)-benzo[b]thiophene-2-carboxylic Acid (5-tert-butyl-3-methanesulfonylamino-2-methoxy-phenyl-amide

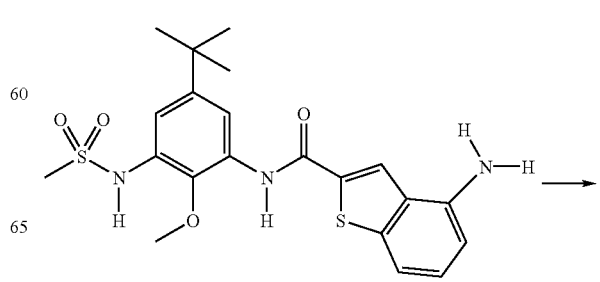

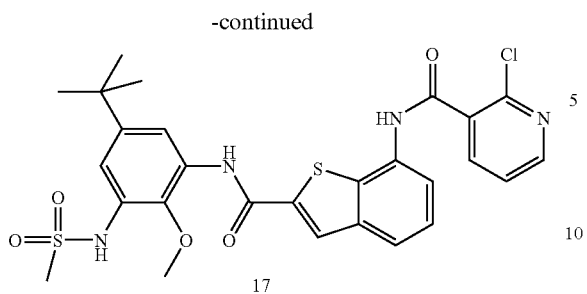

7-Amino-benzo[b]thiophene-2-carboxylic acid (5-tert-butyl-3-methanesulfonylamino-2-methoxy-phenyl-amide (25 mg, 0.055 mmol) was placed in 1,2-dichloroethane (2 mL). N,N-dimethylaminopyridine (6.65 mg, 0.055 mmol) and 2-chloro-3-nicotinoyl chloride (9.62 mg, 0.055 mmol) were added at room temperature. The reaction mixture was stirred for 4 h and then passed through a 100 mg SCX (Varian) cartridge using 1 mL of 1,2-dichloroethane as eluant. The filtrate was concentrated in vacuo. Purification by preparative reverse-phase HPLC (90:10 to 5:95 water/AcCN) produced 6.7 mg of the title compound as a white solid.

Example 18

Synthesis of N-[2-(5-tert-butyl-3-methanesulfonylamino-2-methoxy-phenylcarbamoyl)-benzo[b]thiophen-7-yl]-6-chloronicotinamide

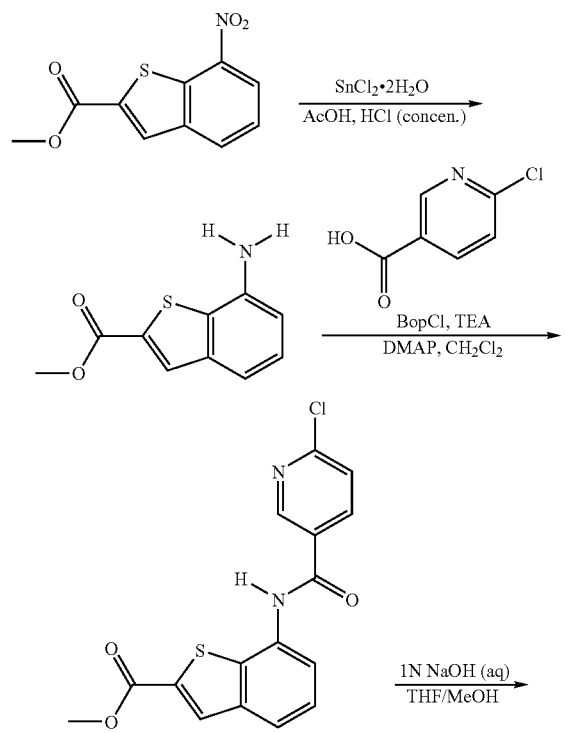

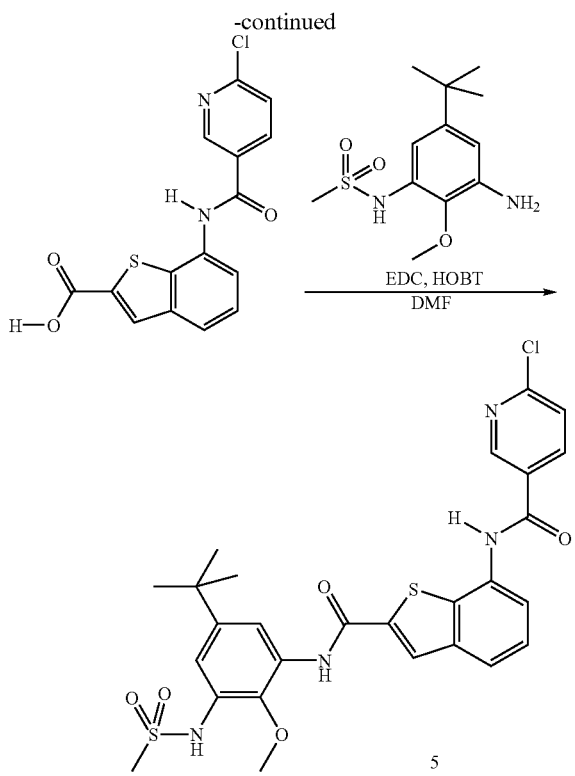

To a mixture of 7-nitro-benzo[b]thiophene-2-carboxylic acid methyl ester (100 mg) in acetic acid (4 mL) was added a solution of SnCl$_2$.2H$_2$O (10 eq) in 1.5 mL of concentrated HCl. The reaction was stirred at room temperature 12 h. The excess acid was partially removed in vacuo, and the reaction mixture was then poured into a flask (250 mL) and was neutralized with saturated NaHCO$_3$ solution at 0° C. The pH was brought up to pH 9 by adding solid NaHCO$_3$. The resulting aqueous mixture was diluted with EtOAc, and the Tin-by product was removed by filtering through a pad of diatomaceous earth. The pad was rinsed with EtOAc and the combined filtrates were partitioned in a separatory funnel. The aqueous layer was extracted with EtOAc two times. The combined organics were dried over MgSO$_4$, filtered and concentrated to give the desired 7-amino-benzo[b]thiophene-2-carboxylic acid methyl ester (100%).

To a solution of 6-chloronicotinic acid (1.5 eq) and triethylamine (2.0 eq) in CH$_2$Cl$_2$ (5 mL) was added BopCl (2.0 eq). After 15 min, 7-amino-benzo[b]thiophene-2-carboxylic acid methyl ester (87 mg) in CH$_2$Cl$_2$ and 4-dimethylaminopyridine (DMAP) (1.0 eq) were added to the reaction solution above. The reaction was stirred at room temperature 12 h. The reaction was then diluted with EtOAc, and washed with NaHCO$_3$ solution and brine. The organics were dried over MgSO$_4$, filtered and concentrated to give a crude material which was purified by flash chromatography on silica gel (20%-50% EtOAc/hexane) to provide 100 mg (68%) of the desired 7-[(6-chloro-pyridine-3-carbonyl)-amino]-benzo[b]thiophene-2-carboxylic acid methyl ester as a light yellow solid.

To a solution of the above methyl ester (91 mg) in THF/MeOH (3 mL/3 mL) was added 655 uL (2.5 eq) of 1N NaOH. The reaction solution was stirred at room temperature 12 h. Water CH$_2$Cl$_2$ and were added to the reaction. The mixture was acidified with 1N HCl to pH 4. The mixture was extracted with CH$_2$Cl$_2$ until most of the product was extracted into the organic layer. The organics were dried over MgSO$_4$, filtered and concentrated to give 7-[(6-chloro-pyridine-3-carbonyl)-amino]-benzo[b]thiophene-2-carboxylic acid as a light yellow solid (90 mg, >100%).

To a solution of the above carboxylic acid (50 mg) in DMF (1.5 mL) was added EDC (1.5 eq) and HOBT (1.5 eq). The reaction was stirred at room temperature for 15 min, then N-(3-amino-5-tert-butyl-2-methoxy-phenyl)-methanesulfonamide (1.2 eq) was added. The reaction was stirred 12 h, then the DMF was removed in vacuo, the residue was taken up in EtOAc and washed with water, followed by brine. The organics were dried over MgSO$_4$, filtered, and concentrated and the residue was purified by flash chromatography on silica gel (20%-60% EtOAc/hexane) to give the title compound as a white solid (36 mg, 41% yield for two steps).

Example 19

Synthesis of N-[2-(5-tert-Butyl-3-methanesulfonylamino-2-methoxy-phenylcarbamoyl)-benzo[b]thiophen-7-yl]-6-(morpholin-4-ylamino)-nicotinamide

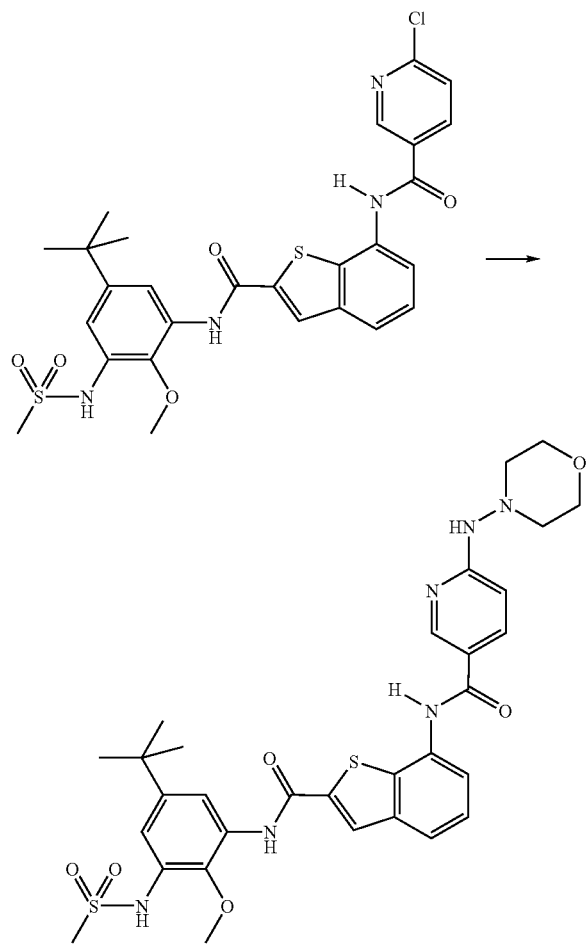

Suspended the Cl-pyridine (1 eq) in ca 6 mL CH3CN in 15 mL pressure tube. Added together the DBU (1 eq) and the N-amino morpholine (1 eq) along with ca 1 mL CH3CN. Added soln mixture in a single portion, washing with a bit more CH3CN. Sealed and heated (oil bath temp) to ca 120 C. and maintained 12 h (all solids dissolve upon the addn of the amine soln).

Color of soln now more orange-red. Cooled and unsealed and ran LC-MS (\34aliq1). See ion for desired material; Cl-pyrimidine appears gone; other unidentified peaks. Stripped CH3CN and partitioned residue thick gum between EtOAc and water. Extracted aq with more EtOAc and then washed combined EtOAc with water 2×, then brine, and then dried over MgSO4.

Assessment of Biological Properties

Inhibition of TNF Production in THP Cells

The inhibition of cytokine production can be observed by measuring inhibition of TNFα in lipopolysaccharide stimulated THP cells (for example, see W. Prichett et al., 1995, *J. Inflammation*, 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was non-sterile. Initial stock solutions were made in DMSO followed by dilution into RPMI 1640 2-fold higher than the desired final assay concentration. Confluent THP.1 cells (2×10$^6$ cells/ml, final conc.; American Type Culture Company, Rockville, Md.) were added to 96 well polypropylene round bottomed culture plates (Costar 3790; sterile) containing 125 µl test compound (2 fold concentrated) or DMSO vehicle (controls, blanks). DMSO concentration did not exceed 0.2% final. Cell mixture was allowed to preincubate for 30 min, 37° C., 5% CO$_2$ prior to stimulation with lipopolysaccharide (LPS; 1 µg/ml final; Siga L-2630, from *E. coli* serotype 0111.B4; stored as 1 mg/ml stock in endotoxin screened distilled H$_2$O at −80° C.). Blanks (unstimulated) received H$_2$O vehicle; final incubation volume was 250 µl. Overnight incubation (18-24 hr) proceeded as described above. Assay was terminated by centrifuging plates 5 min, room temperature, 1600 rpm (400×g); supernatants were transferred to clean 96 well plates and stored −80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated IC$_{50}$ value is the concentration of the test compound that caused a 50% decrease in the maximal TNFα production.

Preferred compounds will have an IC$_{50}$<10 uM in this assay.

Inhibition of Other Cytokines

By similar methods using peripheral blood monocytic cells, appropriate stimuli, and commercially available ELISA kits (or other method of detection such as radioimmunoassay), for a particular cytokine, inhibition of IL-1beta, GM-CSF, IL-6 and IL-8 can be demonstrated for preferred compounds (for example, see J. C. Lee et al., 1988, *Int. J. Immunopharmacol.*, 10, 835).

We claim:
1. A compound chosen from
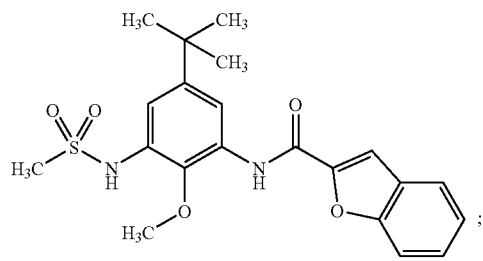;
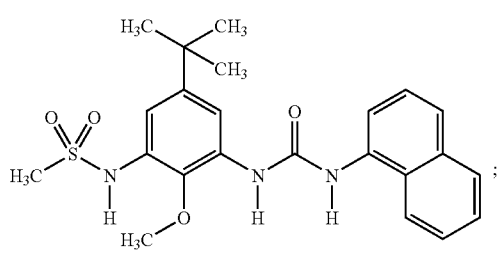;
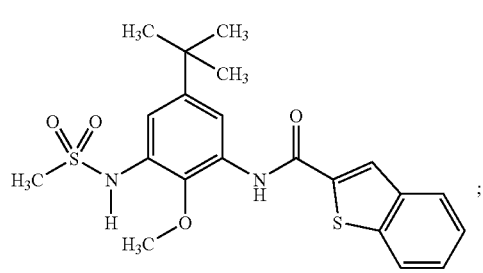;
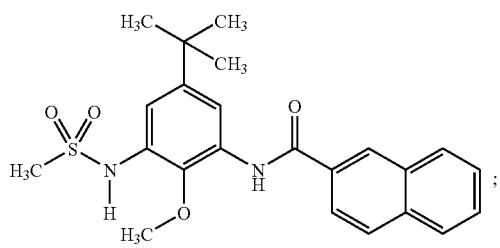;
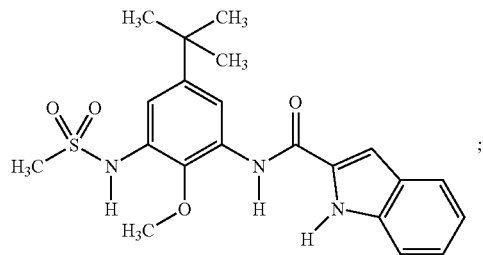;
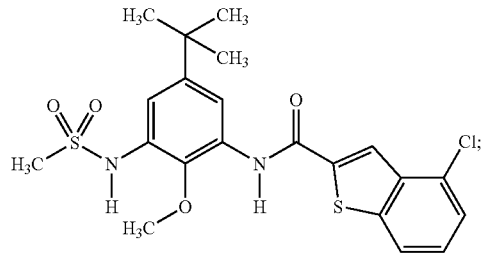;
-continued
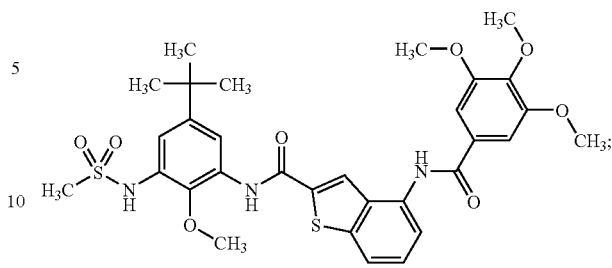;
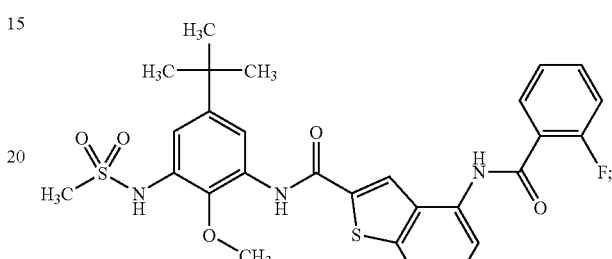;
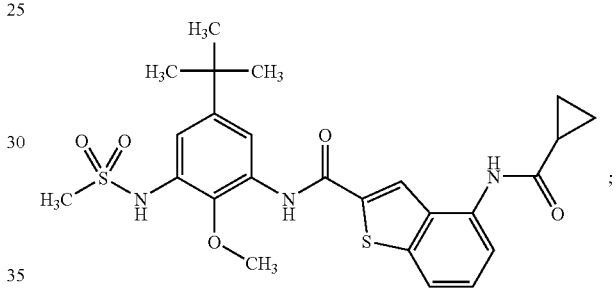;
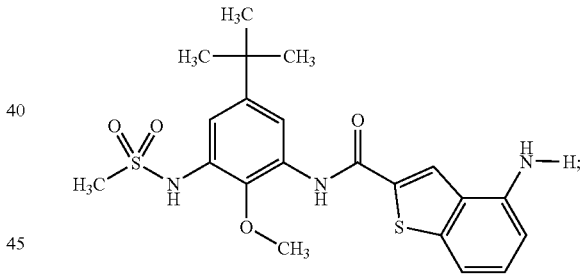;
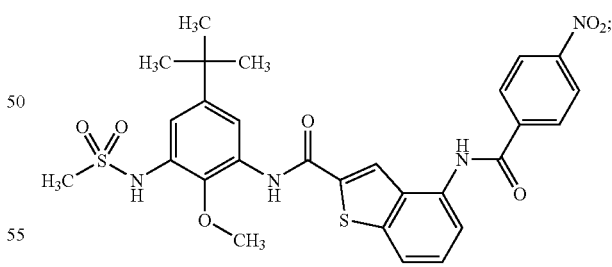;
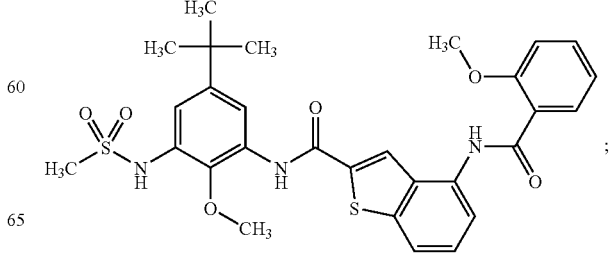;

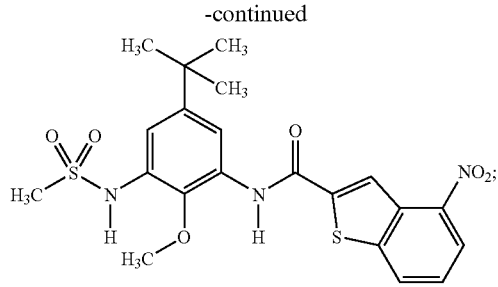
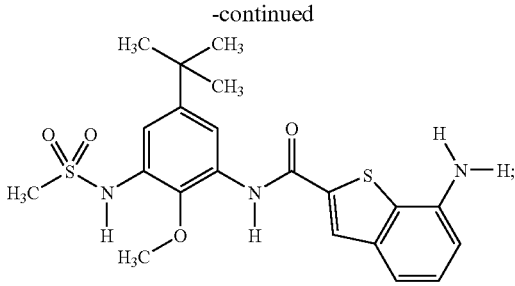
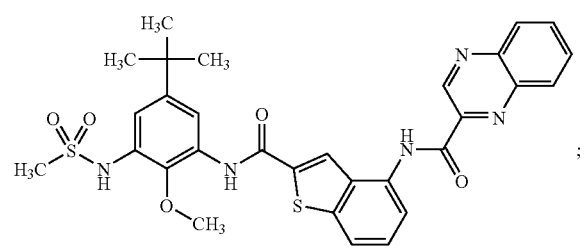
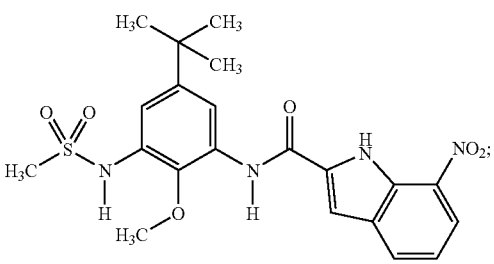
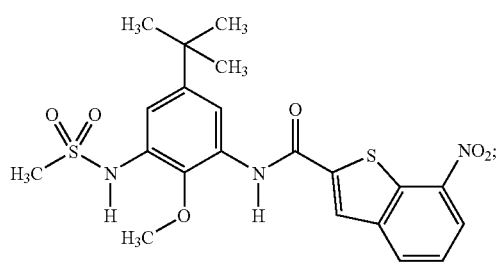
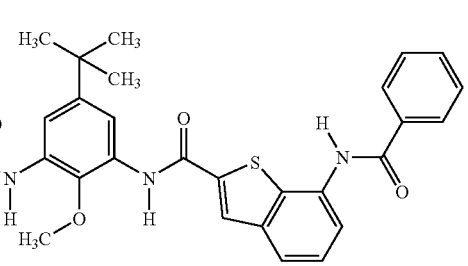
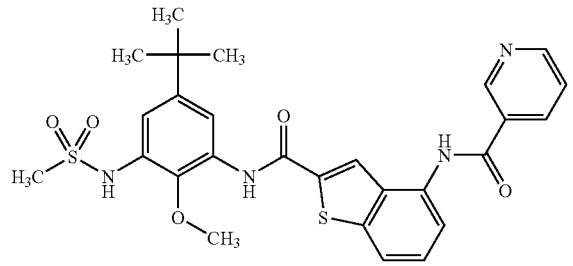
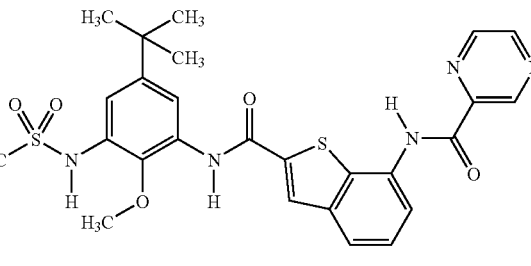
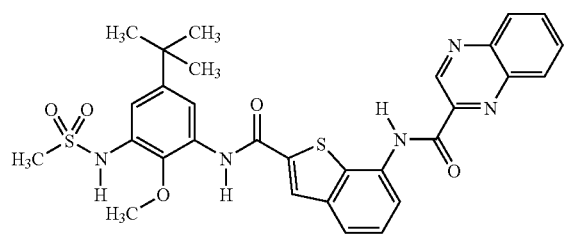
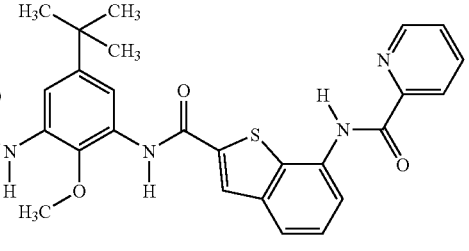
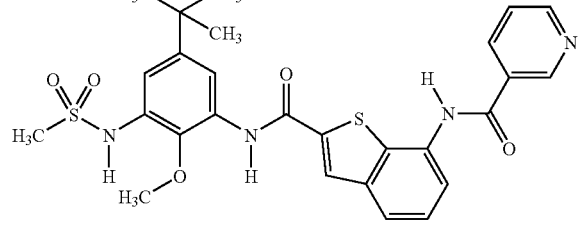
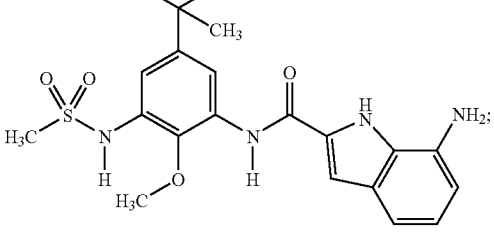

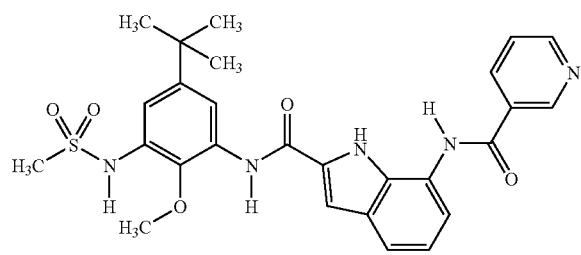
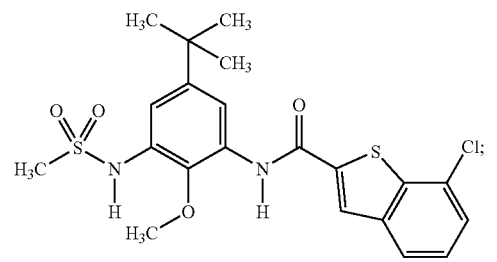
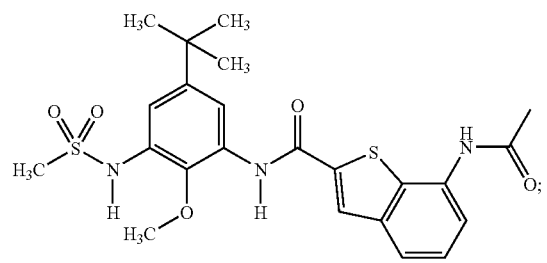
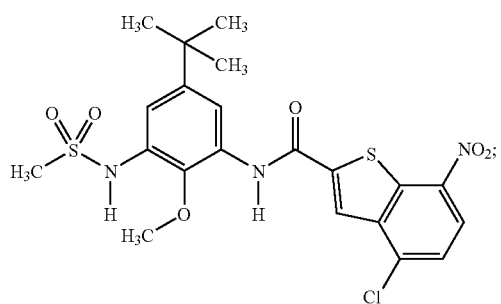
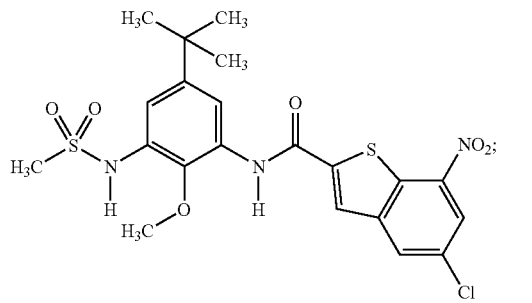
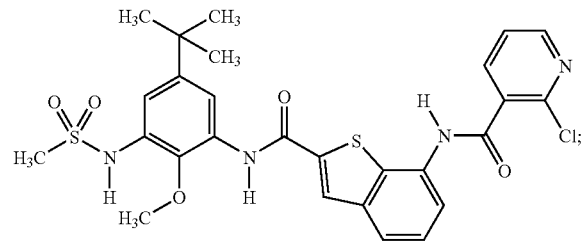
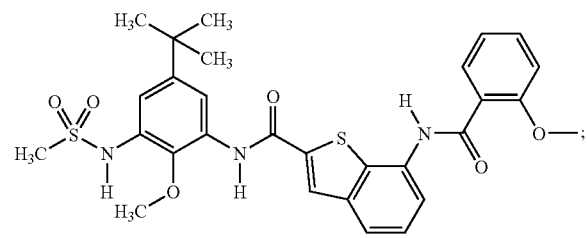
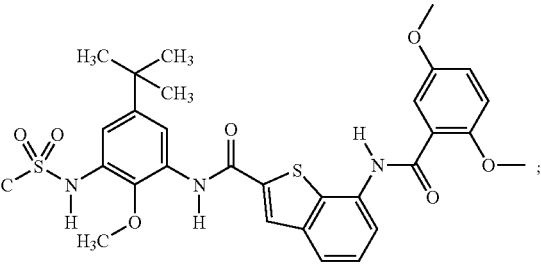
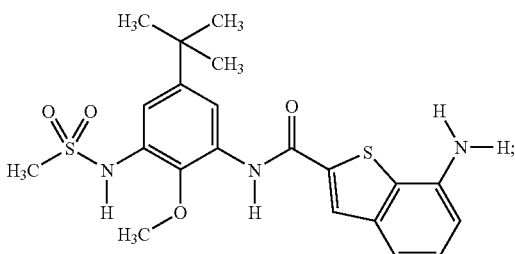
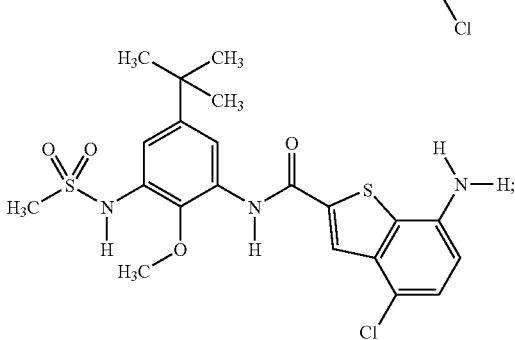
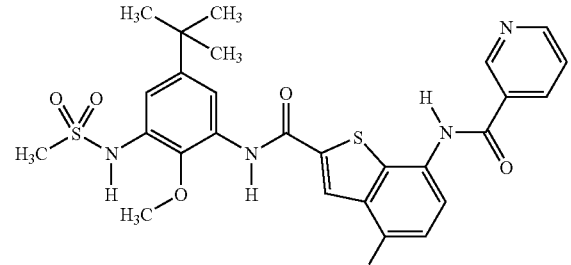
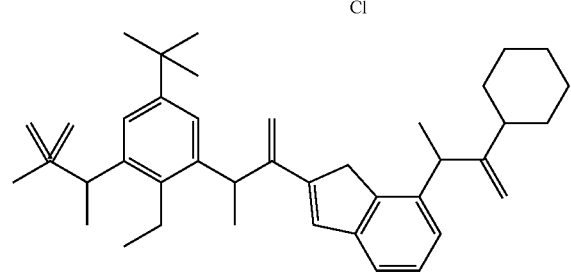

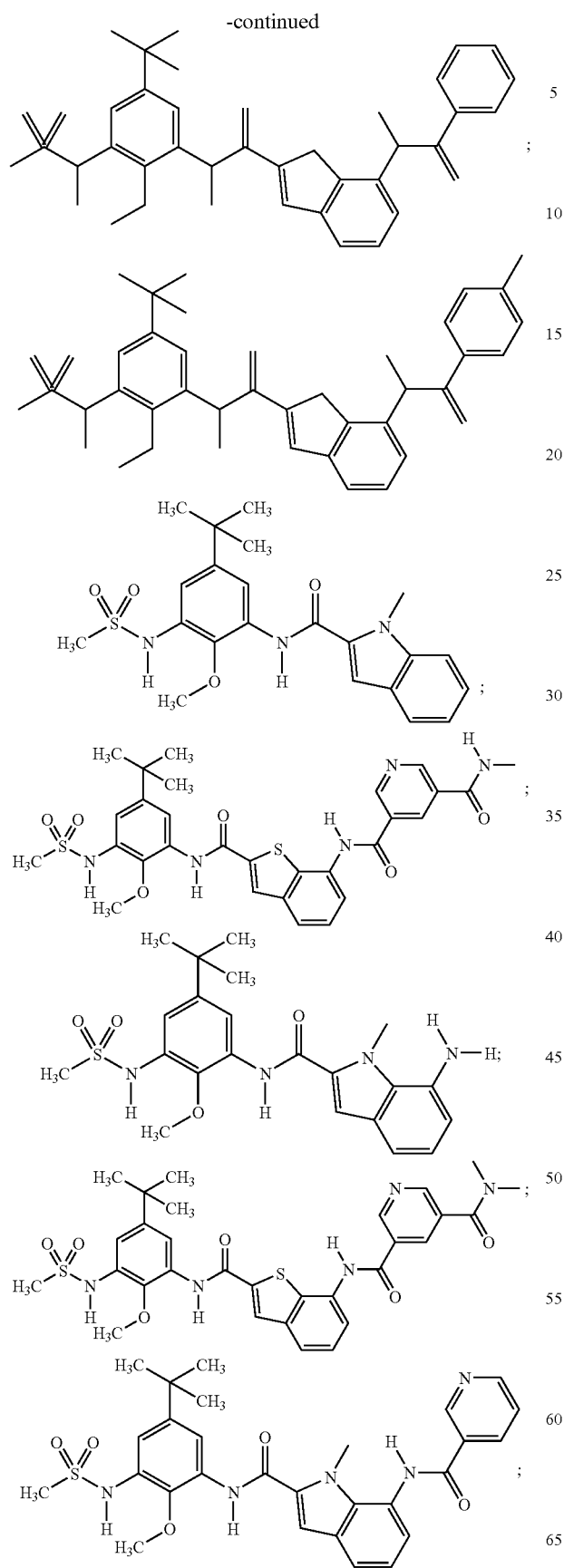
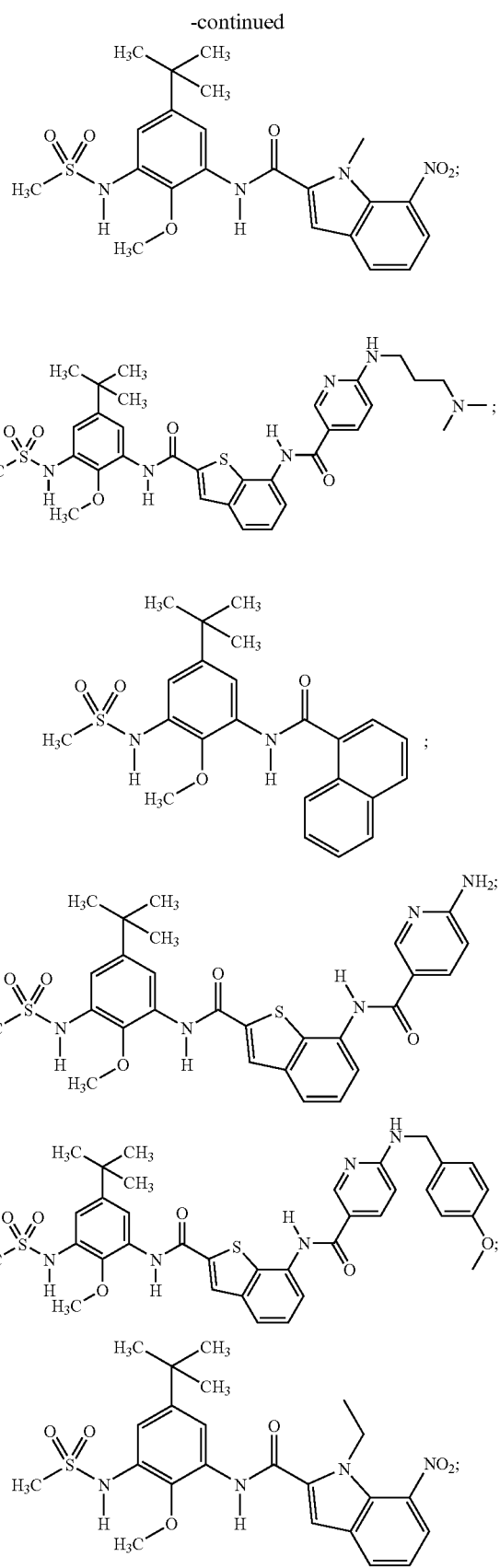

75
-continued
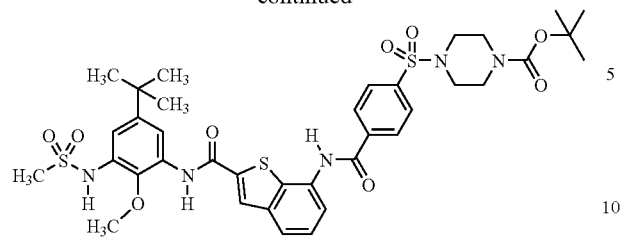
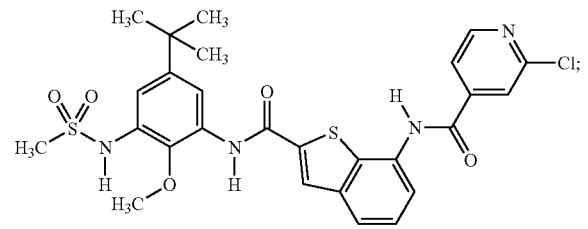
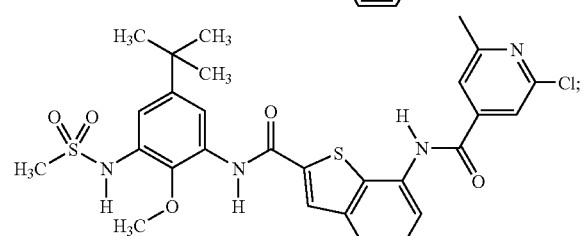
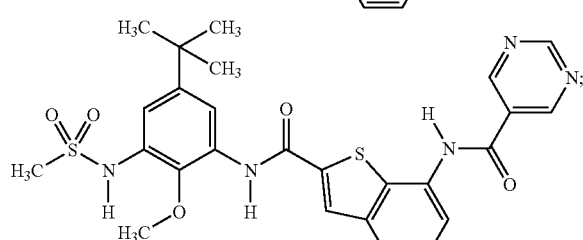
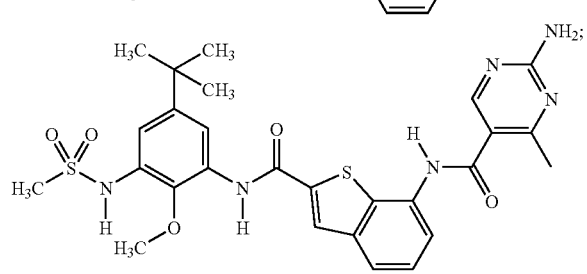
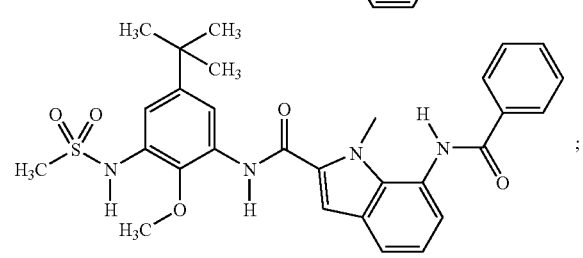
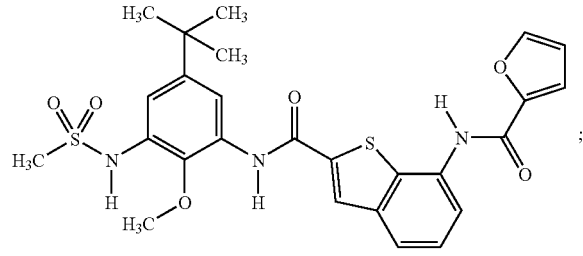
76
-continued
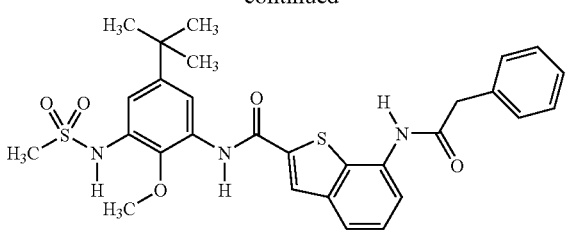
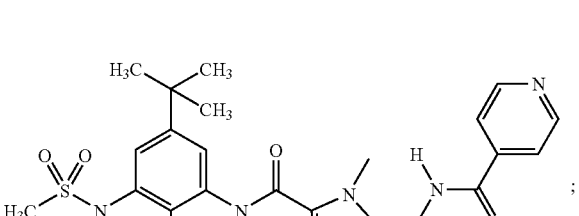
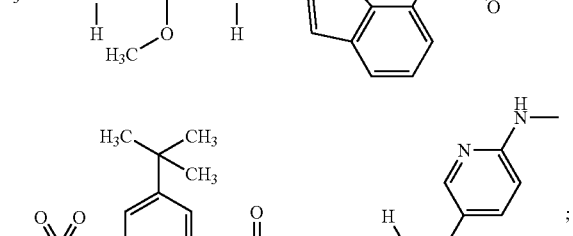
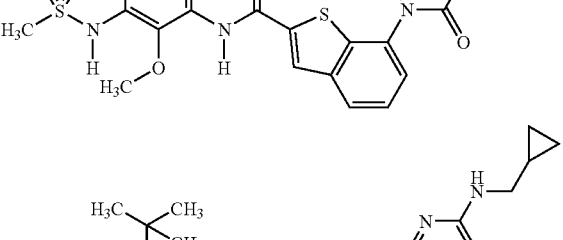
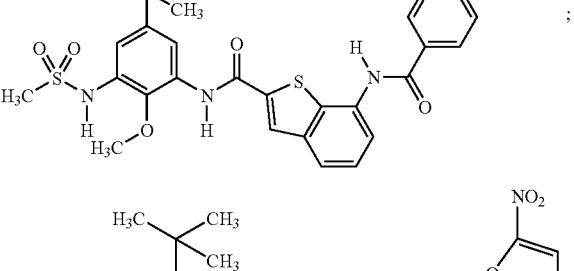
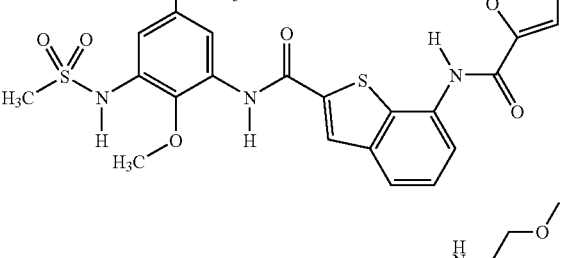
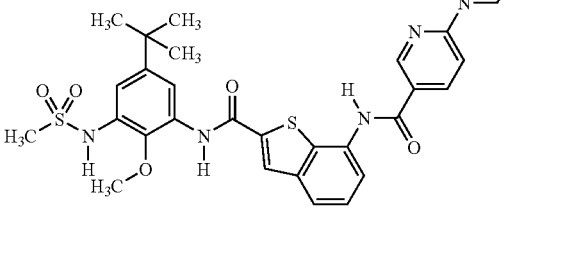

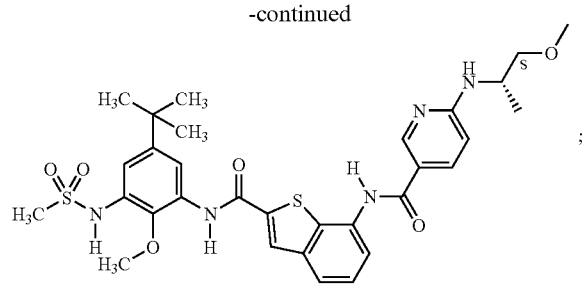
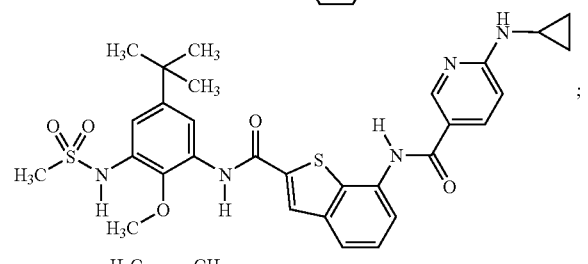
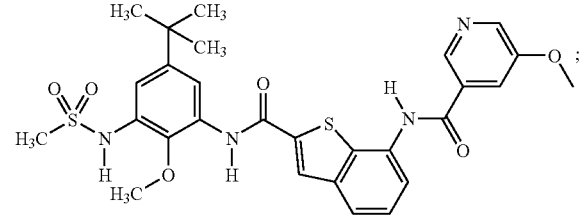
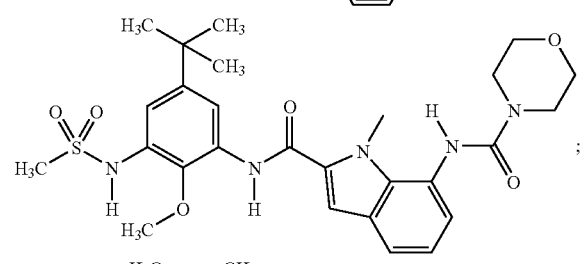
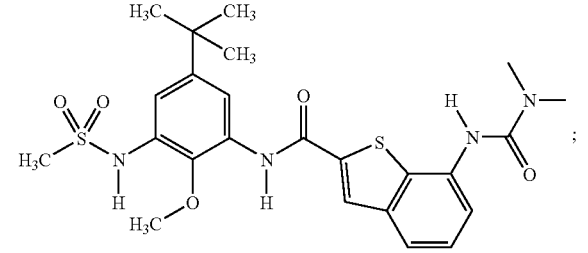
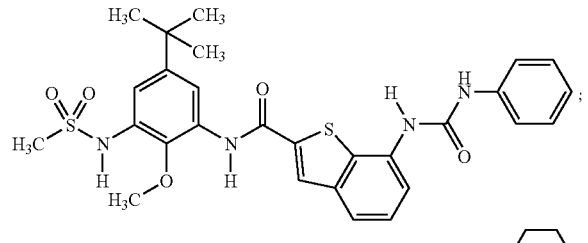
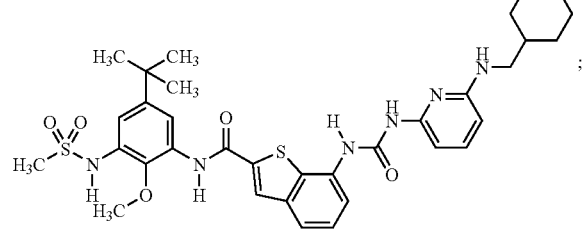
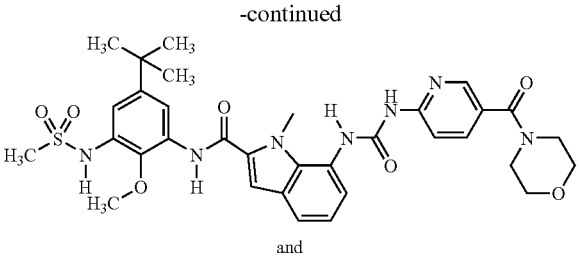
and
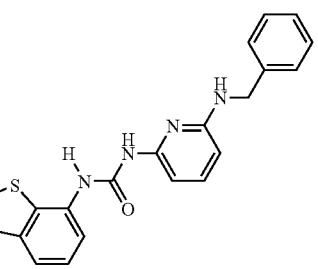
or the pharmaceutically acceptable acids and salts or isomers thereof.
2. A compound chosen from
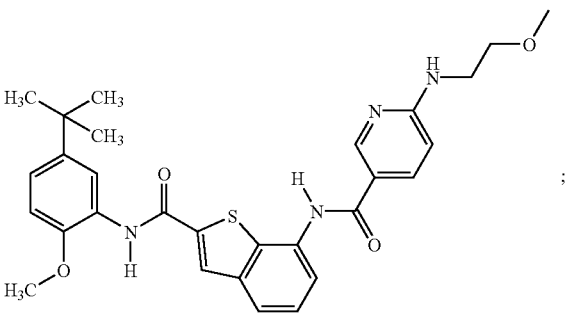
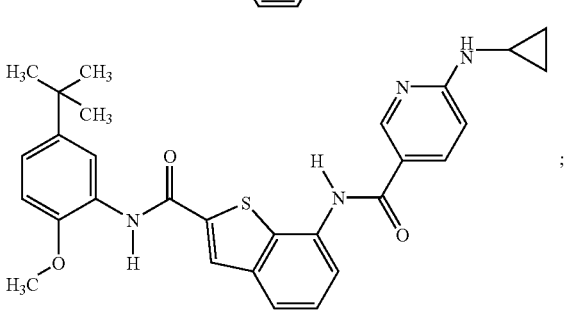
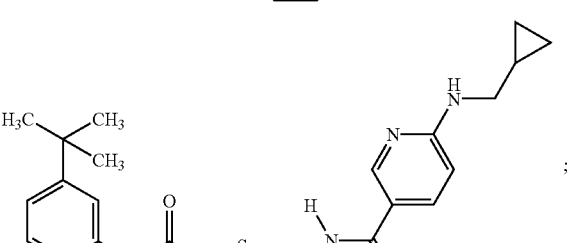
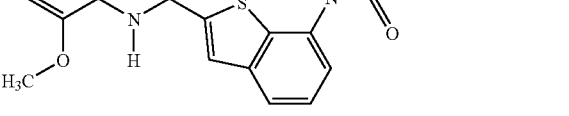

-continued
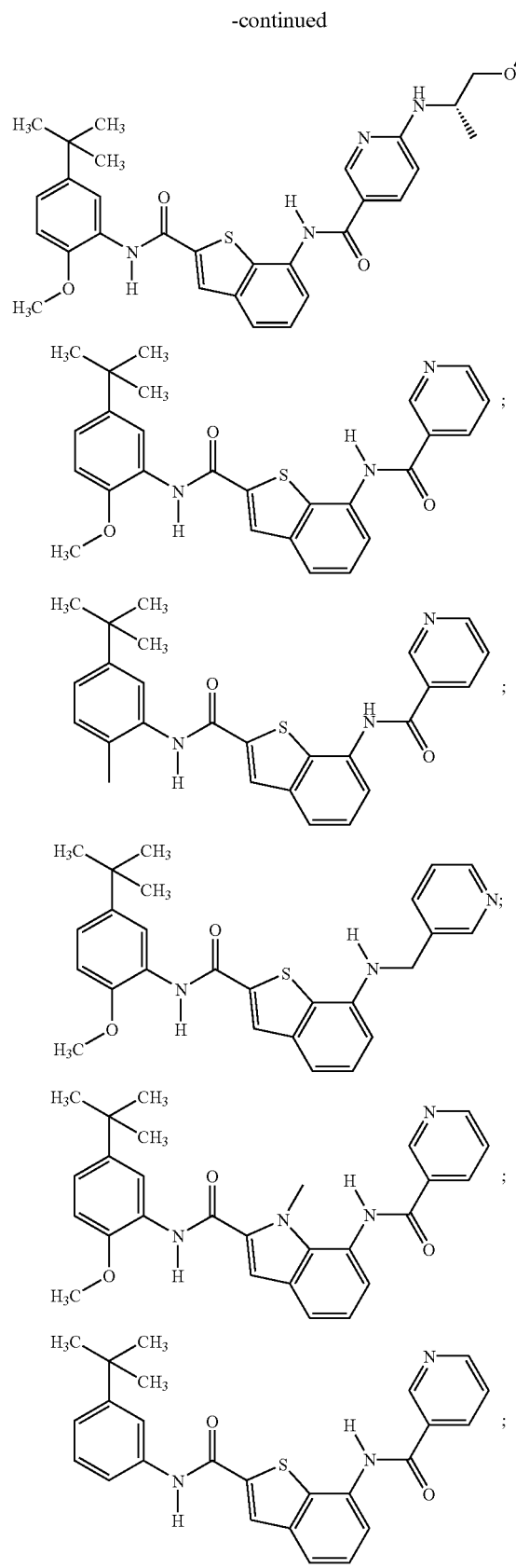
-continued
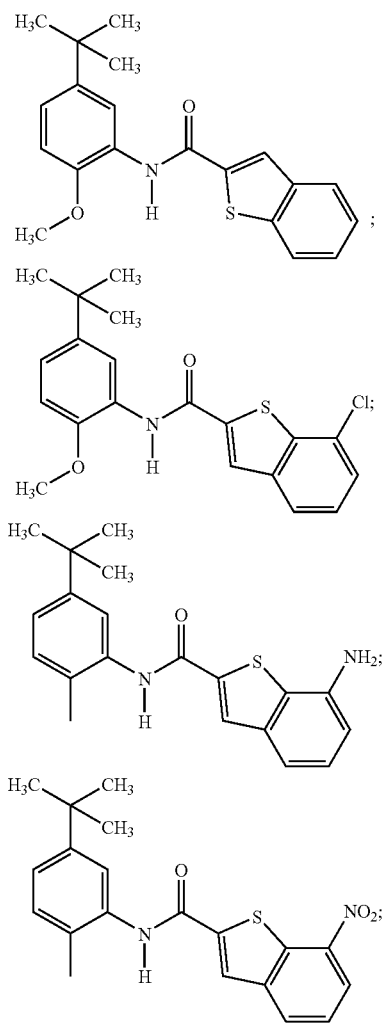
or the pharmaceutically acceptable acids and salts or isomers thereof.
3. A compound chosen from or the pharmaceutically acceptable acids and salts or isomers thereof.

4. A pharmaceutical composition comprising a compound according to claim 1 and one or more pharmaceutically acceptable carriers and/or adjuvants.

5. A method of treating a cytokine mediated disease or condition which comprises administering to a patient in need of such treatment a therapeutically effective amount of a compound according to claim 1, wherein the cytokine mediated disease or condition is selected from the group consisting of sepsis, Crohn's disease and ulcerative colitis.

6. A pharmaceutical composition comprising a compound according to claim 2 and one or more pharmaceutically acceptable carriers and/or adjuvants.

7. A method of treating a cytokine mediated disease or condition which comprises administering to a patient in need of such treatment a therapeutically effective amount of a compound according to claim 2, wherein the cytokine mediated disease or condition is selected from the group consisting of sepsis, Crohn's disease and ulcerative colitis.

8. A pharmaceutical composition comprising a effective amount of a compound according to claim 3 and one or more pharmaceutically acceptable carriers and/or adjuvants.

9. A method of treating a cytokine mediated disease or condition which comprises administering to a patient in need of such treatment a therapeutically effective amount of a compound according to claim 3, wherein the cytokine mediated disease or condition is selected from the group consisting of sepsis, Crohn's disease and ulcerative colitis.

* * * * *